United States Patent
Ogasawara et al.

(10) Patent No.: US 11,897,865 B2
(45) Date of Patent: Feb. 13, 2024

(54) ABHD12 INHIBITORS AND METHODS OF MAKING AND USING SAME

(71) Applicant: THE SCRIPPS RESEARCH INSTITUTE, La Jolla, CA (US)

(72) Inventors: Daisuke Ogasawara, La Jolla, CA (US); Taka-Aki Ichu, La Jolla, CA (US); Jonathan Hulce, La Jolla, CA (US); Benjamin F. Cravatt, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 563 days.

(21) Appl. No.: 17/055,081

(22) PCT Filed: May 14, 2019

(86) PCT No.: PCT/US2019/032290
§ 371 (c)(1),
(2) Date: Nov. 12, 2020

(87) PCT Pub. No.: WO2019/222267
PCT Pub. Date: Nov. 21, 2019

(65) Prior Publication Data
US 2021/0221790 A1    Jul. 22, 2021

Related U.S. Application Data

(60) Provisional application No. 62/671,998, filed on May 15, 2018.

(51) Int. Cl.
| | | |
|---|---|---|
| *C07D 401/14* | (2006.01) | |
| *C07D 401/12* | (2006.01) | |
| *C07D 401/04* | (2006.01) | |
| *C07D 471/04* | (2006.01) | |
| *C07D 471/08* | (2006.01) | |

(52) U.S. Cl.
CPC ......... *C07D 401/14* (2013.01); *C07D 401/04* (2013.01); *C07D 401/12* (2013.01); *C07D 471/04* (2013.01); *C07D 471/08* (2013.01)

(58) Field of Classification Search
CPC ... C07D 401/14; C07D 401/12; C07D 401/04
See application file for complete search history.

(56) References Cited

U.S. PATENT DOCUMENTS

| | | |
|---|---|---|
| 7,309,704 B2 | 12/2007 | Stamford et al. |
| 2004/0006086 A1* | 1/2004 | Stamford ............ C07D 213/75 514/252.03 |
| 2013/0331396 A1 | 12/2013 | Apodaca et al. |
| 2018/0105508 A1 | 4/2018 | Sabatini et al. |

FOREIGN PATENT DOCUMENTS

| | | |
|---|---|---|
| CN | 103003445 A | 3/2013 |
| WO | WO-2019222267 A1 | 11/2019 |
| WO | WO-2020232153 A1 | 11/2020 |

OTHER PUBLICATIONS

CN111138358A,, May 12, 2020. pgs 1-37 (Chinese Document).*
Golub et al., Science, vol. 286, Oct. 15, 1999, pp. 531-537.*
Co-pending U.S. Appl. No. 17/610,662, inventors Grice; Cheryl A et al., filed Nov. 11, 2021.
Kaczor et al. In Vitro Screening of Some Heterocyclic Compounds Against Human ABHD6 and ABHD12 Hydrolases. Letters In Drug Design & Discovery 11(7):944-952 (2014).
Ogasawara et al. Discovery and Optimization of Selective and in Vivo Active Inhibitors of the Lysophosphatidylserine Lipase [alpha]/[beta]-Hydrolase Domain-Containing 12 (ABHD12). J Med Chem 62(3):1643-1656 (2019).
Ogasawara et al. Selective blockade of the lyso-PS lipase ABHD12 stimulates immune responses in vivo. Nat Chem Biol 14(12):1099-1108 (2018).
Parkkari et al. Discovery of Triterpenoids as Reversible Inhibitors of alpha/beta-hydrolase Domain Containing 12 (ABHD12). PLoS One 9(5):e98286 (2014).
PCT/US2020/032721 International Search Report and Written Opinion dated Jul. 6, 2020.
Bachovchin et al. Identification of selective inhibitors of uncharacterized enzymes by high-throughput screening with fluorescent activity-based probes. Nat Biotechnol 27(4):387-394 (2009).
Bachovichin et al. Superfamily-wide portrait of serine hydrolase inhibition achieved by library-versus-library screening. PNAS USA 107(49):20941-20946 (2010).
Berge et al. Pharmaceutical Salts. Journal of Pharmaceutical Sciences 66(1):1-19 (Jan. 1977).
Blankman et al. ABHD12 controls brain lysophosphatidylserine pathways that are deregulated in a murine model of the neurodegenerative disease PHARC. PNAS USA 110:1500-1505 (2013).
Blankman et al. A comprehensive profile of brain enzymes that hydrolyze the endocannabinoid 2-arachidonoylglycerol. Chem. Biol. 14:1347-1356 (2007).

(Continued)

*Primary Examiner* — Samira J Jean-Louis
(74) *Attorney, Agent, or Firm* — WILSON SONSINI GOODRICH & ROSATI

(57) ABSTRACT

Provided herein are compounds and compositions useful as modulators of ABHD12. Furthermore, the subject compounds and compositions are useful as immunotherapies in treating, for instance, cancer or infectious diseases.

20 Claims, No Drawings

(56) References Cited

OTHER PUBLICATIONS

Cognetta et al. Selective N-Hydroxyhydantoin Carbamate Inhibitors of Mammalian Serine Hydrolases. Chem Biol 22(7):928-937 (2015).
PCT/US2019/032290 International Search Report and Written Opinion dated Jul. 25, 2019.
Pubchem CID 2796072 https://pubchem.ncbi.nlm.nih.gov/compound/2796072 (2005).
Pubchem CID 53499024 https://pubchem.ncbi.nlm.nih.gov/compound/53499024 (2011).

* cited by examiner

ABHD12 INHIBITORS AND METHODS OF MAKING AND USING SAME

CROSS-REFERENCE

This application claims benefit of U.S. Provisional Application No. 62/671,998, filed on May 15, 2018, which is herein incorporated by reference in its entirety.

STATEMENT AS TO FEDERALLY SPONSORED RESEARCH

This invention was made with government support under DA033760 awarded by the National Institutes of Health. The government has certain rights in the invention.

BACKGROUND

Alpha/beta-hydrolase domain containing 12 (ABHD12) is a serine hydrolase encoded by the ABHD12 gene that participates in the breakdown of the endocannabinoid neurotransmitter 2-arachidonylglycerol (2-AG) in the central nervous system.

BRIEF SUMMARY OF THE INVENTION

This disclosure provides, for example, compounds and compositions which are modulators of ABHD12, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of ABHD12 activity in warm-blooded animals such as humans.

In one aspect is a compound of Formula (I):

Formula (I)

wherein:
  each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;
  each $R^2$ is independently $C_{1-6}$alkyl;
  each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;
  each $R^4$ is independently $C_{1-6}$alkyl; and
  n is 0, 1, 2, or 3;

or a solvate, N-oxide, stereoisomer, or pharmaceutically acceptable salt thereof.

In another aspect is a compound of Formula (II):

Formula (II)

wherein:
  each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;
  each $R^2$ is independently $C_{1-6}$alkyl;
  each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;
  each $R^4$ is independently $C_{1-6}$alkyl;
  $R^5$ is selected from halogen, —CN, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy; and
  n is 0, 1, 2, or 3;

or a solvate, N-oxide, stereoisomer, or pharmaceutically acceptable salt thereof.

In another embodiment is a compound of Formula (II), or a solvate, N-oxide, stereoisomer, or pharmaceutically acceptable salt thereof, wherein each $R^5$ is independently selected from halogen, —CN, $C_{1-6}$alkynyl, $C_{1-6}$haloalkyl, —C(O)$R^2$, —O$R^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein each $R^5$ is independently selected from halogen, $C_{1-6}$haloalkyl, —O$R^3$, and phenyl substituted with 1 or 2 substituents independently selected from halogen, $C_{1-6}$alkyl, $C_{1-6}$alkoxy, and $C_{1-6}$haloalkoxy. In another embodiment is a compound of Formula (I) or (II), or a solvate, N-oxide, stereoisomer, or pharmaceutically acceptable salt thereof, wherein each $R^1$ is independently selected from halogen, —CN, $C_{1-6}$alkyl, $C_{1-6}$alkynyl, $C_{1-6}$haloalkyl, —C(O)$R^2$, —O$R^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I) or (II), or a solvate, N-oxide, stereoisomer, or pharmaceutically acceptable salt thereof, wherein each $R^1$ is independently selected from halogen, $C_{1-6}$alkyl, $C_{1-6}$haloalkyl, —O$R^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I) or (II), or a solvate, N-oxide, stereoisomer, or pharmaceutically acceptable salt thereof, wherein $R^3$ is $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, or -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, or -$C_{1-6}$alkyl-phenyl are optionally substituted with 1 or 2 substituents independently selected from halogen, $C_{1-6}$alkyl, $C_{1-6}$alkynyl, $C_{1-6}$alkoxy, $C_{1-6}$haloalkoxy, and $C(O)OR^4$. In another embodiment is a compound of Formula (I) or (II), or a solvate, N-oxide, stereoisomer, or pharmaceutically acceptable salt thereof, wherein $R^3$ is $C_{1-6}$alkyl, $C_{1-6}$haloalkyl, phenyl, or -$C_{1-6}$alkyl-phenyl, wherein phenyl or -$C_{1-6}$alkyl-phenyl are optionally substituted with 1 or 2 substituents independently selected from halogen, $C_{1-6}$alkyl, $C_{1-6}$alkynyl, $C_{1-6}$haloalkyl, $C_{1-6}$alkoxy, and $C_{1-6}$haloalkoxy. In another embodiment is a compound of Formula (I) or (II), or a solvate, N-oxide, stereoisomer, or pharmaceutically acceptable salt thereof, wherein $R^3$ is $C_{1-6}$haloalkyl, phenyl, or -$C_{1-6}$alkyl-phenyl, wherein phenyl or -$C_{1-6}$alkyl-phenyl are optionally substituted with 1 or 2 substituents independently selected from halogen, $C_{1-6}$haloalkyl, and $C_{1-6}$haloalkoxy. In another embodiment is a compound of Formula (I) or (II), or a solvate, N-oxide, stereoisomer, or pharmaceutically acceptable salt thereof, wherein n is 1, 2, or 3. In another embodiment is a compound of Formula (I) or (II), or a solvate, N-oxide, stereoisomer, or pharmaceutically acceptable salt thereof, wherein n is 1 or 2. In another embodiment is a compound of Formula (I) or (II), or a solvate, N-oxide, stereoisomer, or pharmaceutically acceptable salt thereof, wherein n is 1. In another embodiment is a compound of Formula (I) or (II), or a solvate, N-oxide, stereoisomer, or pharmaceutically acceptable salt thereof, wherein n is 2. In another embodiment is a compound of Formula (I) or (II), or a solvate, N-oxide, stereoisomer, or pharmaceutically acceptable salt thereof, wherein n is 0.

In another embodiment is a pharmaceutical composition comprising a compound of Formula (I) or (II) described herein, or a solvate, hydrate, tautomer, N-oxide, or a pharmaceutically acceptable salt thereof, and at least one pharmaceutically acceptable excipient.

In another embodiment is a method of treating a disease or disorder in a patient in need thereof, comprising administering to the patient a therapeutically effective amount of a compound of Formula (I) or (II) described herein, or a solvate, hydrate, tautomer, N-oxide, or a pharmaceutically acceptable salt thereof, wherein the disease or disorder is a neuropsychiatric disorder, an autoimmune disease, a neuroinflammatory disease, a neurodegenerative disease, or cancer. In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system. In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound initiates an immune response. In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein the compound is an immunotherapeutic agent. In another embodiment is a method of treating an infectious disease in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system.

DETAILED DESCRIPTION OF THE INVENTION

This disclosure is directed, at least in part, to modulators or inhibitors of ABHD12. For example, provided herein are compounds capable of inhibiting ABHD12.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)N($R^a$)$_2$, —N($R^a$)C(O)$OR^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N($R^a$)$_2$ (where t is 1 or 2) where each le is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)N($R^a$)$_2$, —N($R^a$)C(O)$OR^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)$OR^a$, —C(O)N($R^a$)$_2$, —N($R^a$)C(O)$OR^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$R$^a$ (where t is 1 or 2), —$R^b$—S(O)$_t$R$^a$ (where t is 1 or 2), —$R^b$—S(O)$_t$R$^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl is saturated, (i.e., containing single C—C bonds only) or partially unsaturated (i.e., containing one or more double bonds). Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heteroalkyl" refers to a straight or branched hydrocarbon chain alkyl radical containing no unsaturation, having from one to fifteen carbon atoms (e.g., $C_1$-$C_{15}$ alkyl) consisting of carbon and hydrogen atoms and one or two heteroatoms selected from O, N, and S, wherein the nitrogen or sulfur atoms may be optionally oxidized and the nitrogen atom may be quaternized. The heteroatom(s) may be placed at any position of the heteroalkyl group including between the rest of the heteroalkyl group and the fragment to which it is attached. The heteroalkyl is attached to the rest of the molecule by a single bond. Unless stated otherwise specifically in the specification, a heteroalkyl group is optionally substituted by one or more of the following substituents: halo, cyano, nitro, oxo, thioxo, imino, oximo, trimethylsilanyl, —$OR^a$, —$SR^a$, —$OC(O)$—$R^f$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where le is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

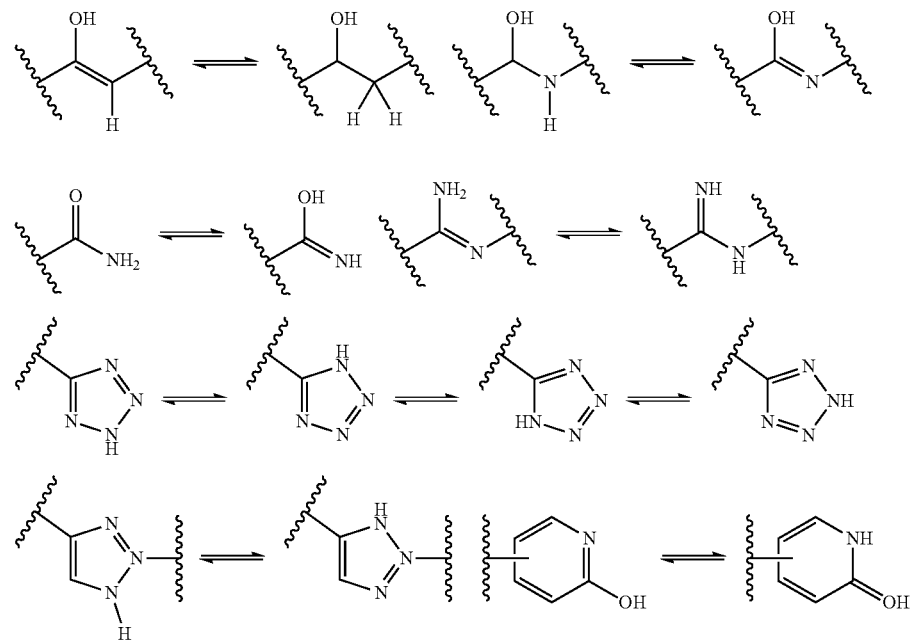

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I) or (II) described herein are modulators of ABHD12. The compounds of Formula (I) or (II) described herein, and compositions comprising these compounds, are useful for the treatment of a disease or disorder selected from a neuropsychiatric disorder, an autoimmune disease, a neuroinflammatory disease, a neurodegenerative disease, and cancer. In some embodiments compounds of Formula (I) or (II) described herein, and compositions comprising these compounds, stimulate a patient's immune system to treat a disease. In some embodiments, the disease is an infectious disease. In some embodiments, the disease is cancer.

In some embodiments is a compound of Formula (I):

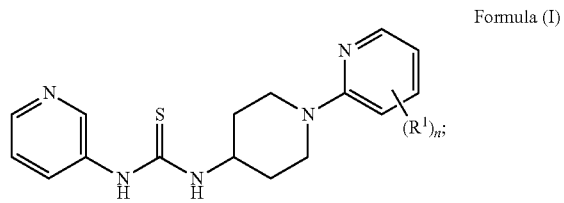

Formula (I)

wherein:
each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;
each $R^2$ is independently $C_{1-6}$alkyl;
each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;
each $R^4$ is independently $C_{1-6}$alkyl; and
n is 0, 1, 2, or 3;

or a solvate, N-oxide, stereoisomer, or pharmaceutically acceptable salt thereof.

In another embodiment is a compound of Formula (I), or a solvate, N-oxide, stereoisomer, or pharmaceutically acceptable salt thereof, wherein n is 0, 1, or 2. In another embodiment is a compound of Formula (I), or a solvate, N-oxide, stereoisomer, or pharmaceutically acceptable salt thereof, wherein n is 1, 2, or 3. In another embodiment is a compound of Formula (I), or a solvate, N-oxide, stereoisomer, or pharmaceutically acceptable salt thereof, wherein n is 1 or 2. In another embodiment is a compound of Formula (I), or a solvate, N-oxide, stereoisomer, or pharmaceutically acceptable salt thereof, wherein n is 0. In another embodiment is a compound of Formula (I), or a solvate, N-oxide, stereoisomer, or pharmaceutically acceptable salt thereof, wherein n is 1. In another embodiment is a compound of Formula (I), or a solvate, N-oxide, stereoisomer, or pharmaceutically acceptable salt thereof, wherein n is 2. In another embodiment is a compound of Formula (I), or a solvate, N-oxide, stereoisomer, or pharmaceutically acceptable salt thereof, wherein n is 3.

In another embodiment is a compound of Formula (I), or a solvate, N-oxide, stereoisomer, or pharmaceutically acceptable salt thereof, wherein n is 1, 2, or 3 and each $R^1$ is independently selected from halogen, —CN, $C_{1-6}$alkyl, $C_{1-6}$alkynyl, $C_{1-6}$haloalkyl, —(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 or 2 and each $R^1$ is independently selected from halogen, —CN, $C_{1-6}$alkyl, $C_{1-6}$alkynyl, $C_{1-6}$haloalkyl, —C(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy.

In another embodiment is a compound of Formula (I), or a solvate, N-oxide, stereoisomer, or pharmaceutically acceptable salt thereof, wherein n is 2 and each $R^1$ is independently selected from halogen, —CN, $C_{1-6}$alkyl, $C_{1-6}$alkynyl, $C_{1-6}$haloalkyl, —C(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 2 and each $R^1$ is independently selected from halogen, $C_{1-6}$alkyl, $C_{1-6}$haloalkyl, —OR$^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 2 and each $R^1$ is independently selected from halogen and $C_{1-6}$haloalkyl. In another embodiment is a compound of Formula (I), or a solvate, N-oxide, stereoisomer, or pharmaceutically acceptable salt thereof, wherein n is 2 and each $R^1$ is independently selected from —Cl and —CF$_3$. In another embodiment is a compound of Formula (I), or a solvate, N-oxide, stereoisomer, or pharmaceutically acceptable salt thereof, wherein n is 2 and each $R^1$ is independently selected from —F and —CF$_3$. In another embodiment is a compound of Formula (I), or a solvate, N-oxide, stereoisomer, or pharmaceutically acceptable salt thereof, wherein n is 2 and each $R^1$ is independently selected from halogen and $C_{1-6}$alkyl. In another embodiment is a compound of Formula (I), or a solvate, N-oxide, stereoisomer, or pharmaceutically acceptable salt thereof, wherein n is 2 and each $R^1$ is independently selected from —Cl and —CH$_3$. In another embodiment is a compound of Formula (I), or a solvate, N-oxide, stereoisomer, or pharmaceutically acceptable salt thereof, wherein n is 2 and each $R^1$ is independently selected from —F and —CH$_3$. In another embodiment is a compound of Formula (I), or a solvate, N-oxide, stereoisomer, or pharmaceutically acceptable salt thereof, wherein n is 2 and each $R^1$ is independently selected from halogen and —OR$^3$. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is $C_{1-6}$haloalkyl. In another embodiment is a compound of Formula (I), or a solvate, N-oxide, stereoisomer, or pharmaceutically acceptable salt thereof, wherein n is 2 and each $R^1$ is independently selected from —Cl and —OCF$_3$. In another embodiment is a compound of Formula (I), or a solvate, N-oxide, stereoisomer, or pharmaceutically acceptable salt thereof, wherein n is 2 and each $R^1$ is independently selected from —F and —OCF$_3$. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and C(O)OR$^4$. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is phenyl optionally substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is phenyl substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is phenyl substituted with 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is phenyl substituted with 1 substituent selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is -$C_{1-6}$alkyl-phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and C(O)OR$^4$. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is -$C_{1-6}$alkyl-phenyl optionally substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —OR$^3$, and $R^3$ is -$C_{1-}$ $_6$alkyl-phenyl substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl substituted with 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl substituted with 1 substituent selected from halogen, $C_{1-6}$haloalkyl, and $C_{1-6}$haloalkoxy.

In another embodiment is a compound of Formula (I), or a solvate, N-oxide, stereoisomer, or pharmaceutically acceptable salt thereof, wherein n is 1 and $R^1$ is selected from halogen, —CN, $C_{1-6}$alkyl, $C_{1-6}$alkynyl, $C_{1-6}$haloalkyl, —$C(O)R^2$, —$OR^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 and $R^1$ is selected from halogen, $C_{1-6}$alkyl, $C_{1-6}$haloalkyl, —$OR^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 and $R^1$ is halogen. In another embodiment is a compound of Formula (I), or a solvate, N-oxide, stereoisomer, or pharmaceutically acceptable salt thereof, wherein n is 1 and $R^1$ is —Cl. In another embodiment is a compound of Formula (I), or a solvate, N-oxide, stereoisomer, or pharmaceutically acceptable salt thereof, wherein n is 1 and $R^1$ is —F. In another embodiment is a compound of Formula (I), or a solvate, N-oxide, stereoisomer, or pharmaceutically acceptable salt thereof, wherein n is 1 and $R^1$ is $C_{1-6}$alkyl. In another embodiment is a compound of Formula (I), or a solvate, N-oxide, stereoisomer, or pharmaceutically acceptable salt thereof, wherein n is 1 and $R^1$ is —$CH_3$. In another embodiment is a compound of Formula (I), or a solvate, N-oxide, stereoisomer, or pharmaceutically acceptable salt thereof, wherein n is 1 and $R^1$ is $C_{1-6}$haloalkyl. In another embodiment is a compound of Formula (I), or a solvate, N-oxide, stereoisomer, or pharmaceutically acceptable salt thereof, wherein n is 1 and $R^1$ is —$CF_3$. In another embodiment is a compound of Formula (I), or a solvate, N-oxide, stereoisomer, or pharmaceutically acceptable salt thereof, wherein n is 1 and $R^1$ is —$OR^3$. In another embodiment is a compound of Formula (I), or a solvate, N-oxide, stereoisomer, or pharmaceutically acceptable salt thereof, wherein n is 1, $R^1$ is —$OR^3$, and $R^3$ is $C_{1-6}$haloalkyl. In another embodiment is a compound of Formula (I), or a solvate, N-oxide, stereoisomer, or pharmaceutically acceptable salt thereof, wherein n is 1 and $R^1$ is —$OCF_3$. In another embodiment is a compound of Formula (I), or a solvate, N-oxide, stereoisomer, or pharmaceutically acceptable salt thereof, wherein n is 1, $R^1$ is —$OR^3$, and $R^3$ is phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and $C(O)OR^4$. In another embodiment is a compound of Formula (I), or a solvate, N-oxide, stereoisomer, or pharmaceutically acceptable salt thereof, wherein n is 1, $R^1$ is —$OR^3$, and $R^3$ is phenyl optionally substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is phenyl substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is phenyl substituted with 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is phenyl substituted with 1 substituent selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is -$C_{1-6}$alkyl-phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and $C(O)OR^4$. In another embodiment is a compound of Formula (I), or a solvate, N-oxide, stereoisomer, or pharmaceutically acceptable salt thereof, wherein n is 1, $R^1$ is —$OR^3$, and $R^3$ is -$C_{1-6}$alkyl-phenyl optionally substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 1 or 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 2 substituents independently selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 1 substituent selected from halogen, $C_{1-6}$haloalkyl, and $C_{1-6}$haloalkoxy. In another embodiment is a compound of Formula (I), or a solvate, N-oxide, stereoisomer, or pharmaceutically acceptable salt thereof, wherein n is 1 and $R^1$ is phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 and $R^1$ is phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 and $R^1$ is phenyl substituted with 1 substituent selected from halogen, $C_{1-6}$alkyl, $C_{1-6}$haloalkyl, $C_{1-6}$alkoxy, and $C_{1-6}$haloalkoxy. In another embodiment is a compound of Formula (I), or a solvate, N-oxide, stereoisomer, or pharmaceutically acceptable salt thereof, wherein n is 1 and $R^1$ is phenyl substituted with 2 substituents independently selected from halogen, $C_{1-6}$alkyl, $C_{1-6}$haloalkyl, $C_{1-6}$alkoxy, and $C_{1-6}$haloalkoxy.

In some embodiments is a compound of Formula (II):

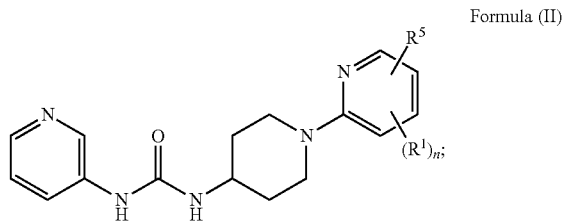

Formula (II)

wherein:
each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;
each $R^2$ is independently $C_{1-6}$alkyl;
each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;
each $R^4$ is independently $C_{1-6}$alkyl;
$R^5$ is selected from halogen, —CN, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy; and
n is 0, 1, 2, or 3;
or a solvate, N-oxide, stereoisomer, or pharmaceutically acceptable salt thereof.

In another embodiment is a compound of Formula (II), or a solvate, N-oxide, stereoisomer, or pharmaceutically acceptable salt thereof, wherein $R^5$ is selected from halogen, —CN, $C_{1-6}$alkynyl, $C_{1-6}$haloalkyl, —C(O)$R^2$, —O$R^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein $R^5$ is selected from halogen, $C_{1-6}$haloalkyl, —O$R^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein $R^5$ is halogen. In another embodiment is a compound of Formula (II), or a solvate, N-oxide, stereoisomer, or pharmaceutically acceptable salt thereof, wherein $R^5$ is —Cl. In another embodiment is a compound of Formula (II), or a solvate, N-oxide, stereoisomer, or pharmaceutically acceptable salt thereof, wherein $R^5$ is —F. In another embodiment is a compound of Formula (II), or a solvate, N-oxide, stereoisomer, or pharmaceutically acceptable salt thereof, wherein $R^5$ is $C_{1-6}$haloalkyl. In another embodiment is a compound of Formula (II), or a solvate, N-oxide, stereoisomer, or pharmaceutically acceptable salt thereof, wherein $R^5$ is —CF$_3$. In another embodiment is a compound of Formula (II), or a solvate, N-oxide, stereoisomer, or pharmaceutically acceptable salt thereof, wherein $R^5$ is —O$R^3$. In another embodiment is a compound of Formula (II), or a solvate, N-oxide, stereoisomer, or pharmaceutically acceptable salt thereof, wherein $R^5$ is —O$R^3$ and $R^3$ is $C_{1-6}$haloalkyl. In another embodiment is a compound of Formula (II), or a solvate, N-oxide, stereoisomer, or pharmaceutically acceptable salt thereof, wherein $R^5$ is —OCF$_3$. In another embodiment is a compound of Formula (II), or a solvate, N-oxide, stereoisomer, or pharmaceutically acceptable salt thereof, wherein $R^5$ is —O$R^3$ and $R^3$ is phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and C(O)O$R^4$. In another embodiment is a compound of Formula (II), or a solvate, N-oxide, stereoisomer, or pharmaceutically acceptable salt thereof, wherein $R^5$ is —O$R^3$ and $R^3$ is phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is phenyl substituted with 1 substituent selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is -$C_{1-6}$alkyl-phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and C(O)O$R^4$. In another embodiment is a compound of Formula (II), or a solvate, N-oxide, stereoisomer, or pharmaceutically acceptable salt thereof, $R^5$ is —O$R^3$ and $R^3$ is -$C_{1-6}$alkyl-phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ an $R^3$ is -$C_{1-6}$alkyl-phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is -$C_{1-6}$alkyl-phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is —O$R^3$ and $R^3$ is -$C_{1-6}$alkyl-phenyl substituted with 1 substituent selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein $R^5$ is phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein $R^5$ is phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein $R^5$ is phenyl substituted with 1 substituent selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein $R^5$ is phenyl substituted with 2 substituents independently selected from halogen, $C_{1-6}$alkyl, $C_{1-6}$haloalkyl, $C_{1-6}$alkoxy, and $C_{1-6}$haloalkoxy.

In another embodiment is a compound of Formula (II), or a solvate, N-oxide, stereoisomer, or pharmaceutically acceptable salt thereof, wherein n is 0, 1, or 2. In another embodiment is a compound of Formula (II), or a solvate, N-oxide, stereoisomer, or pharmaceutically acceptable salt thereof, wherein n is 1, 2, or 3. In another embodiment is a compound of Formula (II), or a solvate, N-oxide, stereoisomer, or pharmaceutically acceptable salt thereof, wherein n is 1 or 2. In another embodiment is a compound of Formula (II), or a solvate, N-oxide, stereoisomer, or pharmaceutically acceptable salt thereof, wherein n is 0. In another embodiment is a compound of Formula (II), or a solvate, N-oxide, stereoisomer, or pharmaceutically acceptable salt thereof, wherein n is 1. In another embodiment is a compound of Formula (II), or a solvate, N-oxide, stereoisomer, or pharmaceutically acceptable salt thereof, wherein n is 2. In another embodiment is a compound of Formula (II), or a solvate, N-oxide, stereoisomer, or pharmaceutically acceptable salt thereof, wherein n is 3.

In another embodiment is a compound of Formula (II), or a solvate, N-oxide, stereoisomer, or pharmaceutically acceptable salt thereof, wherein n is 1, 2, or 3 and each $R^1$ is independently selected from halogen, —CN, $C_{1-6}$alkyl, $C_{1-6}$alkynyl, $C_{1-6}$haloalkyl, —C(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 or 2 and each $R^1$ is independently selected from halogen, —CN, $C_{1-6}$alkyl, $C_{1-6}$alkynyl, $C_{1-6}$haloalkyl, —C(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy.

In another embodiment is a compound of Formula (II), or a solvate, N-oxide, stereoisomer, or pharmaceutically acceptable salt thereof, wherein n is 2 and each $R^1$ is independently selected from halogen, —CN, $C_{1-6}$alkyl, $C_{1-6}$alkynyl, $C_{1-6}$haloalkyl, —C(O)$R^2$, —OR$^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 2 and each $R^1$ is independently selected from halogen, $C_{1-6}$alkyl, $C_{1-6}$haloalkyl, —OR$^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 2 and each $R^1$ is independently selected from halogen and $C_{1-6}$haloalkyl. In another embodiment is a compound of Formula (II), or a solvate, N-oxide, stereoisomer, or pharmaceutically acceptable salt thereof, wherein n is 2 and each $R^1$ is independently selected from —Cl and —CF$_3$. In another embodiment is a compound of Formula (II), or a solvate, N-oxide, stereoisomer, or pharmaceutically acceptable salt thereof, wherein n is 2 and each $R^1$ is independently selected from —F and —CF$_3$. In another embodiment is a compound of Formula (II), or a solvate, N-oxide, stereoisomer, or pharmaceutically acceptable salt thereof, wherein n is 2 and each $R^1$ is independently selected from halogen and $C_{1-6}$alkyl. In another embodiment is a compound of Formula (II), or a solvate, N-oxide, stereoisomer, or pharmaceutically acceptable salt thereof, wherein n is 2 and each $R^1$ is independently selected from —Cl and —CH$_3$. In another embodiment is a compound of Formula (II), or a solvate, N-oxide, stereoisomer, or pharmaceutically acceptable salt thereof, wherein n is 2 and each $R^1$ is independently selected from —F and —CH$_3$. In another embodiment is a compound of Formula (II), or a solvate, N-oxide, stereoisomer, or pharmaceutically acceptable salt thereof, wherein n is 2 and each $R^1$ is independently selected from halogen and —OR$^3$. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is $C_{1-6}$haloalkyl. In another embodiment is a compound of Formula (II), or a solvate, N-oxide, stereoisomer, or pharmaceutically acceptable salt thereof, wherein n is 2 and each $R^1$ is independently selected from —Cl and —OCF$_3$. In another embodiment is a compound of Formula (II), or a solvate, N-oxide, stereoisomer, or pharmaceutically acceptable salt thereof, wherein n is 2 and each $R^1$ is independently selected from —F and —OCF$_3$. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and C(O)OR$^4$. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —OR$^3$, and $R^3$ is phenyl substituted with 1 substituent selected from halogen, $C_{1-6}$haloalkyl, and $C_{1-6}$haloalkoxy.

In another embodiment is a compound of Formula (II), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl optionally substituted with 1 or 2 substituents independently selected from halogen, $C_{1-6}$alkyl, $C_{1-6}$haloalkyl, $C_{1-6}$alkoxy, $C_{1-6}$haloalkoxy, and $C(O)OR^4$. In another embodiment is a compound of Formula (II), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 2, each $R^1$ is independently selected from halogen and —$OR^3$, and $R^3$ is -$C_{1-6}$alkyl-phenyl substituted with 1 substituent selected from halogen, $C_{1-6}$haloalkyl, and $C_{1-6}$haloalkoxy.

In another embodiment is a compound of Formula (II), or a solvate, N-oxide, stereoisomer, or pharmaceutically acceptable salt thereof, wherein n is 1 and $R^1$ is selected from halogen, —CN, $C_{1-6}$alkyl, $C_{1-6}$alkynyl, $C_{1-6}$haloalkyl, —$C(O)R^2$, —$OR^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 and $R^1$ is selected from halogen, $C_{1-6}$alkyl, $C_{1-6}$haloalkyl, —$OR^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 and $R^1$ is halogen. In another embodiment is a compound of Formula (II), or a solvate, N-oxide, stereoisomer, or pharmaceutically acceptable salt thereof, wherein n is 1 and $R^1$ is —Cl. In another embodiment is a compound of Formula (II), or a solvate, N-oxide, stereoisomer, or pharmaceutically acceptable salt thereof, wherein n is 1 and $R^1$ is —F. In another embodiment is a compound of Formula (II), or a solvate, N-oxide, stereoisomer, or pharmaceutically acceptable salt thereof, wherein n is 1 and $R^1$ is $C_{1-6}$alkyl. In another embodiment is a compound of Formula (II), or a solvate, N-oxide, stereoisomer, or pharmaceutically acceptable salt thereof, wherein n is 1 and $R^1$ is —$CH_3$. In another embodiment is a compound of Formula (II), or a solvate, N-oxide, stereoisomer, or pharmaceutically acceptable salt thereof, wherein n is 1 and $R^1$ is $C_{1-6}$haloalkyl. In another embodiment is a compound of Formula (II), or a solvate, N-oxide, stereoisomer, or pharmaceutically acceptable salt thereof, wherein n is 1 and $R^1$ is $CF_3$. In another embodiment is a compound of Formula (II), or a solvate, N-oxide, stereoisomer, or pharmaceutically acceptable salt thereof, wherein n is 1 and $R^1$ is —$OR_3$. In another embodiment is a compound of Formula (II), or a solvate, N-oxide, stereoisomer, or pharmaceutically acceptable salt thereof, wherein n is 1, $R^1$ is —$OR^3$, and $R^3$ is $C_{1-6}$haloalkyl. In another embodiment is a compound of Formula (II), or a solvate, N-oxide, stereoisomer, or pharmaceutically acceptable salt thereof, wherein n is 1 and $R^1$ is —$OCF_3$. In another embodiment is a compound of Formula (II), or a solvate, N-oxide, stereoisomer, or pharmaceutically acceptable salt thereof, wherein n is 1, $R^1$ is —$OR^3$, and $R^3$ is phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and $C(O)OR^4$. In another embodiment is a compound of Formula (II), or a solvate, N-oxide, stereoisomer, or pharmaceutically acceptable salt thereof, wherein n is 1, $R^1$ is —$OR^3$, and $R^3$ is phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is phenyl substituted with 1 substituent selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is -$C_{1-6}$alkyl-phenyl optionally substituted with 1 or 2 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and $C(O)OR^4$. In another embodiment is a compound of Formula (II), or a solvate, N-oxide, stereoisomer, or pharmaceutically acceptable salt thereof, wherein n is 1, $R^1$ is —$OR^3$, and $R^3$ is -$C_{1-6}$alkyl-phenyl optionally substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 1 or 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 2 substituents independently selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1, $R^1$ is —$OR^3$, and $R^3$ is -$C_{1-6}$alkyl-phenyl substituted with 1 substituent selected from halogen, $C_{1-6}$haloalkyl, and $C_{1-6}$haloalkoxy. In another embodiment is a compound of Formula (II), or a solvate, N-oxide, stereoisomer, or pharmaceutically acceptable salt thereof, wherein n is 1 and $R^1$ is phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 and $R^1$ is phenyl substituted with 1 or 2 substituents independently selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 and $R^1$ is phenyl substituted with 1 substituent selected from halogen, $C_{1-6}$alkyl, $C_{1-6}$haloalkyl, $C_{1-6}$alkoxy, and $C_{1-6}$haloalkoxy. In another embodiment is a compound of Formula (II), or a solvate, N-oxide, stereoisomer, or pharmaceutically acceptable salt thereof, wherein n is 1 and $R^1$ is phenyl substituted with 2 substituents independently selected from halogen, $C_{1-6}$alkyl, $C_{1-6}$haloalkyl, $C_{1-6}$alkoxy, and $C_{1-6}$haloalkoxy.

Further embodiments provided herein include combinations of one or more of the particular embodiments set forth above.

In some embodiments, the compound disclosed herein is selected from:

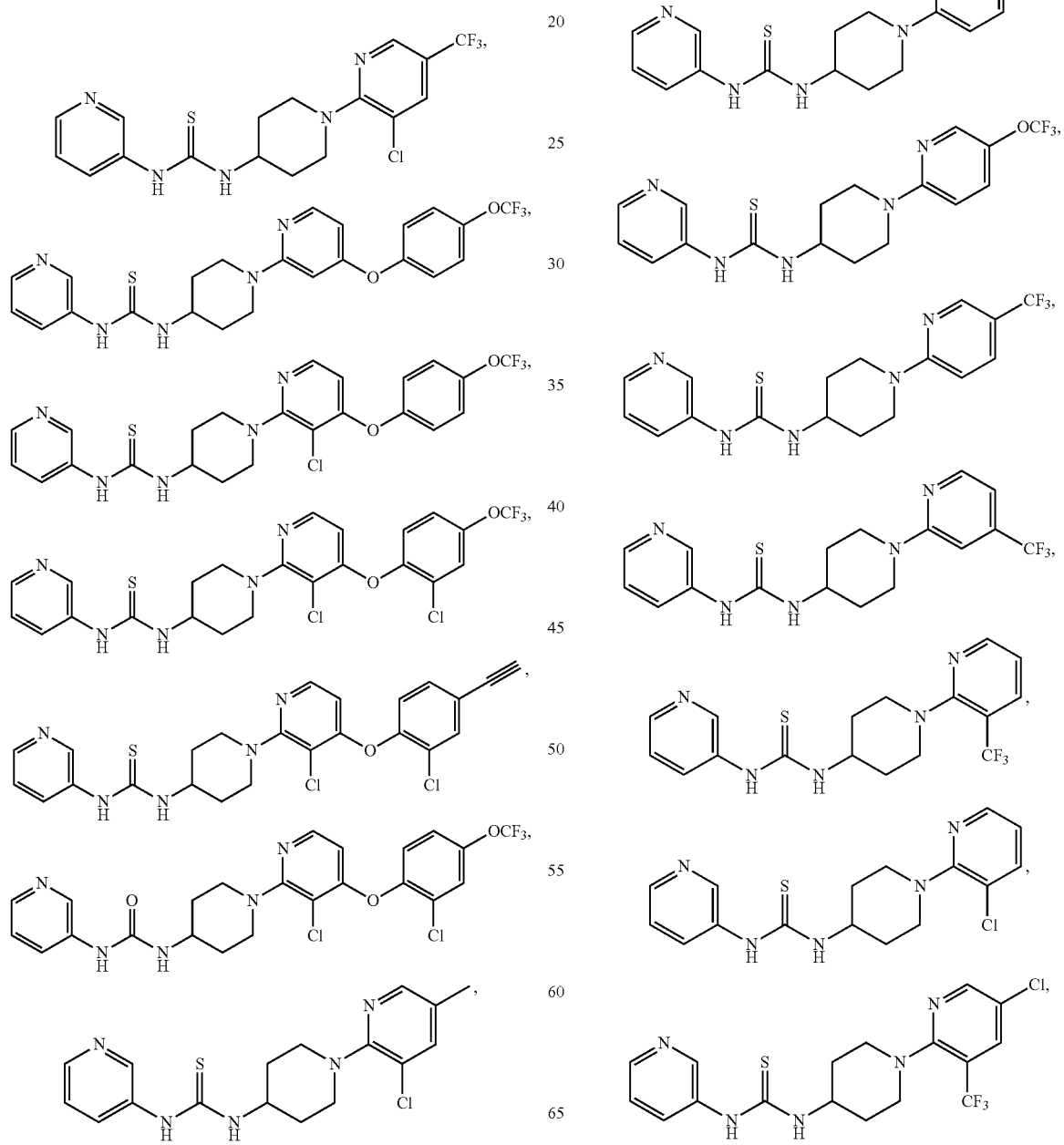

-continued
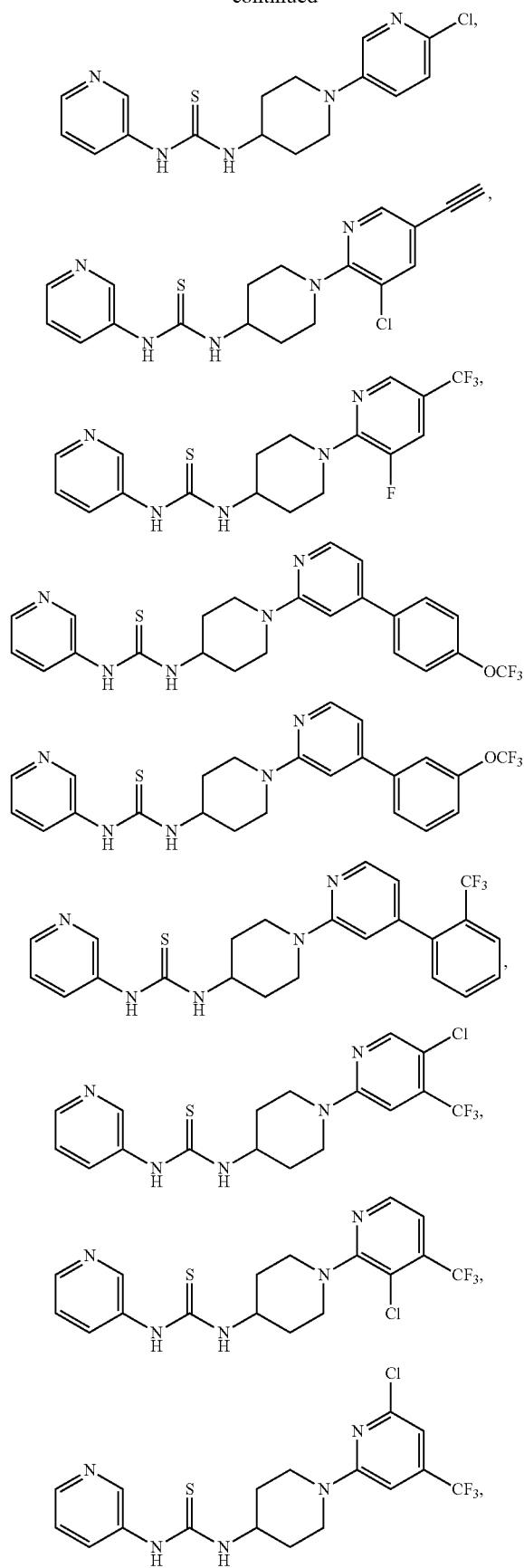
-continued
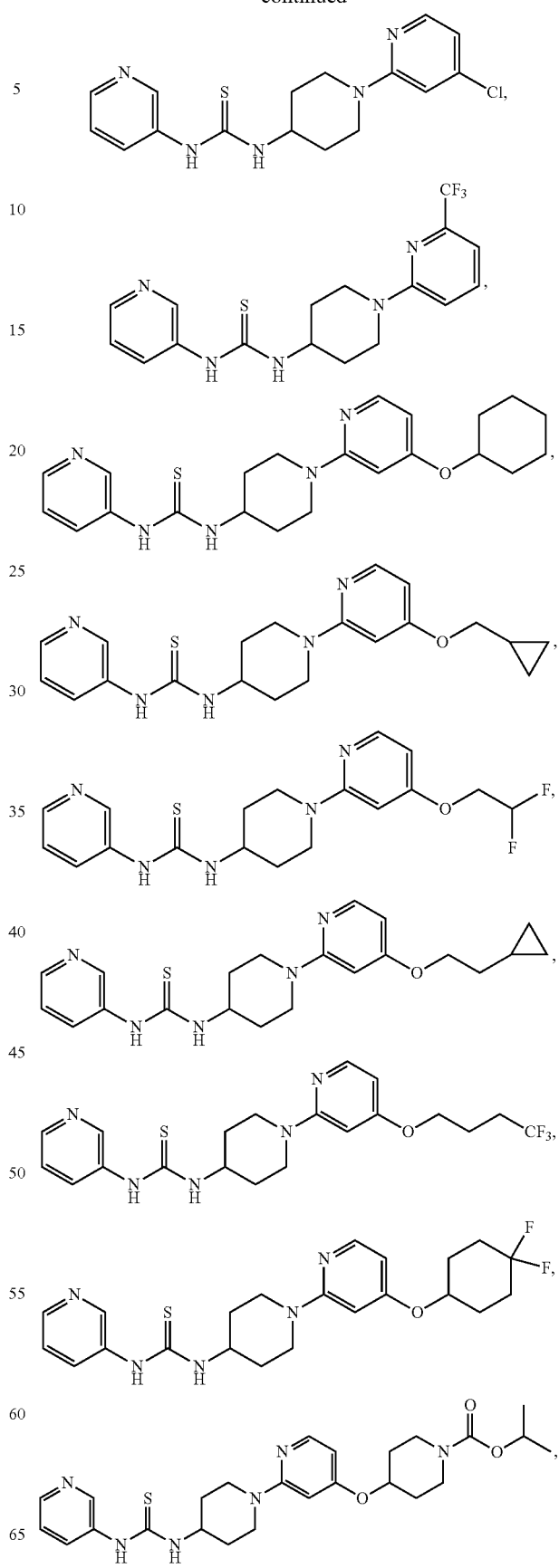

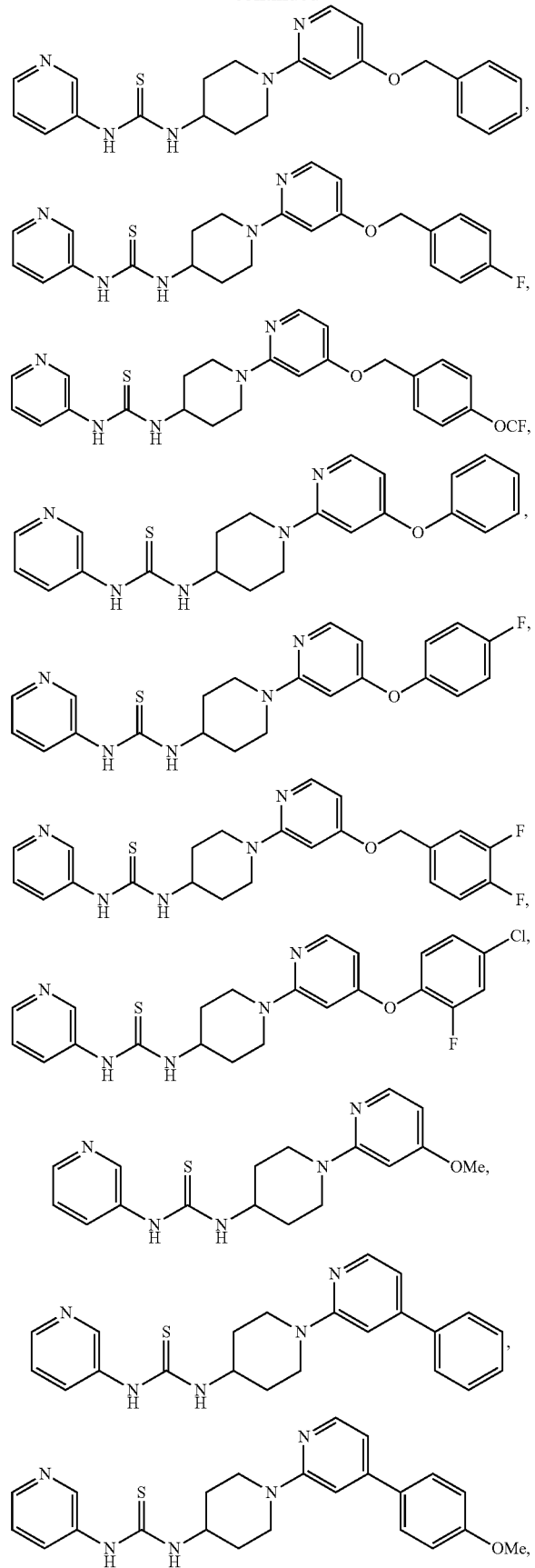
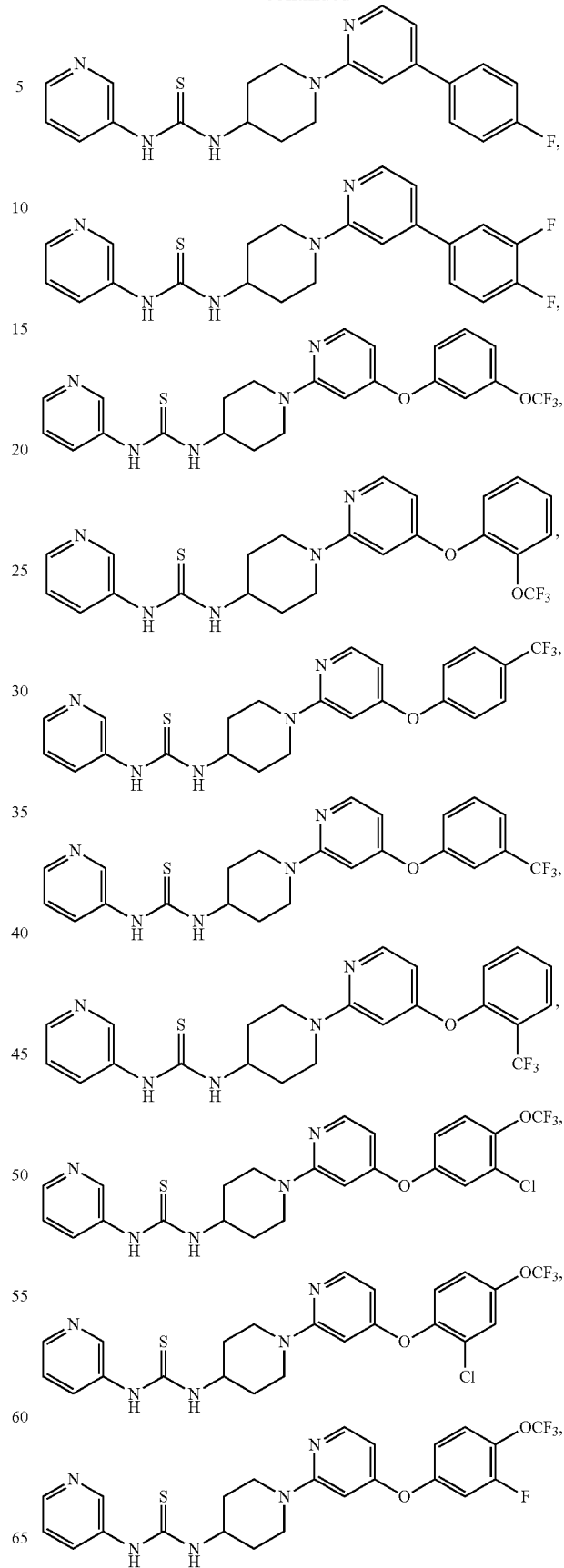

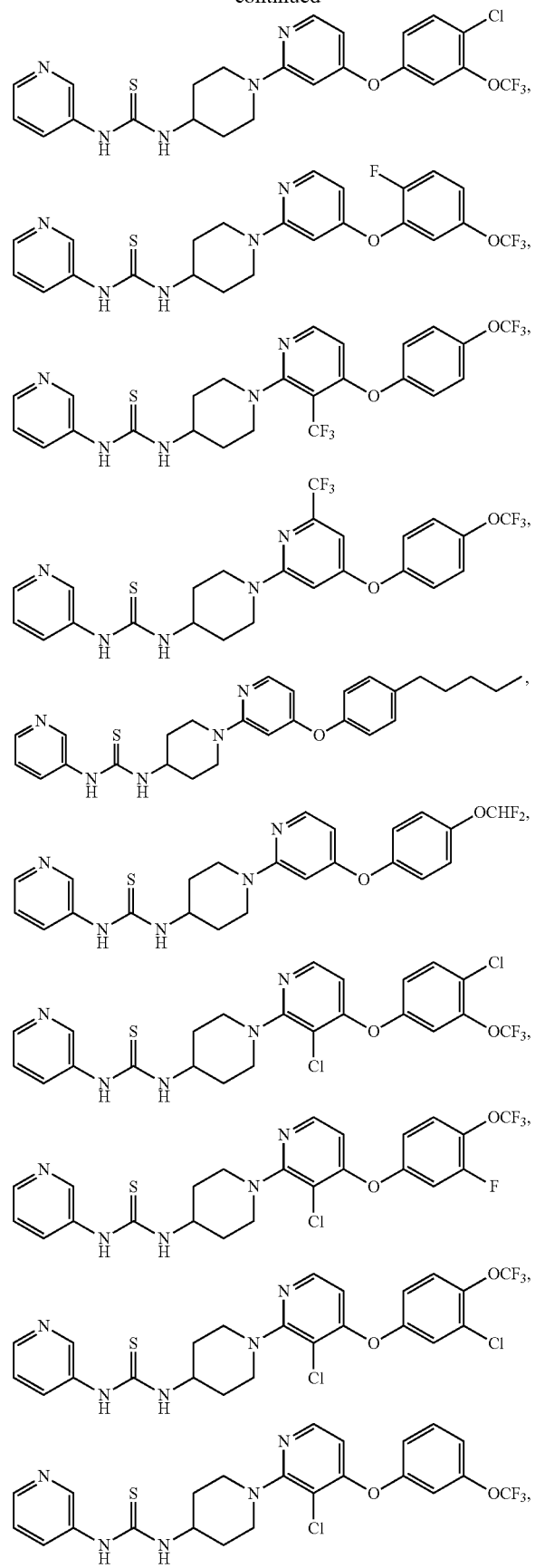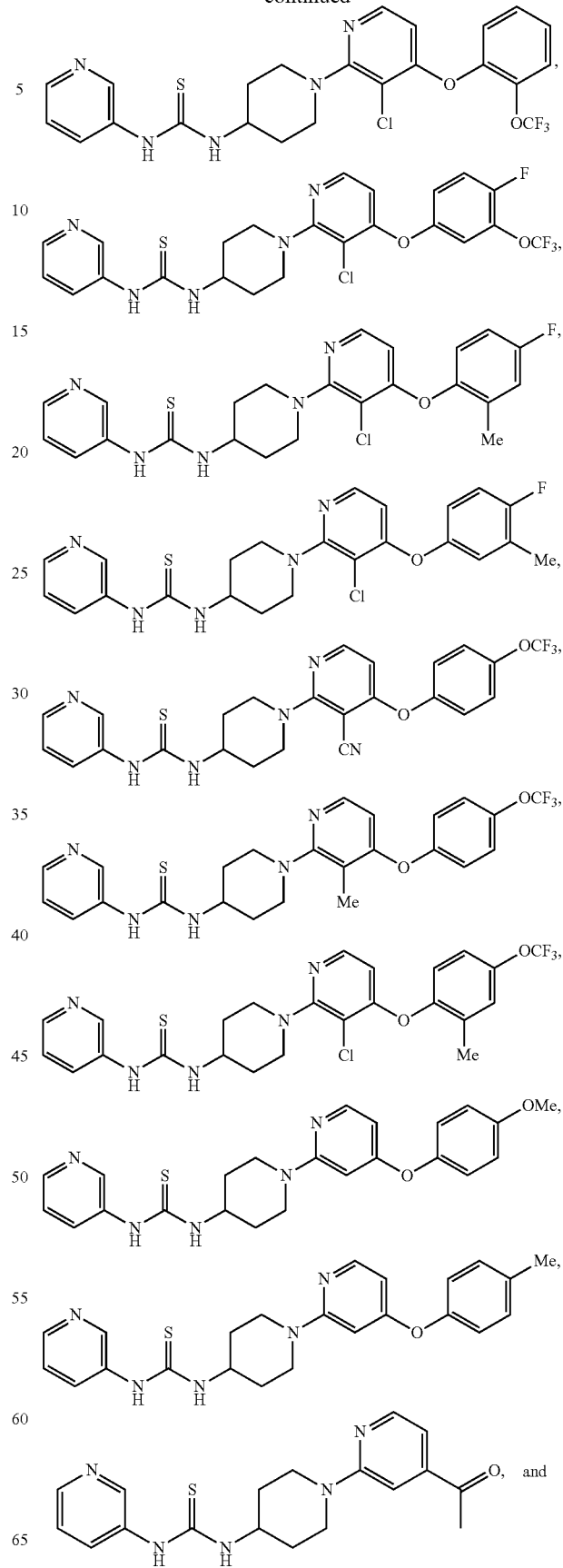

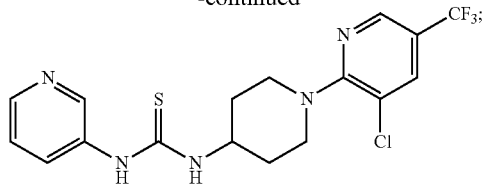
or a solvate, N-oxide, stereoisomer, or pharmaceutically acceptable salt thereof.
In some embodiments, the compound disclosed herein is selected from:
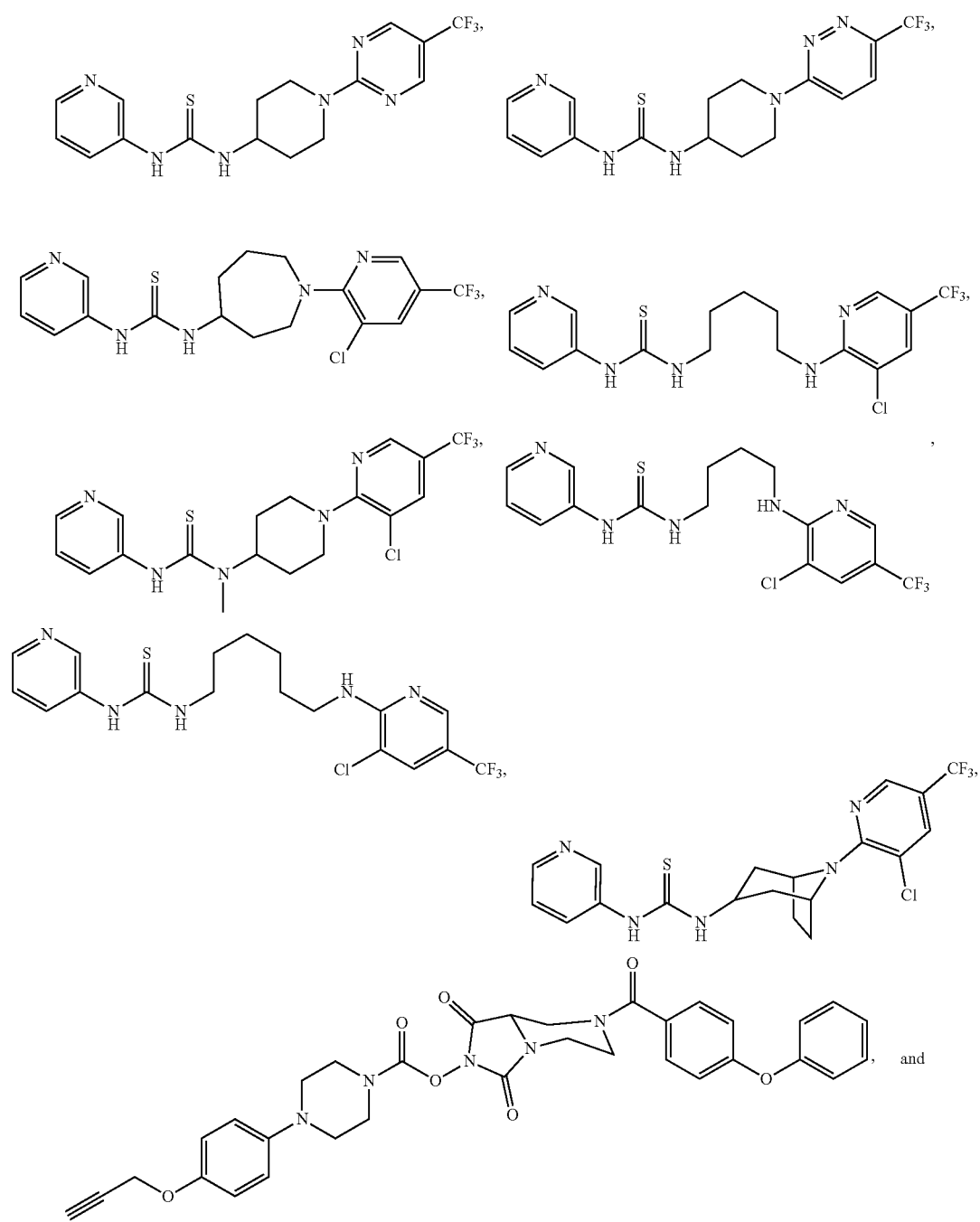

-continued

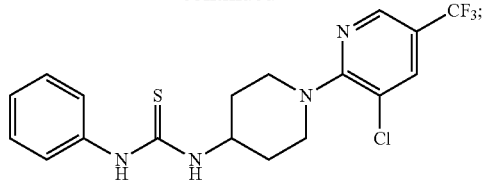

or a solvate, N-oxide, stereoisomer, or pharmaceutically acceptable salt thereof Preparation of Compounds The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, WI, including Sigma Chemical and Fluka), Apin Chemicals Ltd. (Milton Park, UK), Ark Pharm, Inc. (Libertyville, IL), Avocado Research (Lancashire, U.K.), BDH Inc. (Toronto, Canada), Bionet (Cornwall, U.K.), Chemservice Inc. (West Chester, PA), Combi-blocks (San Diego, CA), Crescent Chemical Co. (Hauppauge, NY), eMolecules (San Diego, CA), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Matrix Scientific, (Columbia, SC), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Ryan Scientific, Inc. (Mount Pleasant, SC), Spectrum Chemicals (Gardena, CA), Sundia Meditech, (Shanghai, China), TCI America (Portland, OR), Trans World Chemicals, Inc. (Rockville, MD), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compound of Formula (I) or (II) described herein is administered as a pure chemical. In some embodiments, the compound of Formula (I) or (II) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Accordingly, provided herein is a pharmaceutical composition comprising at least one compound of Formula (I) or (II) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (II), or a pharmaceutically acceptable salt thereof.

Another embodiment provides a pharmaceutical composition consisting essentially of a pharmaceutically acceptable excipient and a compound of Formula (II), or a pharmaceutically acceptable salt thereof.

In certain embodiments, the compound of Formula (I) or (II) described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients.

In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches, and inhalants. In some embodiments, the active component is mixed under sterile conditions with a pharmaceutically acceptable carrier, and with any preservatives, buffers, or propellants as required.

In some embodiments, the ointments, pastes, creams, and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, and amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5, and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I) or (II) described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of ABHD12. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I) or (II). In some embodiments, provided herein is a compound of Formula (I) or (II) wherein the compound is an ABHD12 inhibitor. In some embodiments, provided herein is a compound of Formula (I) or (II) wherein the compound is a selective ABHD12 inhibitor. The ability of compounds described herein to modulate or inhibit ABHD12 is evaluated by procedures known in the art and/or described herein. Another aspect of this disclosure provides methods of treating a disease associated with expression or activity of ABHD12 in a patient. In some embodiments, provided herein is a compound of Formula (I) or (II) wherein the compound is selective in inhibiting ABHD12 as compared to inhibition of other serine hydrolases. In some embodiments, provided herein is a compound of Formula (I) or (II) wherein the compound is 10, 100, or 1000 fold selective in inhibiting ABHD12 as compared to inhibition of other serine hydrolases.

In another embodiment is a method of treating a disease or disorder in a patient in need thereof, comprising administering to the patient a therapeutically effective amount of a compound of Formula (I) or (II) described herein, or a solvate, hydrate, tautomer, N-oxide, or a pharmaceutically acceptable salt thereof, wherein the disease or disorder is a neuropsychiatric disorder, an autoimmune disease, a neuroinflammatory disease, a neurodegenerative disease, or cancer. In another embodiment is a method of treating a neuropsychiatric disorder in a patient in need thereof, comprising administering to the patient a therapeutically effective amount of a compound of Formula (I) or (II) described herein, or a solvate, hydrate, tautomer, N-oxide, or a pharmaceutically acceptable salt thereof. In another embodiment is a method of treating an autoimmune disease in a patient in need thereof, comprising administering to the patient a therapeutically effective amount of a compound of Formula (I) or (II) described herein, or a solvate, hydrate, tautomer, N-oxide, or a pharmaceutically acceptable salt thereof. In another embodiment is a method of treating a neuroinflammatory disease in a patient in need thereof, comprising administering to the patient a therapeutically effective amount of a compound of Formula (I) or (II) described herein, or a solvate, hydrate, tautomer, N-oxide, or a pharmaceutically acceptable salt thereof. In another embodiment is a method of treating a neurodegenerative disease in a patient in need thereof, comprising administering to the patient a therapeutically effective amount of a compound of Formula (I) or (II) described herein, or a solvate, hydrate, tautomer, N-oxide, or a pharmaceutically acceptable salt thereof. In another embodiment is a method of treating cancer in a patient in need thereof, comprising administering to the patient a therapeutically effective amount of a compound of Formula (I) or (II) described herein, or a solvate, hydrate, tautomer, N-oxide, or a pharmaceutically acceptable salt thereof.

In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein the compound is an immunotherapeutic agent.

In some embodiments, a compound of Formula (I) or (II) described herein stimulates a patient's immune system to treat a disease. In some embodiments is a method of treating a disease in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system. In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system. In another embodiment is a method of treating cancer in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound initiates an immune response.

In another embodiment is a method of treating an infectious disease in a patient in need thereof, comprising administering to the patient a therapeutically effective amount of a compound of Formula (I) or (II), or a solvate, N-oxide, stereoisomer, or pharmaceutically acceptable salt thereof, wherein the compound is an immunotherapeutic agent.

In another embodiment is a method of treating an infectious disease in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system. In another embodiment is a method of treating an infectious disease in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound stimulates the patient's immune system. In another embodiment is a method of treating an infectious disease in a patient in need thereof, comprising administering to the patient a therapeutically effective amount of a compound of Formula (I) or (II), or a solvate, N-oxide, stereoisomer, or pharmaceutically acceptable salt thereof, wherein administration of the compound initiates an immune response.

In certain embodiments, a disclosed compound utilized by one or more of the foregoing methods is one of the generic, subgeneric, or specific compounds described herein, such as a compound of Formula (I) or (II).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration includes subcutaneous injections, intravenous, or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 1-(1-(3-Chloro-5-(trifluoromethyl)pyridin-2-yl)piperidin-4-yl)-3-(pyridin-3-yl)thiourea

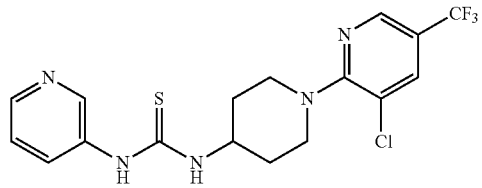 [SMILES: FC(F)(F)c1cnc(N2CCC(NC(=S)Nc3cccnc3)CC2)c(Cl)c1]

Step 1: Preparation of t-butyl (1-(3-chloro-5-(trifluoromethyl)pyridin-2-yl)piperidin-4-yl)carbamate

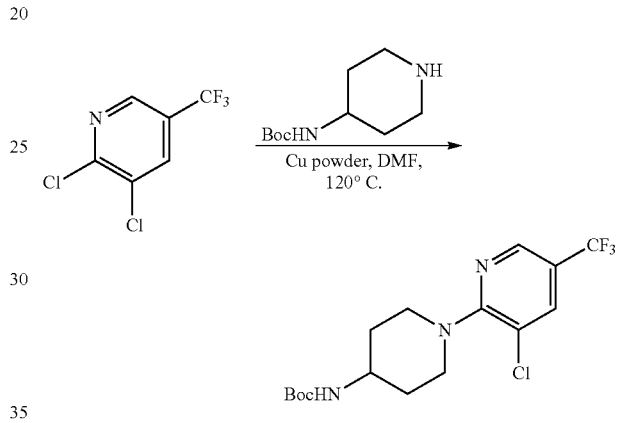

A solution of 2,3-dichloro-5-(trifluoromethyl)pyridine (11) (1.0 g, 4.6 mmol), t-butyl(piperidin-4-yl)carbamate, (0.93 g, 4.6 mmol) and Cu powder (40 mg) in dry DMF (2.5 mL) was stirred for 30 min at 120° C. The mixture was diluted with DCM and washed with water and brine. The organic layer was dried over $Na_2SO_4$ and concentrated under reduced pressure. The residue was purified by flash column chromatography to afford t-butyl (1-(3-chloro-5-(trifluoromethyl)pyridin-2-yl)piperidin-4-yl)carbamate (800 mg, 46%) as a white solid. $^1$H NMR ($CDCl_3$, 600 MHz) δ 8.35 (s, 1H), 7.72 (s, 1H), 4.54 (s, 1H), 3.97-3.93 (m, 2H), 3.69 (s, 1H), 3.00 (ddd, 2H, J=12.4, 11.5, 2.5 Hz), 2.06-2.02 (m, 2H), 1.54 (dtd, 2H, J=12.7, 11.1, 3.9 Hz), 1.44 (s, 9H).

Step 2: Preparation of t-butyl (1-(3-chloro-5-(trifluoromethyl)pyridin-2-yl)piperidin-4-yl)carbamate

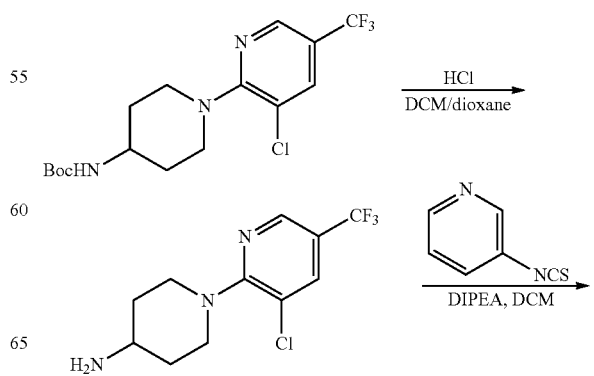

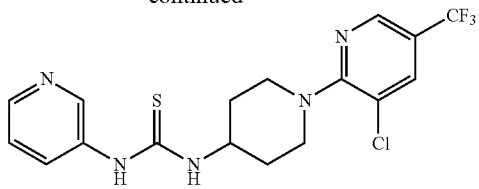

To a solution of t-butyl (1-(3-chloro-5-(trifluoromethyl) pyridin-2-yl)piperidin-4-yl)carbamate (50 mg, 0.13 mmol) in DCM (0.5 mL) was added dropwise 4N HCl in dioxane (0.5 mL). The mixture was stirred for 2 h at room temperature and dried under $N_2$ stream to provide 1-(3-chloro-5-(trifluoromethyl)pyridin-2-yl)piperidin-4-amine. The crude material was dissolved in DCM (1 mL). DIPEA (90 µL, 0.51 mmol) and 3-pyridineisothiocyanate (19 mg, 0.14 mmol) were added and the mixture was stirred for 3 h at room temperature, diluted with DCM and washed with sat. $NaHCO_3$. The organic layer was dried over $Na_2SO_4$ and concentrated under reduced pressure. The residue was purified by preparative TLC to afford t-butyl (1-(3-chloro-5-(trifluoromethyl)pyridin-2-yl)piperidin-4-yl)carbamate (50 mg, 94%) as a white solid. $^1$H NMR (CDCl$_3$, 600 MHz) δ 8.56 (dd, 1H, J=4.8, 1.5 Hz), 8.54 (dd, 1H, J=2.6, 0.8 Hz), 8.37-8.36 (m, 1H), 7.74 (d, 1H, J=2.2 Hz), 7.66 (s, 1H), 7.61 (dt, 1H, J=8.3, 2.2 Hz), 7.40 (dd, 1H, J=8.1, 4.7, 0.8 Hz), 5.77 (d, 1H, J=8.1 Hz), 4.60-4.54 (1H, m), 4.00 (d, 2H, J=13.7 Hz), 3.07 (ddd, 2H, J=13.7, 11.6, 2.5 Hz), 2.25-2.21 (m, 2H), 1.60-1.54 (m, 2H). HRMS calculated for $C_{17}H_{17}ClF_3N_5S$ [M+H]$^+$ 416.0924, found 416.0928.

Example 2: 1-(Pyridin-3-yl)-3-(1-(4-(4-(trifluoromethoxy)phenoxy)pyridin-2-yl)piperidin-4-yl) thiourea

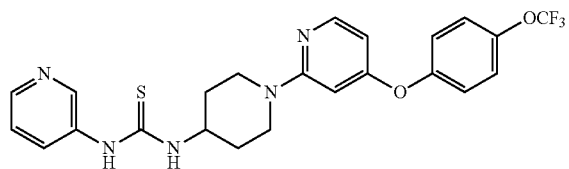 [SMILES: FC(F)(F)Oc1ccc(Oc2ccnc(N3CCC(NC(=S)Nc4cccnc4)CC3)c2)cc1]

Step 1: Preparation of 2-chloro-4-(4-(trifluoromethoxy)phenoxy)pyridine

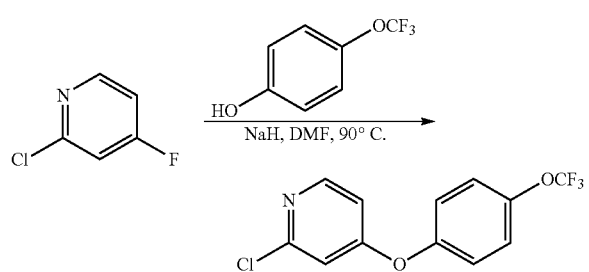

To a solution of 4-trifluoromethoxyphenol (406 mg, 2.3 mmol) in dry DMF (1.0 mL) was slowly added 60% sodium hydride in mineral oil (91 mg, 2.3 mmol) at 0° C. The mixture was warmed to room temperature and stirred for 20 min. The reaction mixture was cooled to 0° C. and 2-chloro-4-fluoropyridine (300 mg, 2.3 mmol) was added. The reaction mixture was stirred overnight at 90° C. and concentrated under reduced pressure. The residue was purified by flash column chromatography to afford 2-chloro-4-(4-(trifluoromethoxy)phenoxy)pyridine (580 mg, 88%) as a colorless oil. $^1$H NMR (CDCl$_3$, 600 MHz) δ 8.23 (d, 1H, J=5.7 Hz), 7.31-7.28 (m, 2H), 7.14-7.11 (m, 2H), 6.83 (d, 1H, J=2.2 Hz), 6.79 (dd, 1H, J=5.7, 2.2 Hz). HRMS calculated for $C_{12}H_7ClF_3NO_2$ [M+H]$^+$ 290.0196, found 290.0198.

Step 2: Preparation of t-butyl (1-(4-(4-(trifluoromethoxy)phenoxy)pyridin-2-yl)piperidin-4-yl)carbamate

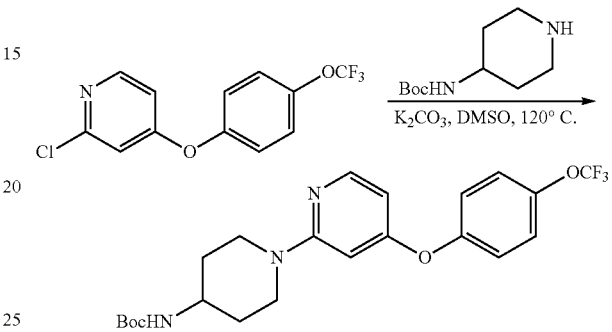

A solution of 2-chloro-4-(4-(trifluoromethoxy)phenoxy)pyridine (500 mg, 1.7 mmol), t-butyl(piperidin-4-yl)carbamate (1.38 g, 6.9 mmol) and potassium carbonate (360 mg, 2.6 mmol) in dry DMSO (0.85 mL) was stirred for 12 h at 120° C. The mixture was dissolved in DCM and filtered through a pad of silica with EtOAc. The eluent was concentrated under reduced pressure and the residue was purified by flash column chromatography to afford t-butyl (1-(4-(4-(trifluoromethoxy)phenoxy)pyridin-2-yl)piperidin-4-yl)carbamate (390 mg, 50%) as a white solid. $^1$H NMR (CDCl$_3$, 600 MHz) δ 8.00 (d, J=5.7 Hz, 1H), 7.18 (d, J=8.7 Hz, 2H), 7.05-7.02 (m, 2H), 6.17 (d, J=2.1 Hz, 1H), 6.12 (dd, J=5.7, 2.0 Hz, 1H), 4.60 (d, J=8.0 Hz, 1H), 4.10 (dt, J=13.8, 3.9 Hz, 2H), 3.64 (d, J=10.2 Hz, 1H), 2.91 (ddd, J=13.9, 11.6, 2.8 Hz, 2H), 1.96 (d, J=13.0 Hz, 2H), 1.41 (s, 9H), 1.40-1.33 (m, 2H). HRMS calculated for $C_{22}H_{26}F_3N_3O_4$ [M+H]$^+$ 454.1954, found 454.1957.

Step 3: Preparation of 1-(pyridin-3-yl)-3-(1-(4-(4-(trifluoromethoxy)phenoxy)pyridin-2-yl)piperidin-4-yl)thiourea

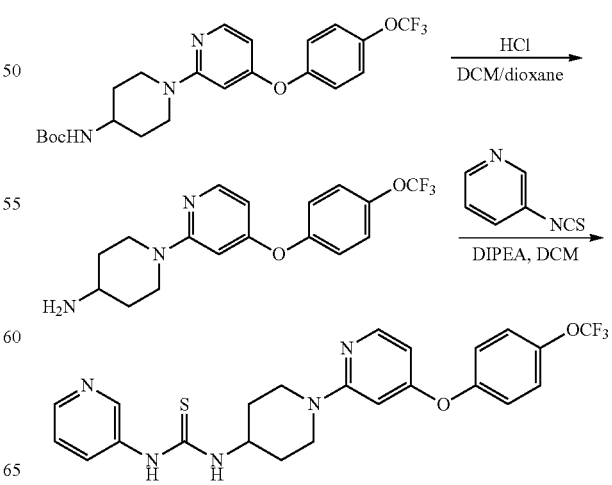

1-(Pyridin-3-yl)-3-(1-(4-(4-(trifluoromethoxy)phenoxy)pyridin-2-yl)piperidin-4-yl)thiourea was prepared from t-butyl (1-(4-(4-(trifluoromethoxy)phenoxy)pyridin-2-yl)piperidin-4-yl)carbamate, HCl, and 3-pyridineisothiocyanate as described in Example 1, Step 2 in 86% yield. $^1$H NMR (CDCl$_3$, 600 MHz) δ 8.56 (s, 1H), 8.46 (d, J=2.6 Hz, 1H), 8.43 (dd, J=4.8, 1.5 Hz, 1H), 8.02 (d, J=5.7 Hz, 1H), 7.73 (dt, J=8.6, 1.8 Hz, 1H), 7.32 (ddd, J=8.2, 4.8, 0.7 Hz, 1H), 7.23-7.21 (m, 2H), 7.08-7.05 (m, 2H), 6.21 (s, 1H), 6.19 (d, J=2.1 Hz, 1H), 6.15 (dd, J=5.7, 2.0 Hz, 1H), 4.53 (s, 1H), 4.15-4.11 (m, 2H), 2.99 (ddd, J=13.9, 11.6, 2.7 Hz, 2H), 2.16-2.12 (m, 2H), 1.40 (qd, J=11.7, 4.1 Hz, 2H). HRMS calculated for C$_{23}$H$_{22}$F$_3$N$_5$O$_2$S [M+H]$^+$ 490.1525, found 490.1528.

Example 3: 1-(1-(3-chloro-4-(4-(trifluoromethoxy)phenoxy)pyridin-2-yl)piperidin-4-yl)-3-(pyridin-3-yl)thiourea

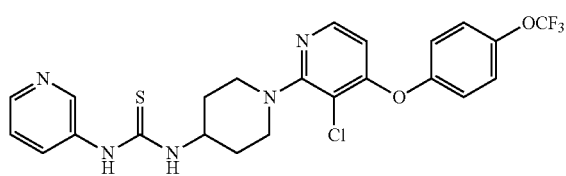 [SMILES: FC(F)(F)Oc1ccc(Oc2ccnc(N3CCC(NC(=S)Nc4cccnc4)CC3)c2Cl)cc1]

Step 1: Preparation of 2,3-dichloro-4-(4-(trifluoromethoxy)phenoxy)pyridine

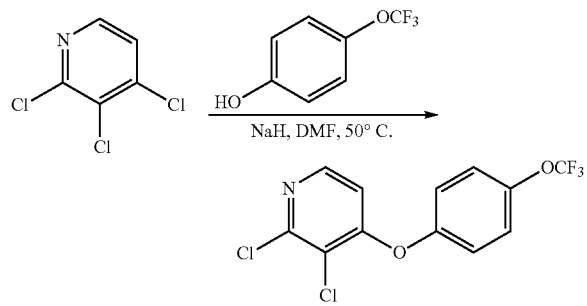

2,3-Dichloro-4-(4-(trifluoromethoxy)phenoxy)pyridine was prepared from 4-trifluoromethoxyphenol and 2,3,4-trichloropyridine as described in Example 2, Step 1 in 96% yield. $^1$H NMR (CDCl$_3$, 600 MHz) δ 8.09 (d, 1H, J=5.6 Hz), 7.31-7.28 (m, 2H), 7.15-7.12 (m, 2H), 6.61 (d, 1H, J=5.5 Hz). HRMS calculated for C$_{12}$H$_6$Cl$_2$F$_3$NO$_2$ [M+H]$^+$ 323.9806, found 323.9813.

Step 2: Preparation of t-butyl (1-(3-chloro-4-(4-(trifluoromethoxy)phenoxy)pyridin-2-yl)piperidin-4-yl)carbamate

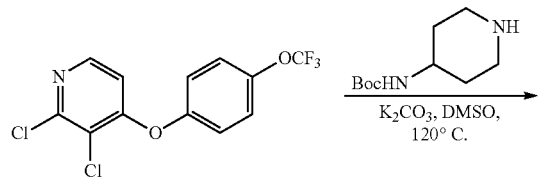

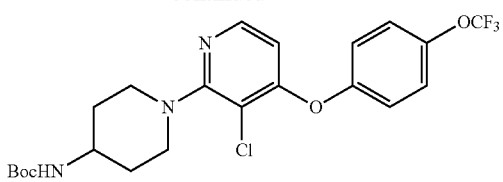

t-Butyl (1-(3-chloro-4-(4-(trifluoromethoxy)phenoxy)pyridin-2-yl)piperidin-4-yl)carbamate was prepared from 2,3-dichloro-4-(4-(trifluoromethoxy)phenoxy)pyridine and t-butyl(piperidin-4-yl)carbamate as described in Example 2, Step 2 in 63% yield. $^1$H NMR (CDCl$_3$, 600 MHz) δ 8.00 (d, J=5.6 Hz, 1H), 7.24 (d, J=8.5 Hz, 2H), 7.09-7.06 (m, 2H), 6.33 (d, J=5.6 Hz, 1H), 4.56-4.51 (m, 1H), 3.78 (d, J=13.0 Hz, 2H), 3.68 (s, 1H), 2.97 (ddd, J=13.4, 11.3, 2.5 Hz, 2H), 2.06 (d, J=12.1 Hz, 2H), 1.59 (dtd, J=12.6, 11.0, 3.9 Hz, 2H), 1.45 (s, 9H). HRMS calculated for C$_{22}$H$_{25}$ClF$_3$N$_3$O$_4$ [M+H]$^+$ 488.1564, found 488.1571.

Step 3: Preparation of 1-(1-(3-chloro-4-(4-(trifluoromethoxy)phenoxy)pyridin-2-yl)piperidin-4-yl)-3-(pyridin-3-yl)thiourea

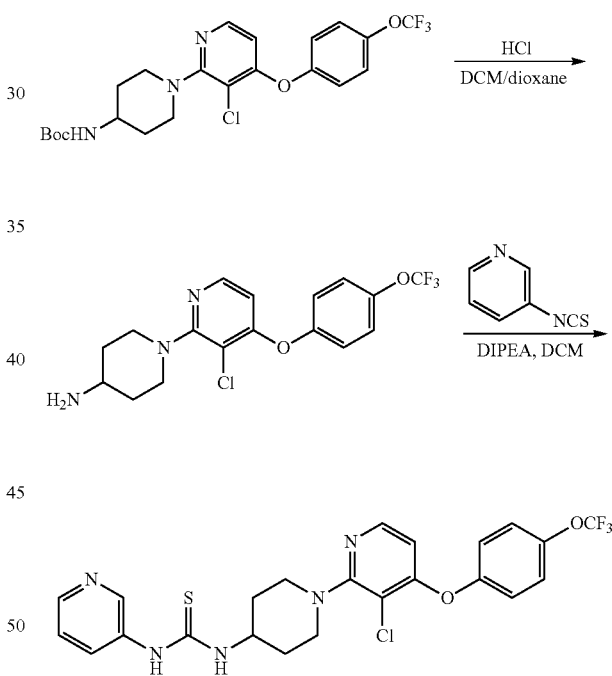

1-(1-(3-Chloro-4-(4-(trifluoromethoxy)phenoxy)pyridin-2-yl)piperidin-4-yl)-3-(pyridin-3-yl)thiourea was prepared from t-butyl (1-(3-chloro-4-(4-(trifluoromethoxy)phenoxy)pyridin-2-yl)piperidin-4-yl)carbamate, HCl, and 3-pyridineisothiocyanate as described in Example 1, Step 2 in 68% yield. $^1$H NMR (DMSO-d$_6$, 600 MHz) δ 9.49 (s, 1H), 8.57 (d, J=2.5 Hz, 1H), 8.28 (d, J=4.7 Hz, 1H), 8.10 (dd, J=5.5, 1.1 Hz, 1H), 8.05 (s, 1H), 7.97 (d, J=7.8 Hz, 1H), 7.46 (d, J=8.5 Hz, 2H), 7.34 (dd, J=8.3, 4.7 Hz, 1H), 7.29-7.26 (m, 2H), 6.50 (d, J=5.5 Hz, 1H), 4.37 (s, 1H), 3.74 (d, J=12.5 Hz, 2H), 2.97 (t, J=11.8 Hz, 2H), 2.06 (d, J=8.7 Hz, 2H), 1.68 (q, J=10.6, 2H). HRMS calculated for C$_{23}$H$_{21}$ClF$_3$N$_5$O$_2$S [M+H]$^+$ 524.1135, found 524.1138.

Example 4: 1-(1-(3-Chloro-4-(2-chloro-4-(trifluoromethoxy)phenoxy)pyridin-2-yl)piperidin-4-yl)-3-(pyridin-3-yl)thiourea

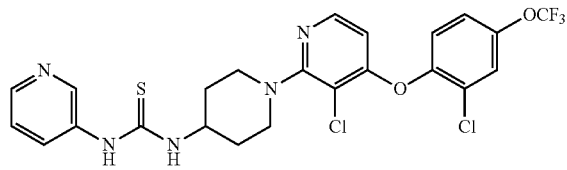 [SMILES: FC(F)(F)Oc1ccc(Oc2ccnc(N3CCC(NC(=S)Nc4cccnc4)CC3)c2Cl)c(Cl)c1]

Step 1: Preparation of 2,3-dichloro-4-(2-chloro-4-(trifluoromethoxy)phenoxy)pyridine

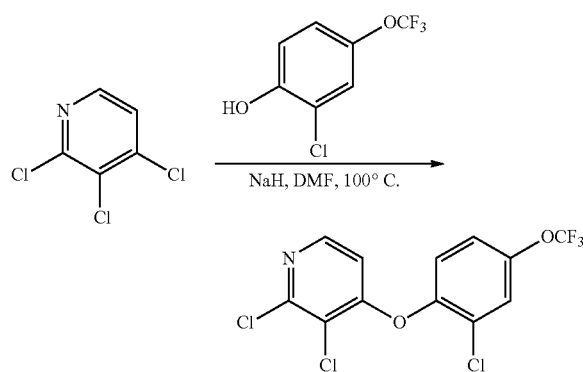

2,3-Dichloro-4-(2-chloro-4-(trifluoromethoxy)phenoxy)pyridine was prepared from 2-chloro-4-trifluoromethoxyphenol and 2,3,4-trichloropyridine (1.5 g, 8.3 mmol) as described in Example 2, Step 1 in 82% yield. $^1$H NMR (CDCl$_3$, 600 MHz) δ 8.12 (d, 1H, J=5.6 Hz), 7.43 (dt, 1H, J=2.6, 0.8 Hz), 7.26-7.22 (m, 2H), 6.45 (d, 1H, J=5.6 Hz). HRMS calculated for C$_{12}$H$_5$Cl$_3$F$_3$NO$_2$ [M+H]$^+$ 357.9416, found 357.9422.

Step 2: Preparation of t-butyl (1-(3-chloro-4-(2-chloro-4-(trifluoromethoxy)phenoxy)pyridin-2-yl)piperidin-4-yl)(methyl)carbamate

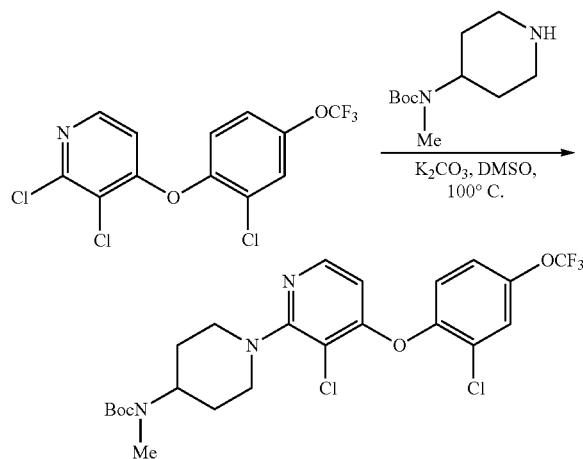

t-Butyl (1-(3-chloro-4-(2-chloro-4-(trifluoromethoxy)phenoxy)pyridin-2-yl)piperidin-4-yl)(methyl)carbamate was prepared from 2,3-dichloro-4-(2-chloro-4-(trifluoromethoxy)phenoxy)pyridine and N-methyl-t-butyl(piperidin-4-yl)carbamate as described in Example 2, Step 2 in 39% yield. $^1$H NMR (CDCl$_3$, 600 MHz) δ 8.00 (d, J=5.5 Hz, 1H), 7.39 (d, J=2.7 Hz, 1H), 7.19-7.17 (m, 1H), 7.12 (d, J=8.9 Hz, 1H), 6.17 (d, J=5.6 Hz, 1H), 4.24-3.94 (m, 3H), 2.92 (t, J=11.7 Hz, 2H), 2.79 (s, 3H), 1.92-1.86 (m, 2H), 1.76 (ddd, J=11.7, 4.4, 2.0 Hz, 2H), 1.48 (s, 9H). HRMS calculated for C$_{23}$H$_{26}$Cl$_2$F$_3$N$_3$O$_4$ [M+H]$^+$ 536.1331, found 536.1334.

Step 3: Preparation of 1-(1-(3-chloro-4-(2-chloro-4-(trifluoromethoxy)phenoxy)pyridin-2-yl)piperidin-4-yl)-3-(pyridin-3-yl)thiourea

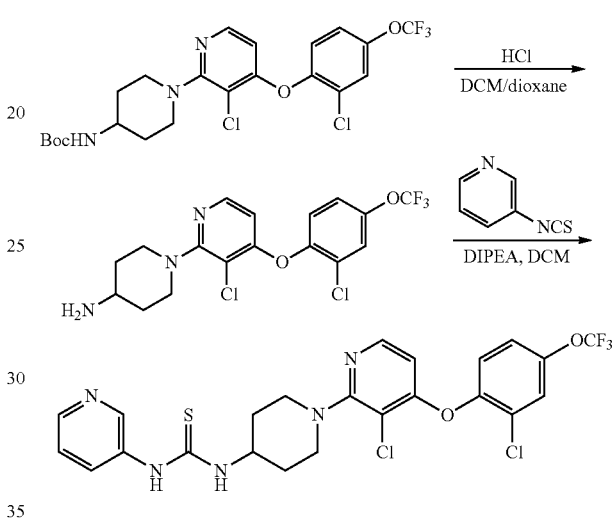

1-(1-(3-Chloro-4-(2-chloro-4-(trifluoromethoxy)phenoxy)pyridin-2-yl)piperidin-4-yl)-3-(pyridin-3-yl)thiourea was prepared from t-butyl (1-(3-chloro-4-(2-chloro-4-(trifluoromethoxy)phenoxy)pyridin-2-yl)piperidin-4-yl)(methyl)carbamate, HCl and 3-pyridineisothiocyanate as described in Example 1, Step 2 in 76% yield. $^1$H NMR (CDCl$_3$, 600 MHz) δ 8.56-8.55 (m, 2H), 7.98 (d, J=5.6 Hz, 1H), 7.84 (s, 1H), 7.64 (d, J=8.3 Hz, 0H), 7.41-7.38 (m, 2H), 7.18 (ddd, J=9.0, 2.8, 0.9 Hz, 1H), 7.12 (d, J=8.9 Hz, 1H), 6.17 (d, J=5.6 Hz, 1H), 5.87 (d, J=7.9 Hz, 1H), 4.55 (s, 1H), 3.82 (d, J=12.9 Hz, 2H), 3.05 (ddd, J=13.5, 11.4, 2.5 Hz, 2H), 2.26-2.22 (m, 2H), 1.66-1.60 (m, 2H). HRMS calculated for C$_{23}$H$_{20}$Cl$_2$F$_3$N$_5$O$_2$S [M+H]$^+$ 558.0745, found 558.0751.

Example 5: 1-(1-(3-Chloro-4-(2-chloro-4-ethynylphenoxy)pyridin-2-yl)piperidin-4-yl)-3-(pyridin-3-yl)thiourea

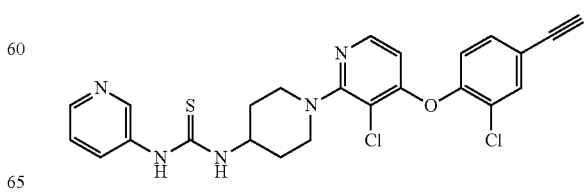

Step 1: Preparation of 2,3-dichloro-4-(2-chloro-4-iodophenoxy)pyridine

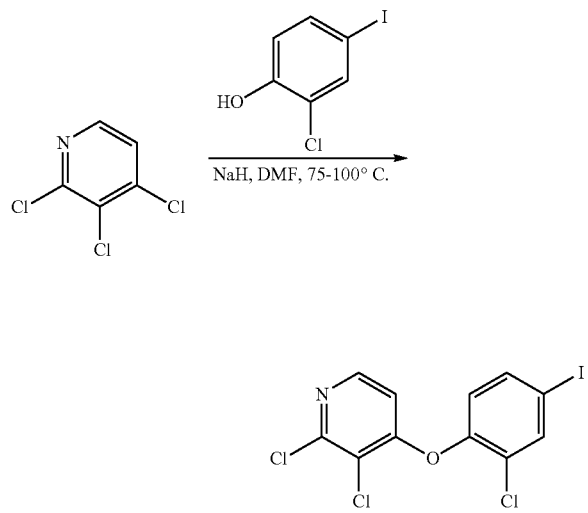

2,3-Dichloro-4-(2-chloro-4-iodophenoxy)pyridine was prepared from 2-chloro-4-iodophenol and 2,3,4-trichloropyridine (500 mg, 2.8 mmol) as described in Example 2, Step 1 in 78% yield. $^1$H NMR (CDCl$_3$, 600 MHz) δ 8.10 (d, J=5.5 Hz, 1H), 7.86 (d, J=2.1 Hz, 1H), 7.67 (dd, J=8.5, 2.1 Hz, 1H), 6.92 (d, J=8.5 Hz, 1H), 6.45 (d, J=5.6 Hz, HRMS calculated for C$_{11}$H$_6$Cl$_3$INO [M+H]$^+$ 399.8560, found 399.8566.

Step 2: Preparation of t-butyl (1-(3-chloro-4-(2-chloro-4-iodophenoxy)pyridin-2-yl)piperidin-4-yl)carbamate

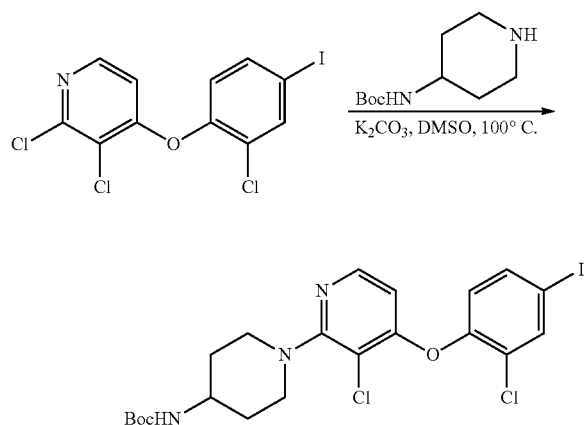

t-Butyl (1-(3-chloro-4-(2-chloro-4-iodophenoxy)pyridin-2-yl)piperidin-4-yl)carbamate was prepared from 2,3-dichloro-4-(2-chloro-4-iodophenoxy)pyridine (200 mg, 0.50 mmol) and t-butyl(piperidin-4-yl)carbamate as described in Example 2, Step 2 in 36% yield. $^1$H NMR (CDCl$_3$, 600 MHz) δ 7.97 (d, J=5.6 Hz, 1H), 7.81 (d, J=2.1 Hz, 1H), 7.59 (dd, J=8.5, 2.1 Hz, 1H), 6.82 (d, J=8.5 Hz, 1H), 6.17 (d, J=5.6 Hz, 1H), 4.54-4.53 (m, 1H), 3.81-3.77 (m, 2H), 3.68 (s, 1H), 2.97 (ddd, J=13.3, 11.4, 2.4 Hz, 2H), 2.08-2.05 (m, 2H), 1.59 (dtd, J=12.7, 11.1, 3.9 Hz, 2H). HRMS calculated for C$_{21}$H$_{25}$Cl$_2$F$_3$IN$_3$O$_3$ [M+H]$^+$ 564.0318, found 564.0322.

Step 3: Preparation of t-butyl (1-(3-chloro-4-(2-chloro-4-ethynylphenoxy)pyridin-2-yl)piperidin-4-yl)carbamate

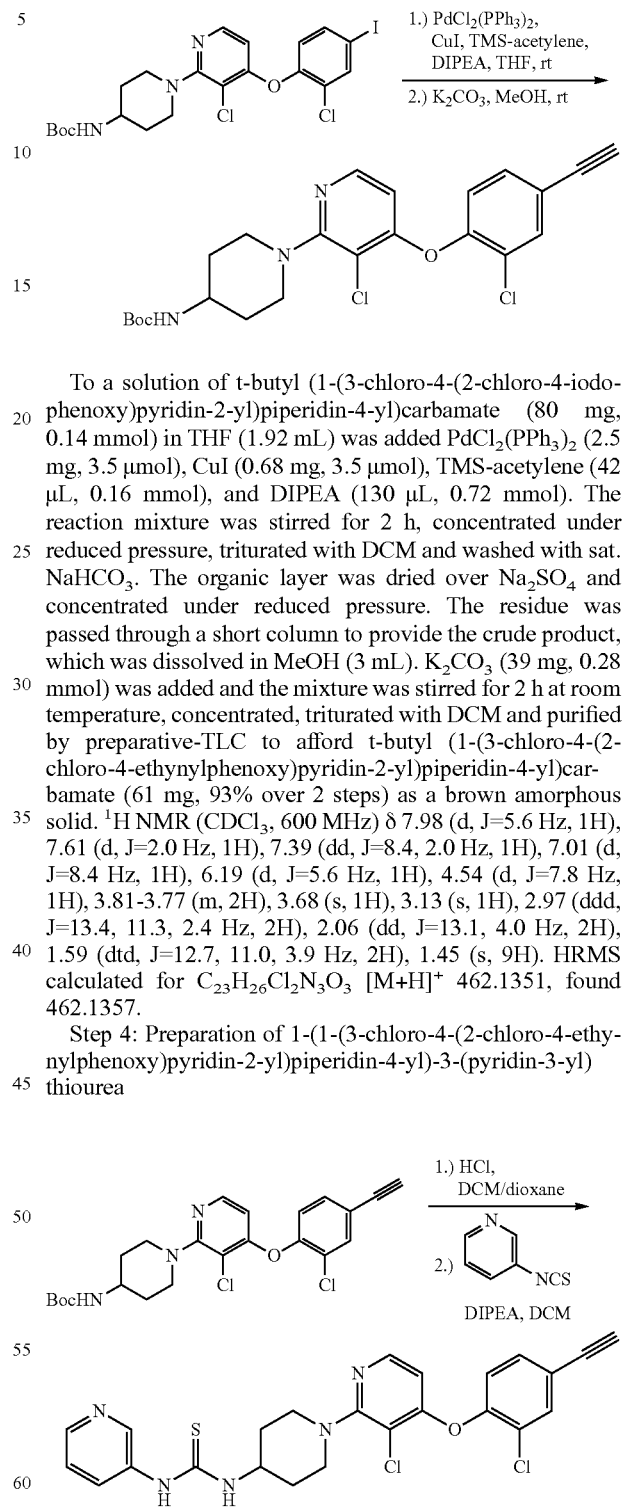

To a solution of t-butyl (1-(3-chloro-4-(2-chloro-4-iodophenoxy)pyridin-2-yl)piperidin-4-yl)carbamate (80 mg, 0.14 mmol) in THF (1.92 mL) was added PdCl$_2$(PPh$_3$)$_2$ (2.5 mg, 3.5 μmol), CuI (0.68 mg, 3.5 μmol), TMS-acetylene (42 μL, 0.16 mmol), and DIPEA (130 μL, 0.72 mmol). The reaction mixture was stirred for 2 h, concentrated under reduced pressure, triturated with DCM and washed with sat. NaHCO$_3$. The organic layer was dried over Na$_2$SO$_4$ and concentrated under reduced pressure. The residue was passed through a short column to provide the crude product, which was dissolved in MeOH (3 mL). K$_2$CO$_3$ (39 mg, 0.28 mmol) was added and the mixture was stirred for 2 h at room temperature, concentrated, triturated with DCM and purified by preparative-TLC to afford t-butyl (1-(3-chloro-4-(2-chloro-4-ethynylphenoxy)pyridin-2-yl)piperidin-4-yl)carbamate (61 mg, 93% over 2 steps) as a brown amorphous solid. $^1$H NMR (CDCl$_3$, 600 MHz) δ 7.98 (d, J=5.6 Hz, 1H), 7.61 (d, J=2.0 Hz, 1H), 7.39 (dd, J=8.4, 2.0 Hz, 1H), 7.01 (d, J=8.4 Hz, 1H), 6.19 (d, J=5.6 Hz, 1H), 4.54 (d, J=7.8 Hz, 1H), 3.81-3.77 (m, 2H), 3.68 (s, 1H), 3.13 (s, 1H), 2.97 (ddd, J=13.4, 11.3, 2.4 Hz, 2H), 2.06 (dd, J=13.1, 4.0 Hz, 2H), 1.59 (dtd, J=12.7, 11.0, 3.9 Hz, 2H), 1.45 (s, 9H). HRMS calculated for C$_{23}$H$_{26}$Cl$_2$N$_3$O$_3$ [M+H]$^+$ 462.1351, found 462.1357.

Step 4: Preparation of 1-(1-(3-chloro-4-(2-chloro-4-ethynylphenoxy)pyridin-2-yl)piperidin-4-yl)-3-(pyridin-3-yl)thiourea 1-(1-(3-Chloro-4-(2-chloro-4-ethynylphenoxy)pyridin-2-yl)piperidin-4-yl)-3-(pyridin-3-yl)thiourea was prepared from t-butyl (1-(3-chloro-4-(2-chloro-4-ethynylphenoxy)pyridin-2-yl)piperidin-4-yl) and 3-pyridineisothiocyanate as described in Example 1, Step 2 in 88% yield. $^1$H NMR (CDCl₃, 600 MHz) δ 8.65 (s, 1H), 8.50 (d, J=2.6 Hz, 1H), 8.46 (dd, J=4.8, 1.5 Hz, 1H), 7.95 (d, J=5.5 Hz, 1H), 7.74 (dt, J=8.4, 2.0 Hz, 1H), 7.59 (d, J=1.9 Hz, 1H), 7.38 (dd, J=8.3, 2.0 Hz, 1H), 7.34 (dd, J=8.2, 4.8 Hz, 1H), 7.00 (d, J=8.4 Hz, 1H), 6.22 (s, 1H), 6.17 (d, J=5.6 Hz, 1H), 4.52 (s, 1H), 3.79 (dd, J=13.1, 4.4 Hz, 2H), 3.12 (s, 1H), 3.02 (ddd, J=13.5, 11.1, 2.4 Hz, 2H), 2.22-2.18 (m, 2H), 1.64 (tt, J=15.2, 7.7 Hz, 2H). HRMS calculated for $C_{24}H_{22}Cl_2N_5OS$ [M+H]⁺ 498.0922, found 498.0925.

Example 6: 1-(1-(3-Chloro-4-(2-chloro-4-(trifluoromethoxy)phenoxy)pyridin-2-yl)piperidin-4-yl)-3-(pyridin-3-yl)urea

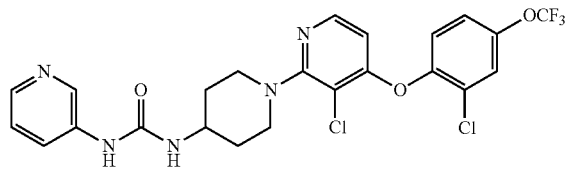

Preparation of 1-(1-(3-chloro-4-(2-chloro-4-(trifluoromethoxy)phenoxy)pyridin-2-yl)piperidin-4-yl)-3-(pyridin-3-yl)urea

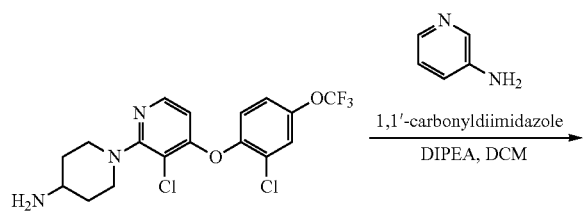

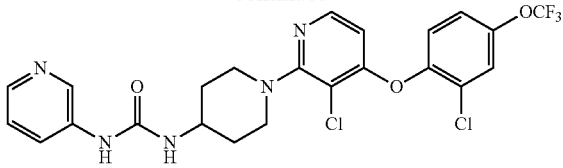 [SMILES: O=C(Nc1cccnc1)NC1CCN(c2nccc(Oc3ccc(OC(F)(F)F)cc3Cl)c2Cl)CC1]

To a solution of 3-aminopyridine (49 mg, 0.52 mmol) and DIPEA (90 µL, 0.52 mmol) in DCM (0.5 mL) was added 1,1-carbonyldiimidazole (100 mg, 0.62 mmol). The mixture was stirred for 3 h at room temperature prior to addition of 1-(3-chloro-4-(2-chloro-4-(trifluoromethoxy)phenoxy)pyridin-2-yl)piperidin-4-amine (109 mg, 0.26 mmol) (prepared according to Example 4, Steps 1-3a) and DIPEA (140 µL, 0.78 mmol). The mixture was stirred for 17 h at room temperature, diluted with DCM and washed with sat. NaHCO₃ and sat. NH₄Cl. The organic layer was dried over Na₂SO₄ and concentrated under reduced pressure. The residue was purified by preparative TLC to afford a crude mixture of 1-(1-(3-chloro-4-(2-chloro-4-ethynylphenoxy)pyridin-2-yl)piperidin-4-yl)-3-(pyridin-3-yl)thiourea, which was recrystallized to provide the product (31 mg, 22%) as a white solid. ¹H NMR (CDCl₃, 600 MHz) δ 8.34 (d, J=2.6 Hz, 1H), 8.23 (dd, J=4.8, 1.5 Hz, 1H), 8.05 (ddd, J=8.4, 2.7, 1.5 Hz, 1H), 7.98 (d, J=5.6 Hz, 1H), 7.73 (s, 1H), 7.39 (d, J=2.5 Hz, 1H), 7.24 (dd, J=8.4, 4.7 Hz, 1H), 7.17 (ddd, J=8.9, 2.7, 1.0 Hz, 1H), 7.12 (d, J=8.9 Hz, 1H), 6.17 (d, J=5.6 Hz, 1H), 5.42 (d, J=7.8 Hz, 1H), 3.97-3.90 (m, 1H), 3.79 (d, J=12.7 Hz, 2H), 3.02 (ddd, J=13.3, 11.1, 2.5 Hz, 2H), 2.13-2.07 (m, 2H), 1.66-1.59 (m, 2H). HRMS calculated for $C_{23}H_{20}Cl_2F_3N_5O_3$ [M+H]⁺ 542.0974, found 542.0984.

Example 7: (S)-1,3-Dioxo-7-(4-phenoxybenzoyl)hexahydroimidazo[1,5-a]pyrazin-2(3H)-yl 4-(4-(prop-2-yn-1-yloxy)phenyl)piperazine-1-carboxylate

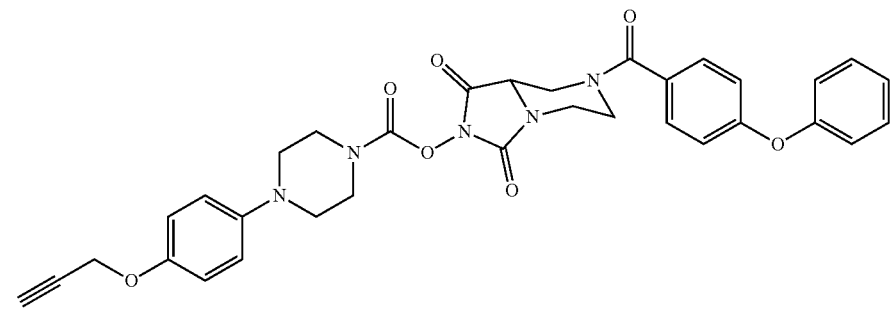 [SMILES: C#CCOc1ccc(N2CCN(C(=O)ON3C(=O)C4CN(C(=O)c5ccc(Oc6ccccc6)cc5)CCN4C3=O)CC2)cc1]

Preparation of (S)-1,3-dioxo-7-(4-phenoxybenzoyl)hexahydroimidazo[1,5-a]pyrazin-2(3H)-yl 4-(4-(prop-2-yn-1-yloxy)phenyl)piperazine-1-carboxylate

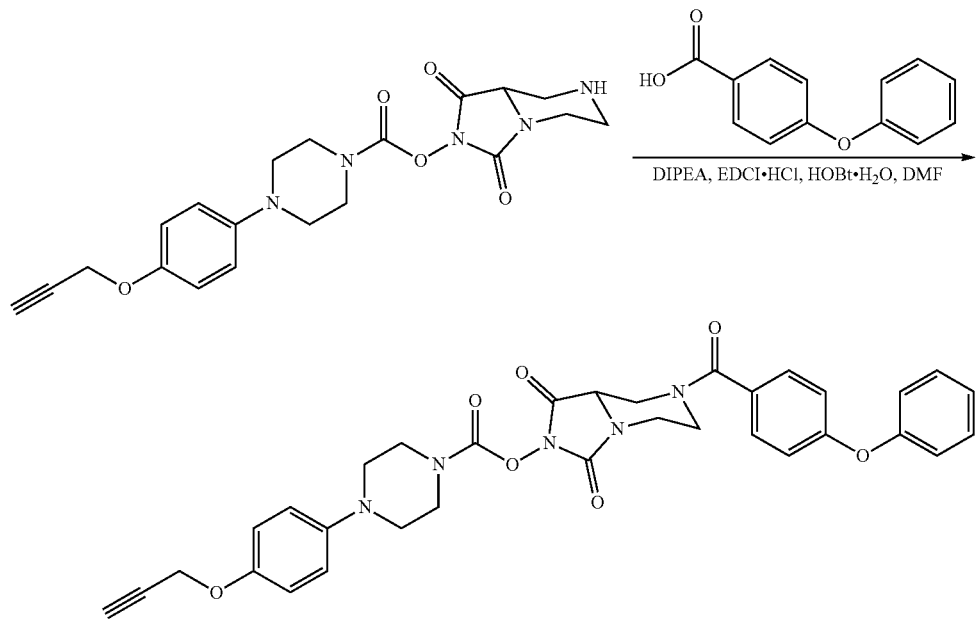

(S)-1,3-dioxohexahydroimidazo[1,5-a]pyrazin-2(3H)-yl 4-(4-(prop-2-yn-1-yloxy)phenyl)piperazine-1-carboxylate (prepared as reported by Cognetta, A. B. et al. Selective N-Hydroxyhydantoin Carbamate Inhibitors of Mammalian Serine Hydrolases. *Chemistry & Biology* 2015, 22, 928-937) (23 mg, 54 μmol, 1 eq) was dissolved in 200 μL DMF. 4-Phenoxy benzoic acid (12 mg, 54 μmol, 1 eq), 1-ethyl-3-(3-dimethylaminopropyl)carbodiimide hydrochloride (EDCI.HCl) (16 mg, 82 μmol, 1.5 eq), 1-hydroxybenzotriazole monohydrate (HOBt.H$_2$O) (13 mg, 82 μmol, 1.5 eq), and DIPEA (19 μL, 110 μmol, 2 eq) were added. The resulting mixture was stirred at room temperature overnight and poured into saturated aqueous NaHCO$_3$ solution. The mixture was extracted twice with EtOAc. The combined organic layers were washed with H$_2$O and brine, dried over Na$_2$SO$_4$, and concentrated under reduced pressure. The residue was purified by prep-TLC to afford (S)-1,3-dioxo-7-(4-phenoxybenzoyl)hexahydroimidazo[1,5-a]pyrazin-2(3H)-yl 4-(4-(prop-2-yn-1-yloxy)phenyl)piperazine-1-carboxylate (28 mg, 86%) as a white solid. $^1$H NMR (CDCl$_3$, 600 MHz) δ 7.43-7.37 (m, 4H), 7.19 (tt, J=7.4, 1.1 Hz, 1H), 7.09-7.06 (m, 2H), 7.03-7.01 (m, 2H), 6.94-6.88 (m, 4H), 4.64 (d, J=2.5 Hz, 3H), 4.14 (brs, 1H), 4.12 (brs, 1H), 3.77 (s, 2H), 3.64 (s, 2H), 3.22-2.91 (m, 8H), 2.51 (t, J=2.4 Hz, 1H). HRMS calculated for C$_{33}$H$_{31}$N$_5$O$_7$ [M+H]$^+$ 610.2296, found 610.2298.

Examples 8-85: Examples 8-85 were Prepared in a Similar Manner to Examples 1-7.

| Ex | Name | Structure | $^1$H NMR (CDCl$_3$, 600 MHz) | HRMS [M + H]$^+$ |
|---|---|---|---|---|
| 8 | 1-(1-(3-Chloro-5-methylpyridin-2-yl)piperidin-4-yl)-3-(pyridin-3-yl)thiourea | 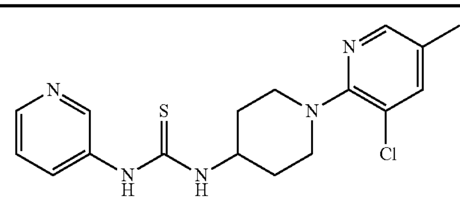 | δ 8.56-8.47 (m, 2H), 7.95 (s, 1H), 7.81 (s, 1H), 7.63 (d, J = 7.5 Hz, 1H), 7.42-7.38 (m, 1H), 7.36 (d, 1H), 5.87 (s, 1H), 4.48 (s, 1H), 3.63 (d, 2H), 2.95 (t, 2H), 2.21 (s, 3H), 2.20-2.15 (m, 2H), 1.64-1.55 (m, 2H). | 362.1205 |
| 9 | 1-(1-(3-Chloro-5-(trifluoromethyl)pyridin-2-yl)piperidin-4-yl)-3-phenylthiourea | 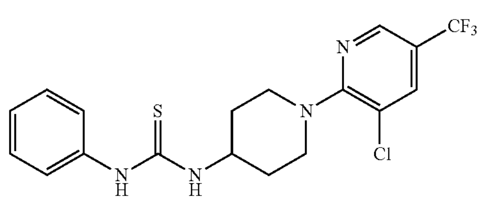 [SMILES: FC(F)(F)c1cnc(N2CCC(NC(=S)Nc3ccccc3)CC2)c(Cl)c1] | δ 8.35 (d, 1H), 7.82 (s, 1H), 7.72 (d, 1H), 7.49-7.41 (m, 2H), 7.33-7.30 (m, 1H), 7.24-7.17 (m, 2H), 5.89 (d, 1H), 4.61-4.55 (m, 1H), 4.04-3.89 (m, 2H), 3.10-3.05 (m, 2H), 2.23-2.19 (m, 2H), 1.58-1.47 (m, 2H) | 415.0970 |

| Ex | Name | Structure | ¹H NMR (CDCl₃, 600 MHz) | HRMS [M + H]⁺ |
|---|---|---|---|---|
| 10 | 1-(1-(5-Ethynylpyridin-2-yl)piperidin-4-yl)-3-(pyridin-3-yl)thiourea | 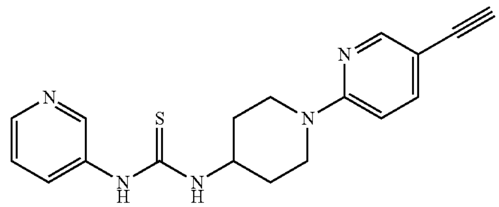 [SMILES: C#Cc1ccc(N2CCC(NC(=S)Nc3cccnc3)CC2)nc1] | δ 8.52-8.48 (m, 2H), 8.27 (d, 1H), 7.91 (s, 1H), 7.65-7.61 (m, 1H), 7.51 (d, 1H), 7.36 (d, 1H), 6.56 (d, 1H), 5.85 (d, 1H), 4.63-4.53 (m, 1H), 4.32-4.23 (m, 2H), 3.10-3.01 (m, 3H), 2.23-2.14 (m, 2H), 1.45-1.33 (m, 2H) | 338.1 (LRMS) |
| 11 | 1-(1-(5-Chloropyridin-2-yl)piperidin-4-yl)-3-(pyridin-3-yl)thiourea | 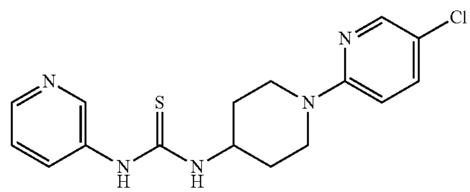 [SMILES: S=C(Nc1cccnc1)NC1CCN(c2ccc(Cl)cn2)CC1] | δ 8.52-8.41 (m, 3H), 8.05 (d, 1H), 7.71 (d, 1H), 7.38 (d, 1H), 7.32 (d, 1H), 6.57 (d, 1H), 6.15 (d, 1H), 4.53 (s, 1H), 4.18-4.13 (m, 2H), 3.04-2.96 (m, 2H), 2.18-2.12 (m, 2H), 1.46-1.36 (m, 2H) | 348.1044 |
| 12 | 1-(1-(5-Fluoropyridin-2-yl)piperidin-4-yl)-3-(pyridin-3-yl)thiourea | 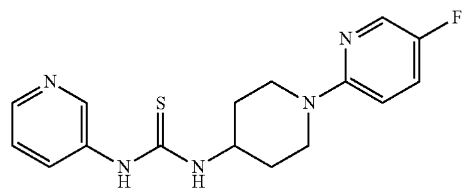 [SMILES: Fc1ccc(N2CCC(NC(=S)Nc3cccnc3)CC2)nc1] | δ 8.50-8.47 (m, 2H), 8.11 (s, 1H), 8.01 (d, 1H), 7.70-7.67 (m, 1H), 7.35 (d, 1H), 7.23 (d, 1H), 6.61 (d, 1H), 6.00 (d, 1H), 4.53 (s, 1H), 4.13-4.07 (m, 2H), 3.03-2.96 (m, 2H), 2.19-2.13 (m, 2H), 1.49-1.39 (m, 2H) | 332.1344 |
| 13 | 1-(Pyridin-3-yl)-3-(1-(5-(trifluoromethoxy)pyridin-2-yl)piperidin-4-yl)thiourea | 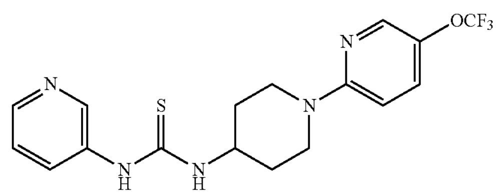 [SMILES: FC(F)(F)Oc1ccc(N2CCC(NC(=S)Nc3cccnc3)CC2)nc1] | δ 8.54-8.51 (m, 2H), 8.07-8.06 (m, 1H), 7.80 (s, 1H), 7.63-7.59 (m, 1H), 7.37 (d, 1H), 7.33 (d, 1H), 6.62 (d, 1H), 5.79 (d, 1H), 4.61-4.53 (m, 1H), 4.25-4.19 (m, 2H), 3.08-3.02 (m, 2H), 2.22-2.17 (m, 2H), 1.45-1.37 (m, 2H) | 398.1267 |
| 14 | 1-(Pyridin-3-yl)-3-(1-(5-(trifluoromethyl)pyridin-2-yl)piperidin-4-yl)thiourea | 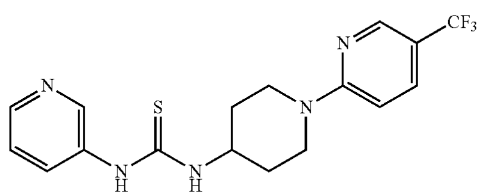 [SMILES: FC(F)(F)c1ccc(N2CCC(NC(=S)Nc3cccnc3)CC2)nc1] | δ 8.52-8.46 (m, 2H), 8.35 (s, 1H), 8.21-8.08 (m, 1H), 7.67 (d, 1H), 7.59 (d, 1H), 7.37-7.33 (m, 1H), 6.64 (d, 1H), 5.96 (s, 1H), 4.60 (s, 1H), 4.35 (d, 2H), 3.12-3.03 (m, 2H), 2.22-2.15 (m, 2H), 1.44-1.33 (m, 2H) | 382.1315 |
| 15 | 1-(Pyridin-3-yl)-3-(1-(4-(trifluoromethyl)pyridin-2-yl)piperidin-4-yl)thiourea | 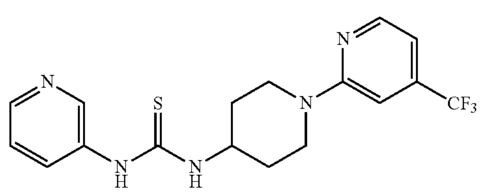 [SMILES: FC(F)(F)c1ccnc(N2CCC(NC(=S)Nc3cccnc3)CC2)c1] | δ 8.60 (d, 1H), 8.31-8.26 (m, 2H), 8.05 (d, 1H), 7.40 (d, 1H), 7.03 (d, 1H), 6.81 (d, 1H), 4.40-4.34 (m, 2H), 3.16-3.09 (m, 2H), 2.18-2.12 (m, 2H), 1.61-1.52 (m, 2H) | 382.1322 |
| 16 | 1-(Pyridin-3-yl)-3-(1-(3-(trifluoromethyl)pyridin-2-yl)piperidin-4-yl)thiourea | 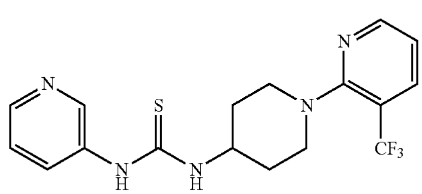 [SMILES: FC(F)(F)c1cccnc1N1CCC(NC(=S)Nc2cccnc2)CC1] | δ 8.51 (d, 1H), 8.48 (d, 1H), 8.42 (s, 1H), 8.40 (s, 1H), 7.83 (d, 1H), 7.73 (d, 1H), 7.36 (d, 1H), 6.99-6.96 (m, 1H), 6.12 (d, 1H), 4.49 (s, 1H), 3.52 (d, 2H), 3.04 (d, 2H), 2.21-2.14 (d, 2H), 1.63-1.54 (m, 2H) | 382.1313 |
| 17 | 1-(1-(3-Chloropyridin-2-yl)piperidin-4-yl)-3-(pyridin-3-yl)thiourea | 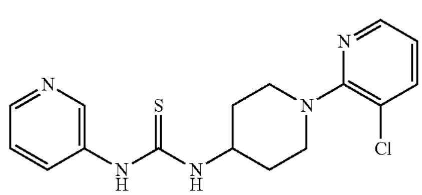 | δ 8.55-8.47 (m, 2H), 8.21-8.10 (m, 2H), 7.79-7.72 (m, 1H), 7.56 (d, 1H), 7.41-7.33 (m, 1H), 6.82 (t, 1H), 6.15 (s, 1H), 4.52 (s, 1H), 3.75 (d, 2H), 3.00 (t, 2H), 2.24-2.15 (m, 2H), 1.66-1.55 (d, 2H) | 348.1055 |

| Ex | Name | Structure | ¹H NMR (CDCl₃, 600 MHz) | HRMS [M + H]⁺ |
|---|---|---|---|---|
| 18 | 1-(1-(5-Chloro-3-(trifluoromethyl)pyridin-2-yl)piperidin-4-yl)-3-(pyridin-3-yl)thiourea | 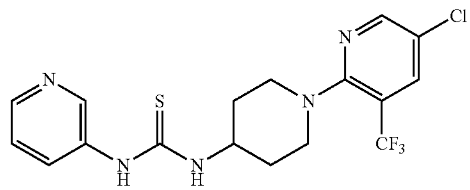 [SMILES: FC(F)(F)c1cc(Cl)cnc1N1CCC(NC(=S)Nc2cccnc2)CC1] | δ 8.50 (d, 1H), 8.48 (d, 1H), 8.44 (s, 1H), 8.32 (d, 1H), 7.79 (d, 1H), 7.71 (d, 1H), 7.36 (d, 1H), 6.09 (d, 1H), 4.49 (s, 1H), 3.56-3.48 (m, 2H), 3.06-3.00 (m, 2H), 2.20-2.45 (m, 2H), 1.60-1.52 (m, 2H) | 416.0922 |
| 19 | 1-(1-(6-Chloropyridin-3-yl)piperidin-4-yl)-3-(pyridin-3-yl)thiourea | 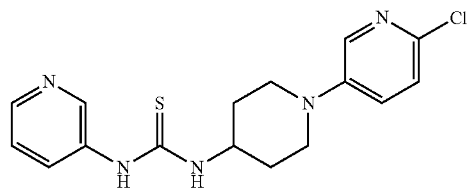 [SMILES: S=C(Nc1cccnc1)NC1CCN(c2ccc(Cl)nc2)CC1] | (MeOD) δ 9.45 (s, 1H), 8.51 (s, 1H), 8.24 (s, 1H), 8.05 (s, 1H), 8.01-7.87 (m, 2H), 7.40 (d, 1H), 7.30 (d, 1H), 7.24 (d, 1H), 4.28 (s, 1H), 3.68 (d, 2H), 2.92-2.80 (m, 2H), 2.00-1.90 (m, 2H), 1.60-1.46 (m, 2H) | 348.1049 |
| 20 | 1-(1-(3-Chloro-5-ethynylpyridin-2-yl)piperidin-4-yl)-3-(pyridin-3-yl)thiourea | 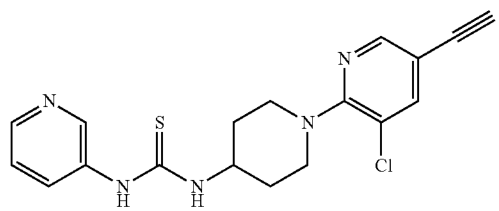 [SMILES: C#Cc1cnc(N2CCC(NC(=S)Nc3cccnc3)CC2)c(Cl)c1] | δ 8.53-8.51 (m, 2H), 8.23 (d, 1H), 8.06 (s, 1H), 7.69-7.65 (m, 1H), 7.63 (d, 1H), 7.37 (d, 1H), 5.95 (d, 1H), 4.53 (s, 1H), 3.90-3.82 (m, 2H), 3.13 (s, 1H), 3.05-2.98 (m, 2H), 2.23-2.17 (m, 2H), 1.62-1.54 (m, 2H) | 372.1050 |
| 21 | 1-(1-(3-Fluoro-5-(trifluoromethyl)pyridin-2-yl)piperidin-4-yl)-3-(pyridin-3-yl)thiourea | 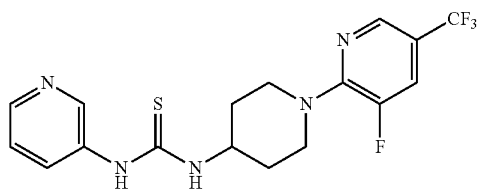 [SMILES: Fc1cc(C(F)(F)F)cnc1N1CCC(NC(=S)Nc2cccnc2)CC1] | δ 8.52-8.44 (m, 3H), 8.20-8.17 (m, 1H), 7.72-7.69 (m, 1H), 7.37-7.32 (m, 2H), 6.08 (d, 1H), 4.62-4.53 (m, 1H), 4.28-4.22 (m, 2H), 3.14-3.07 (m, 2H), 2.22-2.16 (m, 2H), 1.48 (q, 2H) | 400.1224 |
| 22 | 1-(Pyridin-3-yl)-3-(1-(4-(4-(trifluoromethoxy)phenyl)pyridin-2-yl)piperidin-4-yl)thiourea | 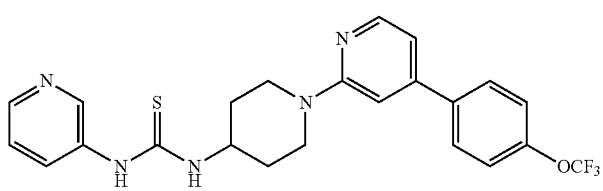 [SMILES: FC(F)(F)Oc1ccc(-c2ccnc(N3CCC(NC(=S)Nc4cccnc4)CC3)c2)cc1] | δ 8.52-8.49 (m, 2H), 8.33 (d, 1H), 7.91-7.88 (m, 2H), 7.84 (s, 1H), 7.68-7.64 (m, 1H), 7.36 (d, 1H), 7.29-7.25 (m, 2H), 7.00 (d, 1H), 6.65-6.62 (m, 1H), 5.94 (d, 1H), 4.68-4.58 (m, 1H), 3.92 (d, 2H), 3.15-3.04 (m, 2H), 2.25-2.17 (m, 2H), 1.50-1.38 (m, 2H) | 474.1584 |
| 23 | 1-(Pyridin-3-yl)-3-(1-(4-(3-(trifluoromethoxy)phenyl)pyridin-2-yl)piperidin-4-yl)thiourea | 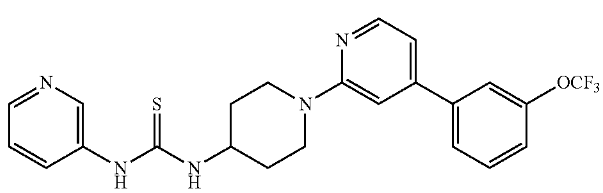 [SMILES: FC(F)(F)Oc1cccc(-c2ccnc(N3CCC(NC(=S)Nc4cccnc4)CC3)c2)c1] | δ 8.50-8.39 (m, 3H), 8.30 (d, 1H), 7.79-7.75 (m, 2H), 7.71 (s, 1H), 7.44 (t, 1H), 7.31 (d, 1H), 7.25-7.22 (m, 1H), 6.98 (d, 1H), 6.63 (d, 1H), 6.36 (d, 1H), 4.65-4.56 (m, 1H), 3.90-3.83 (m, 2H), 3.13-3.04 (m, 2H), 2.20-2.13 (m, 2H), 1.46-1.37 (m, 2H) | 474.1580 |
| 24 | 1-(pyridin-3-yl)-3-(1-(4-(2-(trifluoromethyl)phenyl)pyridin-2-yl)piperidin-4-yl)thiourea | 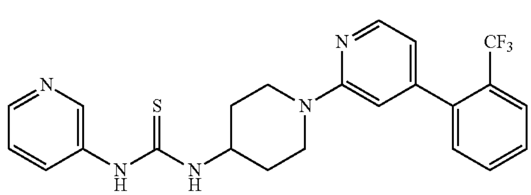 [SMILES: FC(F)(F)c1ccccc1-c1ccnc(N2CCC(NC(=S)Nc3cccnc3)CC2)c1] | δ 8.59 (s, 1H), 8.43-8.38 (m, 2H), 8.24 (d, 1H), 7.81 (d, 1H), 7.71 (d, 1H), 7.54-7.46 (m, 2H), 7.42 (d, 1H), 7.29 (d, 1H), 6.74 (d, 1H), 6.67 (d, 1H), 6.49 (d, 1H), 4.66-4.57 (m, 1H), 3.89-3.83 (m, 2H), 3.12-3.04 (m, 2H), 2.15-2.09 (m, 2H), 1.40-1.31 (m, 2H) | 458.1637 |

| Ex | Name | Structure | ¹H NMR (CDCl₃, 600 MHz) | HRMS [M + H]⁺ |
|---|---|---|---|---|
| 25 | 1-(1-(5-Chloro-4-(trifluoromethyl)pyridin-2-yl)piperidin-4-yl)-3-(pyridin-3-yl)thiourea | 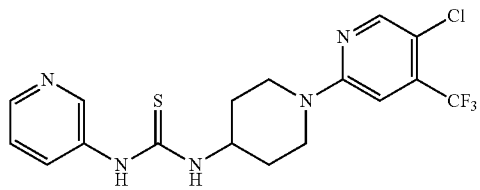 [SMILES: FC(F)(F)c1cc(N2CCC(NC(=S)Nc3cccnc3)CC2)ncc1Cl] | (DMSO-d₆) δ 9.50 (s, 1H), 8.56-8.54 (m, 1H), 8.33 (s, 1H), 8.28 (d, 1H), 7.98 7.90 (m, 2H), 7.33 (d, 1H), 7.20 (s, 1H), 4.42 (s, 1H), 4.30 (d, 2H), 3.10 (t, 2H), 2.03-1.97 (m, 2H), 1.52-1.44 (m, 2H) | 416.0919 |
| 26 | 1-(1-(3-Chloro-4-(trifluoromethyl)pyridin-2-yl)piperidin-4-yl)-3-(pyridin-3-yl)thiourea | 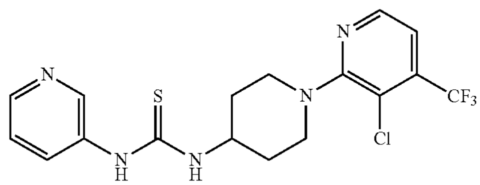 [SMILES: FC(F)(F)c1ccnc(N2CCC(NC(=S)Nc3cccnc3)CC2)c1Cl] | (MeOD) δ 8.60 (d, 1H), 8.35 (d, 1H), 8.28 (d, 1H), 8.07-8.04 (m, 1H), 7.39 (d, 1H), 7.27 (d, J = 5.0 Hz, 1H), 4.49 (s, 1H), 3.83-3.75 (m, 2H), 3.09-3.00 (m, 2H), 2.22-2.14 (m, 2H), 1.80-1.70 (m, 2H) | 416.0930 |
| 27 | 1-(1-(6-Chloro-4-(trifluoromethyl)pyridin-2-yl)piperidin-4-yl)-3-(pyridin-3-yl)thiourea | 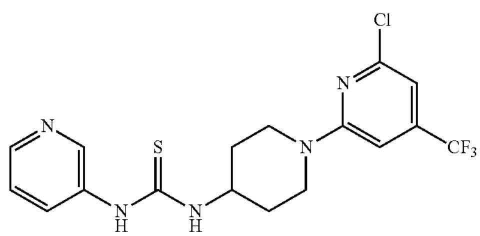 [SMILES: FC(F)(F)c1cc(Cl)nc(N2CCC(NC(=S)Nc3cccnc3)CC2)c1] | (DMSO-d₆) δ 9.51 (s, 1H), 8.55 (d, 1H), 8.28 (d, 1H), 8.00-7.90 (m, 2H), 7.33 (d, 1H), 7.12 (s, 1H), 6.90 (s, 1H), 4.43 (s, 1H), 4.34-4.22 (m, 2H), 3.17-3.04 (m, 2H), 2.05-1.98 (m, 2H), 1.52-1.43 (m, 2H) | 416.0919 |
| 28 | 1-(1-(4-Chloropyridin-2-yl)piperidin-4-yl)-3-(pyridin-3-yl)thiourea | 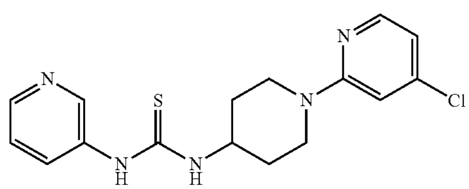 [SMILES: S=C(Nc1cccnc1)NC1CCN(c2cc(Cl)ccn2)CC1] | δ 8.49-8.44 (m, 2H), 8.36 (s, 1H), 8.01 (d, 1H), 7.72-7.67 (m, 1H), 7.33 (d, 1H), 6.62-6.56 (m, 2H), 6.07 (d, 1H), 4.59-4.53 (m, 1H), 4.23-4.15 (m, 2H), 3.06-2.98 (m, 2H), 2.20-2.12 (m, 2H), 1.45-1.35 (m, 2H) | 348.1057 |
| 29 | 1-(Pyridin-3-yl)-3-(1-(6-(trifluoromethyl)pyridin-2-yl)piperidin-4-yl)thiourea | 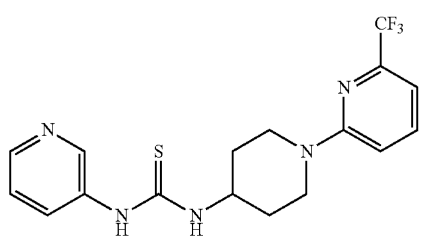 [SMILES: FC(F)(F)c1cccc(N2CCC(NC(=S)Nc3cccnc3)CC2)n1] | δ 8.49-8.40 (m, 3H), 7.73-7.68 (m, 1H), 7.54 (t, 1H), 7.33 (d, 1H), 6.90 (d, 1H), 6.76 (d, 1H), 6.12 (d, 1H), 4.55 (s, 1H), 4.32-4.24 (m, 2H), 3.08-2.99 (m, 2H), 2.20-2.11 (m, 2H), 1.46-1.35 (m, 2H) | 382.1322 |
| 30 | 1-(1-(4-(Cyclohexyloxy)pyridin-2-yl)piperidin-4-yl)-3-(pyridin-3-yl)thiourea | 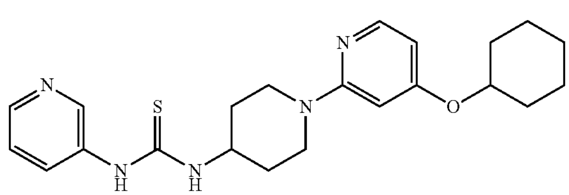 [SMILES: S=C(Nc1cccnc1)NC1CCN(c2cc(OC3CCCCC3)ccn2)CC1] | δ 8.50-8.41 (m, 2H), 8.31 (s, 1H), 7.96 (d, 1H), 7.77 (d, 1H), 7.32 (d, 1H), 6.27-6.21 (m, 2H), 6.10 (d, 1H), 4.52 (s, 1H), 4.31-4.25 (m, 1H), 4.15-4.08 (m, 2H), 3.02-2.95 (m, 2H), 2.16-2.10 (m, 2H), 1.97-1.90 (m, 2H), 1.82-1.74 (m, 2H), 1.60-1.27 (m, 8H) | 412.2173 |
| 31 | 1-(1-(4-(Cyclopropylmethoxy)pyridin-2-yl)piperidin-4-yl)-3-(pyridin-3-yl)thiourea | 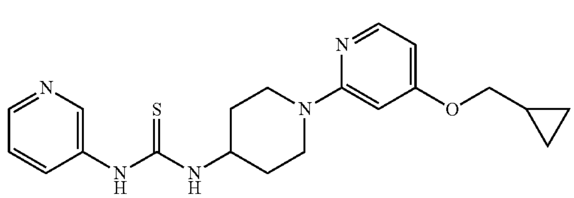 [SMILES: S=C(Nc1cccnc1)NC1CCN(c2cc(OCC3CC3)ccn2)CC1] | δ 8.49 (s, 3H), 7.96 (d, 1H), 7.77 (s, 1H), 7.35 (s, 1H), 6.40-6.19 (m, 2H), 6.10 (s, 1H), 4.52 (s, 1H), 4.12 (d, 2H), 3.79 (d, 2H), 2.98 (t, 2H), 2.19-2.06 (m, 2H), 1.40 (s, 2H), 1.27-1.19 (m, 1H), 0.67-0.61 (m, 2H), 0.36-0.30 (m, 2H) | 384.1861 |

-continued

| Ex | Name | Structure | ¹H NMR (CDCl₃, 600 MHz) | HRMS [M + H]⁺ |
|---|---|---|---|---|
| 32 | 1-(1-(4-(2,2-Difluoroethoxy)pyridin-2-yl)piperidin-4-yl)-3-(pyridin-3-yl)thiourea | 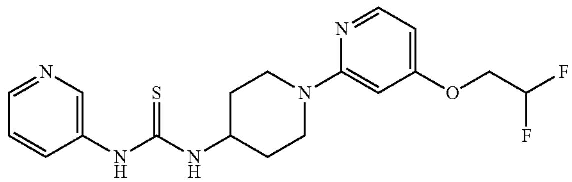 [SMILES: FC(F)COc1ccnc(N2CCC(NC(=S)Nc3cccnc3)CC2)c1] | δ 8.54-8.34 (m, 3H), 8.02 (d, 1H), 7.74 (d, 1H), 7.32 (d, 1H), 6.32-5.93 (m, 4H), 4.54 (s, 1H), 4.24-4.08 (m, 4H), 3.00 (t, 2H), 2.21-2.04 (m, 2H), 1.40-1.33 (m, 2H) | 394.1518 |
| 33 | 1-(1-(4-(2-Cyclopropylethoxy)pyridin-2-yl)piperidin-4-yl)-3-(pyridin-3-yl)thiourea | 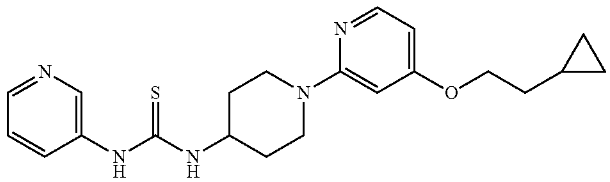 [SMILES: S=C(Nc1cccnc1)NC1CCN(c2cc(OCCC3CC3)ccn2)CC1] | δ 8.63 (s, 1H), 8.44 (d, 1H), 8.39 (d, 1H), 7.96 (d, 1H), 7.83-7.78 (m, 1H), 7.29 (d, 1H), 6.44 (d, 1H), 6.24 (d, 1H), 6.10 (d, 1H), 4.52 (s, 1H), 4.16-4.08 (m, 2H), 4.02 (t, 2H), 3.02-2.94 (m, 2H), 2.15-2.09 (m, 2H), 1.65 (q, 2H), 1.46-1.36 (m, 2H), 0.85-0.77 (m, 1H), 0.50-0.45 (m, 2H), 0.12-0.07 (m, 2H) | 398.2019 |
| 34 | 1-(Pyridin-3-yl)-3-(1-(4-(4,4,4-trifluorobutoxy)pyridin-2-yl)piperidin-4-yl)thiourea | 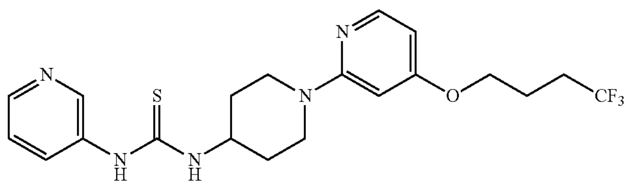 [SMILES: FC(F)(F)CCCOc1ccnc(N2CCC(NC(=S)Nc3cccnc3)CC2)c1] | δ 8.52-8.41 (m, 2H), 8.30 (s, 1H), 7.99 (d, 1H), 7.76 (d, 1H), 7.33 (d, 1H), 6.20 (d, 2H), 6.09 (d, 1H), 4.54 (s, 1H), 4.20-4.14 (m, 2H), 4.02 (t, 2H), 3.04-2.97 (m, 2H), 2.34-2.24 (m, 2H), 2.18-2.11 (m, 2H), 2.06-2.00 (m, 2H), 1.45-1.35 (m, 2H) | 440.1731 |
| 35 | 1-(1-(4-((4,4-Difluorocyclohexyl)oxy)pyridin-2-yl)piperidin-4-yl)-3-(pyridin-3-yl)thiourea | 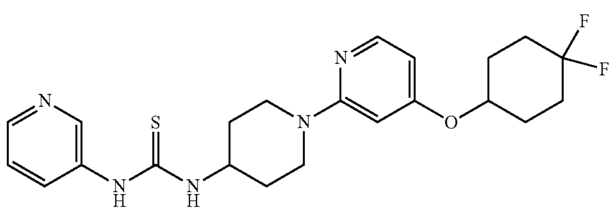 [SMILES: FC1(F)CCC(Oc2ccnc(N3CCC(NC(=S)Nc4cccnc4)CC3)c2)CC1] | δ 8.48 (s, 2H), 8.18 (s, 1H), 8.00 (d, 1H), 7.75 (s, 1H), 7.35 (s, 1H), 6.24-6.10 (m, 1H), 6.18-6.10 (m, 2H), 4.59-4.50 (m, 2H), 4.16 (d, 2H), 3.01 (t, 2H), 2.21-1.84 (m, 10H), 1.48-1.37 (m, 2H) | 448.1983 |
| 36 | Isopropyl 4-((2-(4-(3-(pyridin-3-yl)thioureido)piperidin-1-yl)pyridin-4-yl)oxy)piperidine-1-carboxylate | 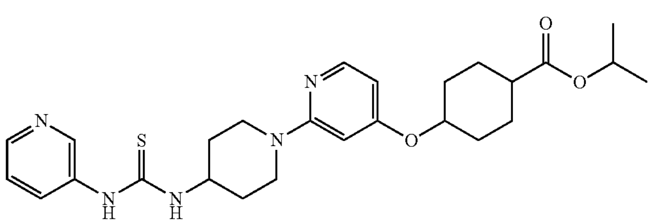 [SMILES: CC(C)OC(=O)C1CCC(Oc2ccnc(N3CCC(NC(=S)Nc4cccnc4)CC3)c2)CC1] | δ 8.50-8.44 (m, 2H), 8.10 (s, 1H), 8.00 (d, 1H), 7.74 (d, 1H), 7.34 (d, 1H), 6.21 (d, 1H), 6.14-6.06 (m, 2H), 4.95-4.89 (m, 1H), 4.59-4.48 (m, 2H), 4.16 (d, 2H), 3.71-3.62 (m, 2H), 3.46-3.37 (m, 2H), 3.05-2.96 (m, 2H), 2.19-2.11 (m, 3H), 1.94-1.83 (m, 2H), 1.78-1.68 (m, 2H), 1.46-1.35 (m, 2H), 1.24 (d, 6H) | 499.2493 |
| 37 | 1-(1-(4-(Benzyloxy)pyridin-2-yl)piperidin-4-yl)-3-(pyridin-3-yl)thiourea | 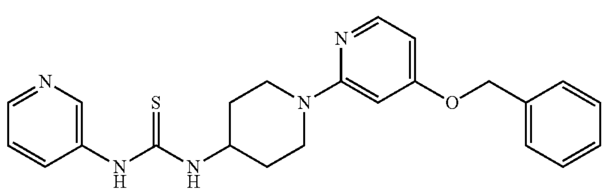 [SMILES: S=C(Nc1cccnc1)NC1CCN(c2cc(OCc3ccccc3)ccn2)CC1] | δ 8.51 (s, 1H), 8.45 (s, 1H), 8.43-8.39 (m, 1H), 7.99 (d, 1H), 7.80-7.76 (m, 1H), 7.41-7.35 (m, 4H), 7.35-7.28 (m, 2H), 6.35-6.28 (m, 2H), 6.18 (d, 1H), 5.05 (s, 2H), 4.52 (s, 1H), 4.15-4.08 (m, 2H), 3.03-2.93 (m, 2H), 2.15-2.08 (m, 2H), 1.44-1.35 (m, 2H) | 420.1859 |

| Ex | Name | Structure | ¹H NMR (CDCl₃, 600 MHz) | HRMS [M + H]⁺ |
|---|---|---|---|---|
| 38 | 1-(1-(4-((4-Fluorobenzyl)oxy)pyridin-2-yl)piperidin-4-yl)-3-(pyridin-3-yl)thiourea | 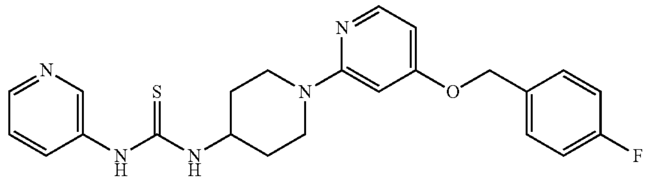 [SMILES: Fc1ccc(COc2ccnc(N3CCC(NC(=S)Nc4cccnc4)CC3)c2)cc1] | δ 8.52-8.41 (m, 2H), 8.36 (s, 1H), 8.00 (d, 1H), 7.77-7.71 (m, 1H), 7.40-7.29 (m, 3H), 7.09-7.04 (m, 2H), 6.28 (d, 1H), 6.21-6.15 (m, 2H), 5.01 (s, 2H), 4.53 (s, 1H), 4.18-4.09 (m, 2H), 3.03-2.94 (m, 2H), 2.17-2.10 (m, 2H), 1.44-1.36 (m, 2H) | 438.1766 |
| 39 | 1-(Pyridin-3-yl)-3-(1-(4-((4-(trifluoromethoxy)benzyl)oxy)pyridin-2-yl)piperidin-4-yl)thiourea | 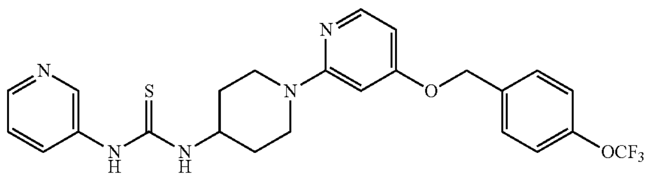 [SMILES: FC(F)(F)Oc1ccc(COc2ccnc(N3CCC(NC(=S)Nc4cccnc4)CC3)c2)cc1] | δ 8.47 (s, 2H), 8.19 (s, 1H), 8.01 (d, 1H), 7.72 (s, 1H), 7.45-7.41 (m, 2H), 7.35 (s, 1H), 7.23 (d, 2H), 6.28 (d, 1H), 6.19-6.15 (m, 1H), 6.10 (s, 1H), 5.05 (s, 2H), 4.54 (s, 1H), 4.19-4.11 (m, 2H), 3.04-2.95 (m, 2H), 2.19-2.09 (m, 2H), 1.47-1.35 (m, 2H) | 456.1669 |
| 40 | 1-(1-(4-Phenoxypyridin-2-yl)piperidin-4-yl)-3-(pyridin-3-yl)thiourea | 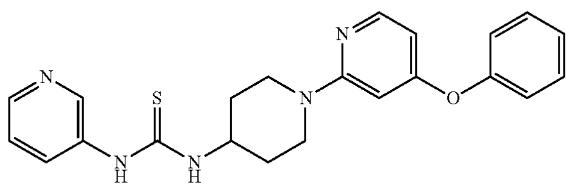 [SMILES: S=C(Nc1cccnc1)NC1CCN(c2cc(Oc3ccccc3)ccn2)CC1] | δ 8.49 (s, 1H), 8.47-8.44 (m, 1H), 8.42 (d, 1H), 7.99 (d, 1H), 7.78-7.73 (m, 1H), 7.40-7.35 (m, 2H), 7.31 (d, 1H), 7.21-7.18 (m, 1H), 7.07-7.04 (m, 2H), 6.25 (d, 1H), 6.19-6.16 (m, 2H), 4.52 (s, 1H), 4.15-4.06 (m, 2H), 3.01-2.93 (m, 2H), 2.16-2.09 (m, 2H), 1.44-1.35 (m, 2H) | 406.1711 |
| 41 | 1-(1-(4-(4-Fluorophenoxy)pyridin-2-yl)piperidin-4-yl)-3-(pyridin-3-yl)thiourea | 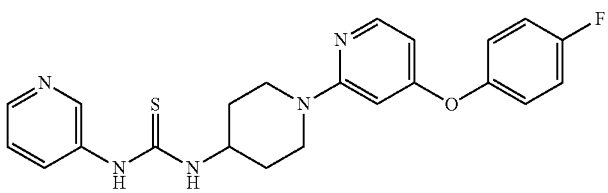 [SMILES: Fc1ccc(Oc2ccnc(N3CCC(NC(=S)Nc4cccnc4)CC3)c2)cc1] | δ 8.48 (s, 2H), 8.37 (s, 1H), 8.02 (d, 1H), 7.81-7.71 (m, 1H), 7.37 (s, 1H), 7.12-7.02 (m, 4H), 6.23-6.14 (m, 3H), 4.55 (s, 1H), 4.17-4.08 (m, 2H), 3.05-2.97 (m, 2H), 2.20-2.11 (m, 2H), 1.48-1.36 (m, 2H) | 424.1614 |
| 42 | 1-(1-(4-((3,4-Difluorobenzyl)oxy)pyridin-2-yl)piperidin-4-yl)-3-(pyridin-3-yl)thiourea | 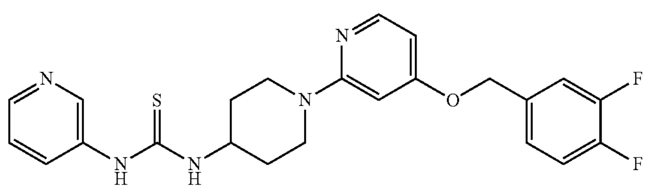 [SMILES: Fc1ccc(COc2ccnc(N3CCC(NC(=S)Nc4cccnc4)CC3)c2)cc1F] | δ 8.52-8.44 (m, 2H), 8.12 (s, 1H), 8.01 (d, 1H), 7.70 (d, 1H), 7.34 (d, 1H), 7.25-7.09 (m, 3H), 6.26 (d, 1H), 6.16 (d, 1H), 6.03 (d, 1H), 5.00 (s, 2H), 4.54 (s, 1H), 4.19-4.13 (m, 2H), 3.05-2.97 (m, 2H), 2.18-2.11 (m, 2H), 1.46-1.37 (m, 2H) | 456.1669 |
| 43 | 1-(1-(4-(4-Chloro-2-fluorophenoxy)pyridin-2-yl)piperidin-4-yl)-3-(pyridin-3-yl)thiourea | 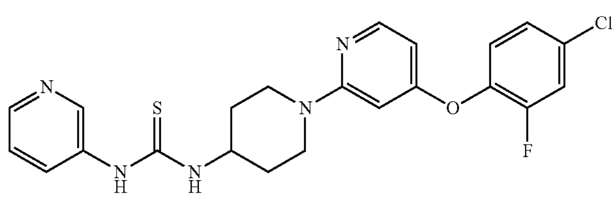 [SMILES: Fc1cc(Cl)ccc1Oc1ccnc(N2CCC(NC(=S)Nc3cccnc3)CC2)c1] | δ 8.52-8.43 (m, 2H), 8.14 (s, 1H), 8.00 (d, 1H), 7.71 (d, 1H), 7.35 (d, 1H), 7.22 (d, 1H), 7.12-7.07 (m, 1H), 7.04-6.99 (m, 1H), 6.14-6.12 (m, 1H), 6.07-6.02 (m, 2H), 4.54 (s, 1H), 4.19-4.08 (m, 2H), 3.05-2.94 (m, 2H), 2.19-2.10 (m, 2H), 1.46-1.35 (m, 2H) | 458.1221 |
| 44 | 1-(1-(4-Methoxypyridin-2-yl)piperidin-4-yl)-3-(pyridin-3-yl)thiourea | 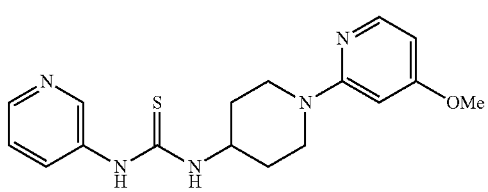 [SMILES: COc1ccnc(N2CCC(NC(=S)Nc3cccnc3)CC2)c1] | δ 8.62 (s, 1H), 8.44 (d, 1H), 8.39 (d, 1H), 7.97 (d, 1H), 7.82-7.78 (m, 1H), 7.29 (d, 1H), 6.41 (d, 1H), 6.23 (d, 1H), 6.09 (d, 1H), 4.52 (s, 1H), 4.15-4.08 (m, 2H), 3.78 (s, 3H), 3.01-2.95 (m, 2H), 2.15-2.10 (m, 2H), 1.40 (q, 2H) | 344.1545 |

-continued

| Ex | Name | Structure | ¹H NMR (CDCl₃, 600 MHz) | HRMS [M + H]⁺ |
|---|---|---|---|---|
| 45 | 1-(1-(4-Phenylpyridin-2-yl)piperidin-4-yl)-3-(pyridin-3-yl)thiourea | 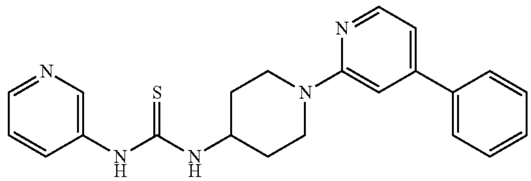 [SMILES: S=C(Nc1cccnc1)NC1CCN(c2cc(-c3ccccc3)ccn2)CC1] | (DMSO-d₆) δ 9.71 (s, 1H), 8.57 (d, 1H), 8.27 (d, 1H), 8.24 (d, 1H), 8.17 (d, 1H), 8.05-8.02 (m, 2H), 7.96 (d, 1H), 7.49-7.41 (m, 3H), 7.36-7.31 (m, 2H), 6.89 (d, 1H), 4.44 (s, 1H), 4.07 (d, 2H), 3.17-3.08 (m, 2H), 2.06-2.00 (m, 2H), 1.59-1.50 (m, 2H) | 390.1758 |
| 46 | 1-(1-(4-(4-Methoxyphenyl)pyridin-2-yl)piperidin-4-yl)-3-(pyridin-3-yl)thiourea | 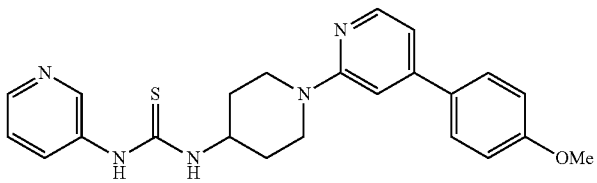 [SMILES: COc1ccc(-c2ccnc(N3CCC(NC(=S)Nc4cccnc4)CC3)c2)cc1] | δ 10.11 (s, 1H), 8.79 (s, 1H), 8.64 (s, 1H), 8.25-7.97 (m, 3H), 7.79 (d, 2H), 7.11 (d, 1H), 6.93 (d, 2H), 6.84 (s, 1H), 6.71-6.67 (m, 1H), 4.68-4.59 (m, 1H), 4.01-3.91 (m, 2H), 3.77 (s, 3H), 3.43-3.32 (m, 2H), 2.14-2.05 (m, 2H), 1.77-1.66 (m, 2H) | 420.1863 |
| 47 | 1-(1-(4-(4-Fluorophenyl)pyridin-2-yl)piperidin-4-yl)-3-(pyridin-3-yl)thiourea | 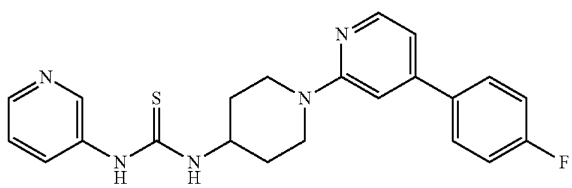 [SMILES: Fc1ccc(-c2ccnc(N3CCC(NC(=S)Nc4cccnc4)CC3)c2)cc1] | δ 9.66 (s, 1H), 8.58 (d, 1H), 8.23 (d, 1H), 8.19-8.16 (m, 2H), 7.99 (s, 1H), 7.84-7.79 (m, 2H), 7.19 (d, 1H), 7.13-7.08 (m, 2H), 6.93 (d, 1H), 6.62 (d, 1H), 4.65-4.56 (m, 1H), 3.90-3.84 (m, 2H), 3.23-3.15 (m, 2H), 2.19-2.11 (m, 2H), 1.63-1.55 (m, 2H) | 408.1663 |
| 48 | 1-(1-(4-(3,4-Difluorophenyl)pyridin-2-yl)piperidin-4-yl)-3-(pyridin-3-yl)thiourea | 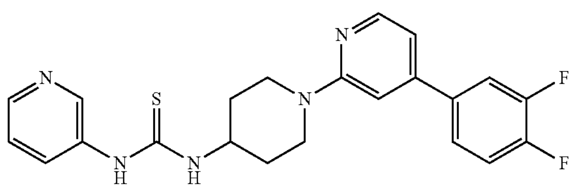 [SMILES: Fc1ccc(-c2ccnc(N3CCC(NC(=S)Nc4cccnc4)CC3)c2)cc1F] | δ 8.63-8.24 (m, 4H), 7.81 (s, 1H), 7.78-7.70 (m, 1H), 7.67-7.58 (m, 1H), 7.36 (s, 1H), 7.26-7.19 (m, 1H), 7.00-6.95 (m, 1H), 6.68 6.60 (m, 1H), 6.55-6.35 (m, 1H), 4.64 (s, 1H), 3.92 (d, 2H), 3.16-3.07 (m, 2H), 2.26-2.15 (m, 2H), 1.55-1.42 (m, 2H) | 426.1570 |
| 49 | 1-(Pyridin-3-yl)-3-(1-(4-(3-(trifluoromethoxy)phenoxy)pyridin-2-yl)piperidin-4-yl)thiourea | 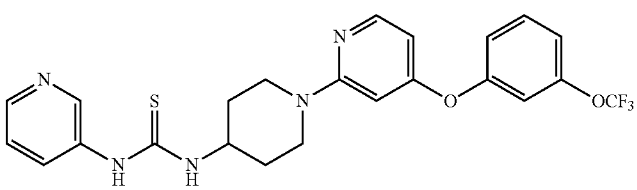 [SMILES: FC(F)(F)Oc1cccc(Oc2ccnc(N3CCC(NC(=S)Nc4cccnc4)CC3)c2)c1] | δ 8.47-8.46 (m, 1H), 8.44 (d, 1H), 8.41 (s, 1H), 8.04 (d, 1H), 7.73 (s, 1H), 7.38 (t, 1H), 7.33 (d, 1H), 7.05 (d, 1H), 6.99 (d, 1H), 6.94-6.92 (m, 1H), 6.21-6.18 (m, 2H), 6.15 (d, 1H), 4.54 (s, 1H), 4.17-4.09 (m, 2H), 3.04-2.95 (m, 2H), 2.19-2.10 (m, 2H), 1.45-1.36 (m, 2H) | 490.1527 |
| 50 | 1-(Pyridin-3-yl)-3-(1-(4-(2-(trifluoromethoxy)phenoxy)pyridin-2-yl)piperidin-4-yl)thiourea | 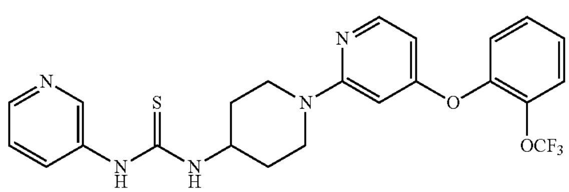 | δ 8.50-8.46 (m, 2H), 8.18 (s, 1H), 8.01 (d, 1H), 7.71-7.66 (m, 1H), 7.37-7.28 (m, 3H), 7.25-7.21 (m, 1H), 7.14 (d, 1H), 6.19 (d, 1H), 6.13 (d, 1H), 6.01 (d, 1H), 4.55 (s, 1H), 4.18-4.10 (m, 2H), 3.04-2.95 (m, 2H), 2.19-2.10 (m, 2H), 1.45-1.35 (m, 2H) | 490.1527 |
| 51 | 1-(Pyridin-3-yl)-3-(1-(4-(4-(trifluoromethyl)phenoxy)pyridin-2-yl)piperidin-4-yl)thiourea | 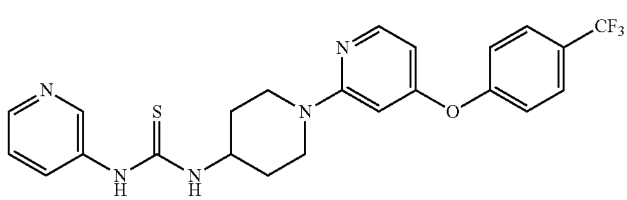 [SMILES: FC(F)(F)c1ccc(Oc2ccnc(N3CCC(NC(=S)Nc4cccnc4)CC3)c2)cc1] | δ 8.50-8.44 (m, 2H), 8.35 (s, 1H), 8.05 (d, 1H), 7.72 (d, 1H), 7.64-7.59 (m, 2H), 7.34 (d, 1H), 7.16-7.10 (m, 2H), 6.23 (d, 1H), 6.20 (d, 1H), 6.11 (d, 1H), 4.55 (s, 1H), 4.19-4.13 (m, 2H), 3.05-2.97 (m, 2H), 2.19-2.12 (m, 2H), 1.47-1.35 (m, 2H) | 474.1577 |

-continued

| Ex | Name | Structure | ¹H NMR (CDCl₃, 600 MHz) | HRMS [M + H]⁺ |
|---|---|---|---|---|
| 52 | 1-(Pyridin-3-yl)-3-(1-(4-(3-(trifluoromethyl)phenoxy)pyridin-2-yl)piperidin-4-yl)thiourea | 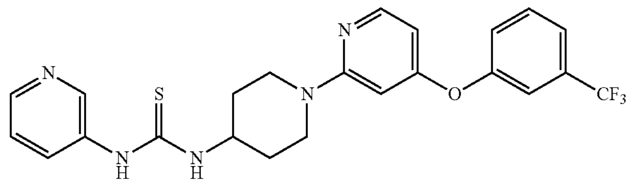 [SMILES: FC(F)(F)c1cccc(Oc2ccnc(N3CCC(NC(=S)Nc4cccnc4)CC3)c2)c1] | δ 8.48-8.43 (m, 2H), 8.37 (s, 1H), 8.04 (d, 1H), 7.75-7.70 (m, 1H), 7.49 (t, 1H), 7.46-7.43 (m, 1H), 7.35-7.30 (m, 2H), 7.25-7.22 (m, 1H), 6.21 (d, 1H), 6.16 (d, 1H), 6.13 (d, 1H), 4.55 (s, 1H), 4.18-4.11 (m, 2H), 3.05-2.96 (m, 2H), 2.19-2.11 (m, 2H), 1.45-1.36 (m, 2H) | 474.1582 |
| 53 | 1-(Pyridin-3-yl)-3-(1-(4-(2-(trifluoromethyl)phenoxy)pyridin-2-yl)piperidin-4-yl)thiourea | 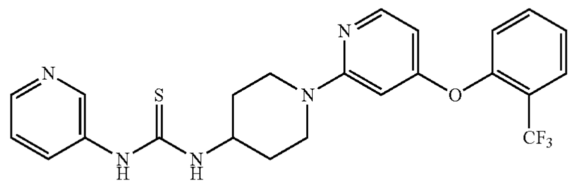 [SMILES: FC(F)(F)c1ccccc1Oc1ccnc(N2CCC(NC(=S)Nc3cccnc3)CC2)c1] | δ 8.53-8.35 (m, 3H), 8.05-8.01 (m, 1H), 7.77-7.67 (m, 2H), 7.56-7.51 (m, 1H), 7.36-7.25 (m, 2H), 7.08 (d, 1H), 6.28-6.13 (m, 3H), 4.54 (s, 1H), 4.22-4.07 (m, 2H), 3.08-2.96 (m, 2H), 2.21-2.09 (m, 2H), 1.49-1.36 (m, 2H) | 474.1579 |
| 54 | 1-(1-(4-(3-Chloro-4-(trifluoromethoxy)phenoxy)pyridin-2-yl)piperidin-4-yl)-3-(pyridin-3-yl)thiourea | 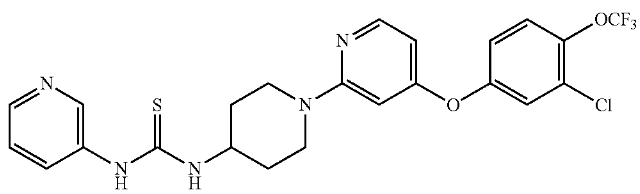 | δ 8.53-8.47 (m, 2H), 8.06 (d, 1H), 7.95 (s, 1H), 7.65 (d, 1H), 7.37 (d, 1H), 7.34-7.29 (m, 1H), 7.17 (d, 1H), 6.98 (d, 1H), 6.23-6.21 (m, 1H), 6.18 (d, 1H), 5.89 (d, 1H), 4.57 (s, 1H), 4.23-4.14 (m, 2H), 3.07-2.96 (m, 2H), 2.22-2.14 (m, 2H), 1.47-1.36 (m, 2H) | 524.1142 |
| 55 | 1-(1-(4-(2-Chloro-4-(trifluoromethoxy)phenoxy)pyridin-2-yl)piperidin-4-yl)-3-(pyridin-3-yl)thiourea | 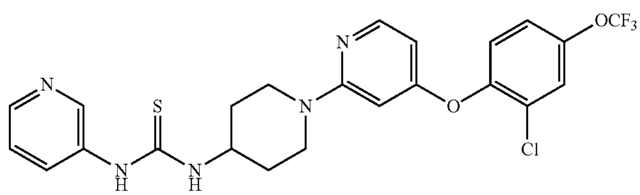 [SMILES: FC(F)(F)Oc1ccc(Oc2ccnc(N3CCC(NC(=S)Nc4cccnc4)CC3)c2)c(Cl)c1] | δ 8.50-8.47 (m, 2H), 8.14 (s, 1H), 8.02 (d, 1H), 7.70-7.66 (m, 1H), 7.38-7.33 (m, 2H), 7.17-7.12 (m, 2H), 6.18 (d, 1H), 6.07 (d, 1H), 5.99 (d, 1H), 4.55 (s, 1H), 4.19-4.13 (m, 2H), 3.06-2.94 (m, 2H), 2.21-2.13 (m, 2H), 1.46-1.37 (m, 2H) | 524.1142 |
| 56 | 1-(1-(4-(3-Fluoro-4-(trifluoromethoxy)phenoxy)pyridin-2-yl)piperidin-4-yl)-3-(pyridin-3-yl)thiourea | 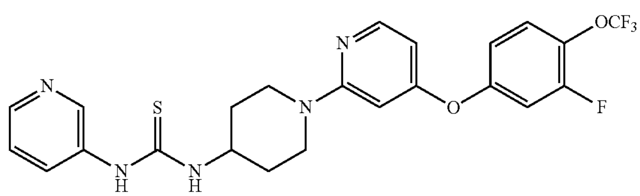 [SMILES: Fc1cc(Oc2ccnc(N3CCC(NC(=S)Nc4cccnc4)CC3)c2)ccc1OC(F)(F)F] | δ 8.55-8.49 (m, 2H), 8.07 (d, 1H), 7.85 (s, 1H), 7.66-7.61 (m, 1H), 7.37 (d, 1H), 7.32-7.28 (m, 2H), 6.91 (d, 1H), 6.85 (d, 1H), 6.23 (d, 1H), 6.19 (d, 1H), 5.84 (d, 1H), 4.57 (s, 1H), 4.22-4.15 (m, 2H), 3.07-2.99 (m, 2H), 2.21-2.14 (m, 2H), 1.47-1.37 (m, 2H) | 508.1438 |
| 57 | 1-(1-(4-(4-Chloro-3-(trifluoromethoxy)phenoxy)pyridin-2-yl)piperidin-4-yl)-3-(pyridin-3-yl)thiourea | 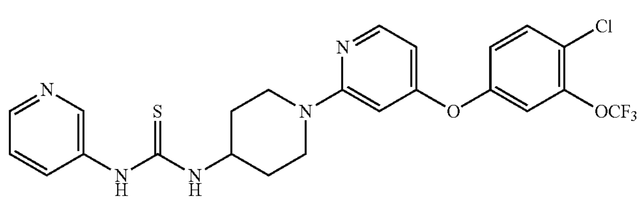 [SMILES: FC(F)(F)Oc1cc(Oc2ccnc(N3CCC(NC(=S)Nc4cccnc4)CC3)c2)ccc1Cl] | δ 8.52-8.47 (m, 2H), 8.14 (s, 1H), 8.06 (d, 1H), 7.71-7.67 (m, 1H), 7.46 (d, 1H), 7.38-7.33 (m, 1H), 7.07-7.05 (m, 1H), 6.96 (d, 1H), 6.21-6.17 (m, 2H), 5.99 (d, 1H), 4.56 (s, 1H), 4.21-4.13 (m, 2H), 3.06-2.96 (m, 2H), 2.22-2.11 (m, 2H), 1.47-1.34 (m, 2H) | 524.1137 |
| 58 | 1-(1-(4-(2-Fluoro-5-(trifluoromethoxy)phenoxy)pyridin-2-yl)piperidin-4-yl)-3-(pyridin-3-yl)thiourea | 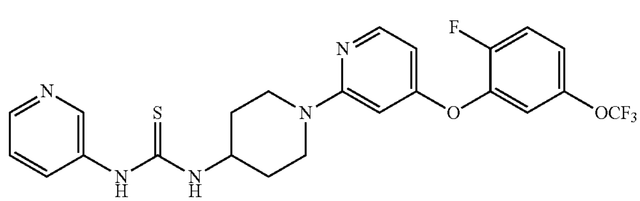 [SMILES: Fc1ccc(OC(F)(F)F)cc1Oc1ccnc(N2CCC(NC(=S)Nc3cccnc3)CC2)c1] | δ 8.55-8.47 (m, 2H), 8.05 (d, 1H), 7.93 (s, 1H), 7.65 (d, 1H), 7.40-7.34 (m, 1H), 7.29-7.20 (m, 2H), 7.10-7.02 (m, 2H), 6.24-6.12 (m, 2H), 5.92-5.85 (m, 1H), 4.56 (s, 1H), 4.23-4.14 (m, 2H), 3.09-2.97 (m, 2H), 2.24-2.12 (m, 2H), 1.47-1.35 (m, 2H) | 508.1431 |

-continued

| Ex | Name | Structure | ¹H NMR (CDCl₃, 600 MHz) | HRMS [M + H]⁺ |
|---|---|---|---|---|
| 59 | 1-(Pyridin-3-yl)-3-(1-(4-(4-(trifluoromethoxy)phenoxy)-3-(trifluoromethyl)pyridin-2-yl)piperidin-4-yl)thiourea | 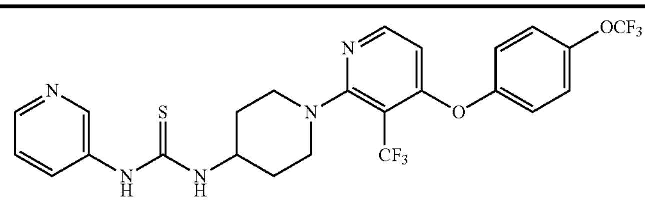 | δ 8.54-8.46 (m, 2H), 8.36 (s, 1H), 8.11 (d, 1H), 7.73 (d, 1H), 7.37 (d, 1H), 7.27-7.22 (m, 2H), 7.11-7.06 (m, 2H), 6.22 (d, 1H), 6.11 (d, 1H), 4.50 (s, 1H), 3.73-3.63 (m, 2H), 3.12-3.02 (m, 2H), 2.23-2.12 (m, 2H), 1.62-1.51 (m, 2H) | 558.1398 |
| 60 | 1-(Pyridin-3-yl)-3-(1-(4-(4-(trifluoromethoxy)phenoxy)-6-(trifluoromethyl)pyridin-2-yl)piperidin-4-yl)thiourea | 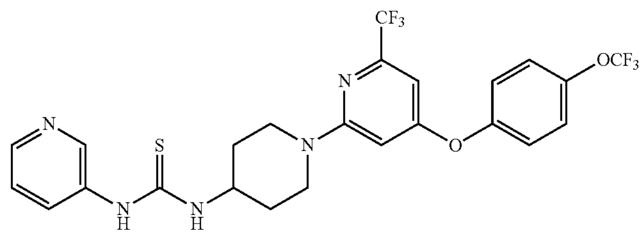 [SMILES: FC(F)(F)Oc1ccc(Oc2cc(N3CCC(NC(=S)Nc4cccnc4)CC3)nc(C(F)(F)F)c2)cc1] | δ 8.55-8.49 (m, 2H), 7.86 (s, 1H), 7.67 (d, 1H), 8.42-8.34 (m, 1H), 7.31-7.24 (m, 2H), 7.13-7.03 (m, 2H), 6.52-6.46 (m, 1H), 6.28-6.23 (m, 1H), 5.91-5.83 (s, 1H), 4.57 (s, 1H), 4.27-4.17 (m, 2H), 3.10-2.98 (m, 2H), 2.22-2.14 (m, 2H), 1.46-1.33 (m, 2H) | 558.1403 |
| 61 | 1-(1-(4-(4-Pentylphenoxy)pyridin-2-yl)piperidin-4-yl)-3-(pyridin-3-yl)thiourea | 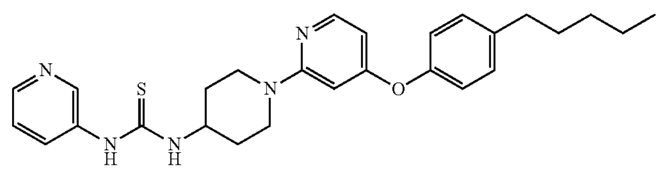 [SMILES: CCCCCc1ccc(Oc2ccnc(N3CCC(NC(=S)Nc4cccnc4)CC3)c2)cc1] | δ 8.53-8.46 (m, 2H), 8.01-7.91 (m, 2H), 7.70-7.63 (m, 1H), 7.38-7.33 (m, 1H), 7.20-7.15 (m, 2H), 6.99-6.92 (m, 2H), 6.20-6.14 (m, 2H), 5.93 (d, 1H), 4.54 (s, 1H), 4.16-4.07 (m, 2H), 3.04-2.95 (m, 2H), 2.63-2.57 (m, 2H), 2.17-2.11 (m, 2H), 1.66-1.59 (m, 2H), 1.46-1.28 (m, 6H), 0.90 (t, J = 7.0 Hz, 3H) | 476.2493 |
| 62 | 1-(1-(4-(4-(Difluoromethoxy)phenoxy)pyridin-2-yl)piperidin-4-yl)-3-(pyridin-3-yl)thiourea | 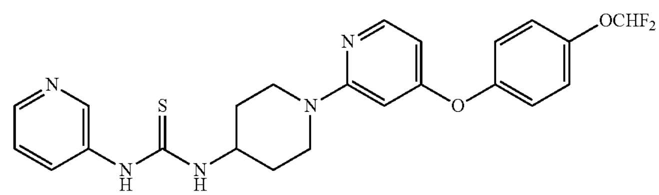 [SMILES: FC(F)Oc1ccc(Oc2ccnc(N3CCC(NC(=S)Nc4cccnc4)CC3)c2)cc1] | δ 8.49-8.43 (m, 2H), 8.35 (s, 1H), 8.01 (d, 1H), 7.73-7.69 (m, 1H), 7.33 (d, 1H), 7.16-7.12 (m, 2H), 7.16-7.03 (m, 2H), 6.50 (t, 1H), 6.17 (d, 1H), 6.15 (d, 1H), 6.11 (d, 1H), 4.53 (s, 1H), 4.16-4.09 (m, 2H), 3.03-2.94 (m, 2H), 2.18-2.09 (m, 2H), 1.45-1.34 (m, 2H) | 472.1620 |
| 63 | 1-(1-(3-Chloro-4-(4-chloro-3-(trifluoromethoxy)phenoxy)pyridin-2-yl)piperidin-4-yl)-3-(pyridin-3-yl)thiourea | 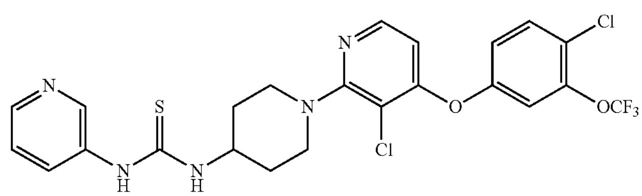 [SMILES: FC(F)(F)Oc1cc(Oc2ccnc(N3CCC(NC(=S)Nc4cccnc4)CC3)c2Cl)ccc1Cl] | δ 8.55-8.52 (m, 2H), 8.03 (d, 2H), 7.69-7.65 (m, 1H), 7.47 (d, 1H), 7.38-7.33 (m, 1H), 7.07-7.05 (m, 1H), 6.94 (d, 1H), 6.38 (d, 1H), 5.95 (d, 1H), 4.54 (s, 1H), 3.84-3.76 (m, 2H), 3.09-2.98 (m, 2H), 2.26-2.17 (m, 2H), 1.69-1.57 (m, 2H) | 558.0754 |
| 64 | 1-(1-(3-Chloro-4-(3-fluoro-4-(trifluoromethoxy)phenoxy)pyridin-2-yl)piperidin-4-yl)-3-(pyridin-3-yl)thiourea | 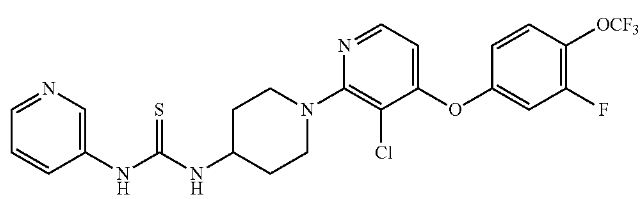 [SMILES: Fc1cc(Oc2ccnc(N3CCC(NC(=S)Nc4cccnc4)CC3)c2Cl)ccc1OC(F)(F)F] | δ 8.55-8.52 (m, 2H), 8.05 (d, 1H), 7.98 (s, 1H), 7.69-7.65 (d, 1H), 7.39 (d, 1H), 7.34-7.29 (m, 1H), 6.91 (d, 1H), 6.84 (d, 1H), 6.42 (d, 1H), 5.94 (d, 1H), 4.55 (s, 1H), 3.85-3.77 (m, 2H), 3.08-3.00 (m, 2H), 2.27-2.19 (m, 2H), 1.67-1.58 (m, 2H) | 542.1040 |
| 65 | 1-(1-(3-Chloro-4-(3-chloro-4-(trifluoromethoxy)phenoxy)pyridin-2-yl)piperidin-4-yl)-3-(pyridin-3-yl)thiourea | 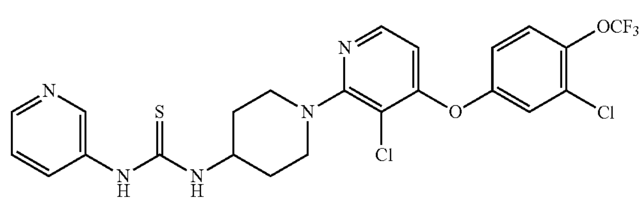 [SMILES: FC(F)(F)Oc1ccc(Oc2ccnc(N3CCC(NC(=S)Nc4cccnc4)CC3)c2Cl)cc1Cl] | δ 8.55-8.50 (m, 2H), 8.09 (s, 1H), 8.04 (d, 1H), 7.72-7.67 (m, 1H), 7.38 (d, 1H), 7.35-7.31 (m, 1H), 7.17 (d, 1H), 6.97 (d, 1H), 6.40 (d, 1H), 6.00 (d, 1H), 4.54 (s, 1H), 3.85-3.76 (m, 2H), 3.09-3.00 (m, 2H), 2.27-2.19 (m, 2H), 1.68-1.58 (m, 2H) | 558.0743 |

-continued

| Ex | Name | Structure | ¹H NMR (CDCl₃, 600 MHz) | HRMS [M + H]⁺ |
|---|---|---|---|---|
| 66 | 1-(1-(3-Chloro-4-(3-(trifluoromethoxy)phenoxy)pyridin-2-yl)piperidin-4-yl)-3-(pyridin-3-yl)thiourea | 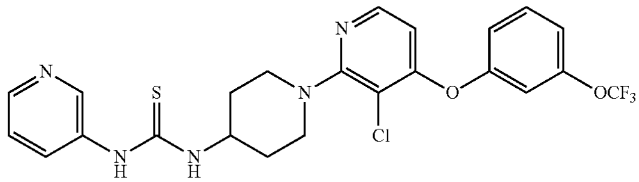 [SMILES: FC(F)(F)Oc1cccc(Oc2ccnc(N3CCC(NC(=S)Nc4cccnc4)CC3)c2Cl)c1] | δ 8.50 (s, 2H), 8.37 (s, 1H), 8.00 (d, 1H), 7.75 (d, 1H), 7.42-7.34 (m, 2H), 7.09-7.06 (m, 1H), 6.99-6.96 (m, 1H), 6.95-6.92 (m, 1H), 6.37 (d, 1H), 6.15 (s, 1H), 4.53 (s, 1H), 3.85-3.73 (m, 2H), 3.08-3.00 (m, 2H), 2.22-2.17 (m, 2H), 1.68-1.60 (m, 2H) | 524.1142 |
| 67 | 1-(1-(3-Chloro-4-(2-(trifluoromethoxy)phenoxy)pyridin-2-yl)piperidin-4-yl)-3-(pyridin-3-yl)thiourea | 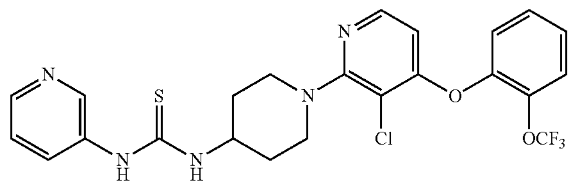 [SMILES: FC(F)(F)Oc1ccccc1Oc1ccnc(N2CCC(NC(=S)Nc3cccnc3)CC2)c1Cl] | δ 8.56-8.45 (d, 2H), 8.26 (s, 1H), 7.96 (d, 1H), 7.75-7.68 (m, 1H), 7.40-7.34 (m, 2H), 7.33-7.29 (m, 1H), 7.28-7.23 (m, 1H), 7.12 (d, 1H), 6.23 (d, 1H), 6.12-6.05 (d, 1H), 4.53 (s, 1H), 3.84-3.75 (m, 2H), 3.08-2.98 (m, 2H), 2.27-2.22 (m, 2H), 1.70-1.59 (m, 2H) | 524.1131 |
| 68 | 1-(1-(3-Chloro-4-(4-fluoro-3-(trifluoromethoxy)phenoxy)pyridin-2-yl)piperidin-4-yl)-3-(pyridin-3-yl)thiourea | 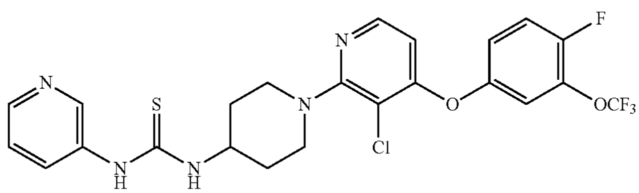 | δ 8.55-8.49 (m, 2H), 8.19 (s, 1H), 8.01 (d, 1H), 7.72-7.67 (d, 1H), 7.40-7.37 (m, 1H), 7.23 (t, 1H), 7.06-7.04 (m, 1H), 6.98 (m, 1H), 6.31 (d, 1H), 6.06-5.97 (m, 1H), 4.54 (s, 1H), 3.84-3.76 (m, 2H), 3.08-2.99 (m, 2H), 2.26-2.18 (m, 2H), 1.68-1.57 (m, 2H) | 542.1039 |
| 69 | 1-(1-(3-Chloro-4-(4-fluoro-2-methylphenoxy)pyridin-2-yl)piperidin-4-yl)-3-(pyridin-3-yl)thiourea | 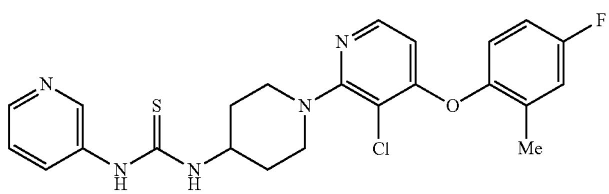 [SMILES: Cc1cc(F)ccc1Oc1ccnc(N2CCC(NC(=S)Nc3cccnc3)CC2)c1Cl] | δ 8.56-8.42 (m, 3H), 7.94 (d, 1H), 7.81-7.74 (m, 1H), 7.36 (d, 1H), 7.01 (t, 1H), 6.89 (d, 1H), 6.84 (d, 1H), 6.29 (d, 1H), 6.25 (d, 1H), 4.53 (s, 1H), 3.82-3.74 (m, 2H), 3.06-2.97 (m, 2H), 2.26 (s, 3H), 2.24-2.18 (m, 2H), 1.70-1.60 (m, 2H) | 472.1377 |
| 70 | 1-(1-(3-Chloro-4-(4-fluoro-3-methylphenoxy)pyridin-2-yl)piperidin-4-yl)-3-(pyridin-3-yl)thiourea | 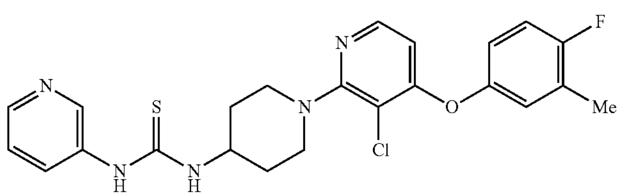 [SMILES: Cc1cc(Oc2ccnc(N3CCC(NC(=S)Nc4cccnc4)CC3)c2Cl)ccc1F] | δ 8.54-8.46 (m, 2H), 8.37 (s, 1H), 7.91 (d, 1H), 7.78-7.72 (m, 1H), 7.36 (d, 1H), 7.00-6.88 (m, 3H), 6.16 (s, 1H), 6.09 (d, 1H), 4.53 (s, 1H), 3.81-3.72 (m, 2H), 3.07-2.97 (m, 2H), 2.25-2.18 (m, 2H), 2.14 (s, 3H), 1.69-1.60 (m, 2H) | 472.1381 |
| 71 | 1-(1-(3-Cyano-4-(4-(trifluoromethoxy)phenoxy)pyridin-2-yl)piperidin-4-yl)-3-(pyridin-3-yl)thiourea | 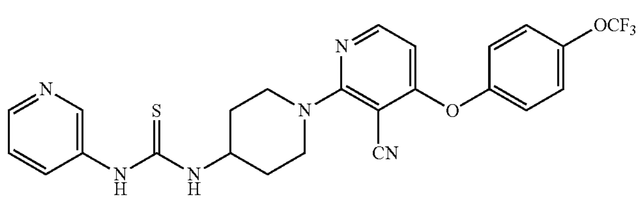 [SMILES: N#Cc1c(Oc2ccc(OC(F)(F)F)cc2)ccnc1N1CCC(NC(=S)Nc2cccnc2)CC1] | δ 8.85 (s, 1H), 8.53 (s, 1H), 8.40-8.34 (m, 1H), 8.08 (d, 1H), 8.01-7.97 (m, 1H), 7.32-7.25 (m, 3H), 7.16-7.12 (m, 2H), 6.93 (d, 1H), 6.02 (d, 1H), 4.64-4.53 (m, 1H), 4.35-4.27 (m, 2H), 3.27-3.18 (m, 2H), 2.26-2.19 (m, 2H), 1.66-1.56 (m, 2H) | 515.1484 |
| 72 | 1-(1-(3-Methyl-4-(4-(trifluoromethoxy)phenoxy)pyridin-2-yl)piperidin-4-yl)-3-(pyridin-3-yl)thiourea | 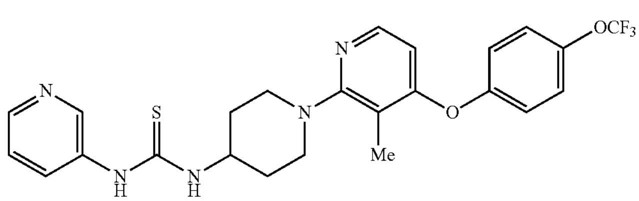 [SMILES: Cc1c(Oc2ccc(OC(F)(F)F)cc2)ccnc1N1CCC(NC(=S)Nc2cccnc2)CC1] | δ 8.58-8.49 (m, 2H), 8.04-7.98 (m, 1H), 7.89 (s, 1H), 7.72 (s, 1H), 7.39 (s, 1H), 7.22 (d, 2H), 7.02 (d, 2H), 6.33 (d, 1H), 6.06 (s, 1H), 4.53 (s, 1H), 3.49-3.34 (m, 2H), 3.09-2.93 (m, 2H), 2.29-2.08 (m, 5H), 1.50-1.32 (m, 2H) | 504.1677 |

-continued

| Ex | Name | Structure | ¹H NMR (CDCl₃, 600 MHz) | HRMS [M + H]⁺ |
|---|---|---|---|---|
| 73 | 1-(1-(3-Chloro-4-(2-methyl-4-(trifluoromethoxy)phenoxy)pyridin-2-yl)piperidin-4-yl)-3-(pyridin-3-yl)thiourea | 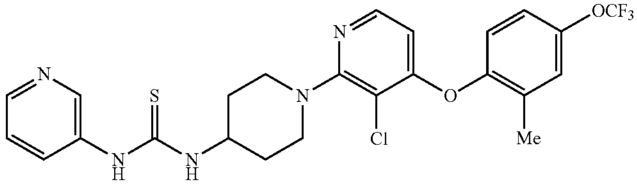 [SMILES: Cc1cc(OC(F)(F)F)ccc1Oc1ccnc(N2CCC(NC(=S)Nc3cccnc3)CC2)c1Cl] | δ 8.54-8.48 (m, 2H), 8.39 (s, 1H), 7.94 (d, 1H), 7.76-7.70 (m, 1H), 7.36 (d, 1H), 7.15-7.12 (m, 1H), 7.09-7.05 (m, 1H), 6.98 (d, 1H), 6.14 (d, 2H), 4.54 (s, 1H), 3.83-3.75 (m, 2H), 3.07-2.97 (m, 2H), 2.25-2.19 (m, 2H), 2.18 (s, 3H), 1.70-1.58 (m, 2H) | 538.1290 |
| 74 | 1-(1-(4-(4-Methoxyphenoxy)pyridin-2-yl)piperidin-4-yl)-3-(pyridin-3-yl)thiourea | 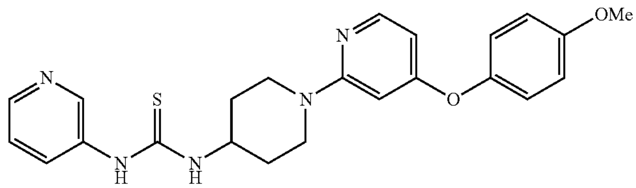 [SMILES: COc1ccc(Oc2ccnc(N3CCC(NC(=S)Nc4cccnc4)CC3)c2)cc1] | δ 8.47-8.32 (m, 3H), 7.97 (d, 1H), 7.78-7.71 (m, 1H), 7.32 (d, 1H), 7.00-6.97 (m, 2H), 6.92-6.88 (m, 2H), 6.20 (d, 1H), 6.15-6.12 (m, 2H), 4.51 (s, 1H), 4.13-4.05 (m, 2H), 3.81 (s, 3H), 3.00-2.93 (m, 2H), 2.15-2.09 (m, 2H), 1.44-1.34 (m, 2H) | 436.1814 |
| 75 | 1-(Pyridin-3-yl)-3-(1-(4-(p-tolyloxy)pyridin-2-yl)piperidin-4-yl)thiourea | 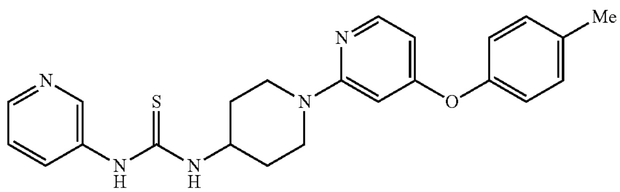 [SMILES: Cc1ccc(Oc2ccnc(N3CCC(NC(=S)Nc4cccnc4)CC3)c2)cc1] | δ 8.50-8.46 (m, 2H), 8.09 (s, 1H), 8.00-7.95 (m, 1H), 7.72-7.67 (m, 1H), 7.35 (d, 1H), 7.19-7.15 (m, 2H), 6.96-6.93 (m, 2H), 6.18-6.15 (m, 2H), 6.02 (d, J = 8.0 Hz, 1H), 4.52 (s, 1H), 4.15-4.08 (m, 2H), 3.03-2.94 (m, 2H), 2.36 (s, 3H), 2.17-2.10 (m, 2H), 1.45-1.34 (m, 2H) | 420.1858 |
| 76 | 1-(1-(4-Acetylpyridin-2-yl)piperidin-4-yl)-3-(pyridin-3-yl)thiourea | 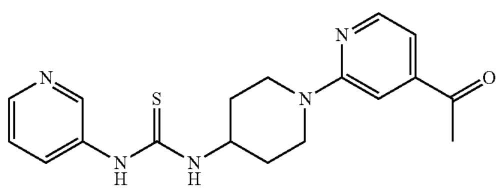 [SMILES: CC(=O)c1ccnc(N2CCC(NC(=S)Nc3cccnc3)CC2)c1] | δ 8.48-8.43 (m, 2H), 8.37 (s, 1H), 8.27 (d, 1H), 7.72-7.67 (m, 1H), 7.34-7.30 (m, 1H), 7.06 (s, 1H), 6.97-6.94 (m, 1H), 6.10 (d, 1H), 4.57 (s, 1H), 4.32-4.25 (m, 2H), 3.10-3.01 (m, 2H), 2.54 (s, 3H), 2.21-2.15 (m, 2H), 1.46-1.37 (m, 2H) | 356.1546 |
| 77 | 1-(1-(3-Chloro-5-(trifluoromethyl)pyridin-2-yl)piperidin-4-yl)-3-(pyridin-3-yl)urea | 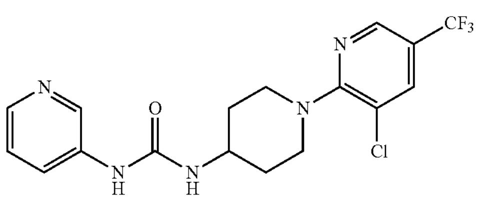 [SMILES: O=C(Nc1cccnc1)NC1CCN(c2ncc(C(F)(F)F)cc2Cl)CC1] | δ 8.37 (s, 2H), 8.25 (d, 1H), 8.01 (d, 1H), 7.74 (d, 1H), 7.26-7.24 (m, 1H), 7.19 (s, 1H), 5.10 (t, 1H), 3.99-3.93 (m, 3H), 3.05 (t, 2H), 2.15-2.05 (m, 2H), 1.58 (d, 2H) | 400.1163 |
| 78 | 1-(Pyridin-3-yl)-3-(1-(5-(trifluoromethyl)pyrimidin-2-yl)piperidin-4-yl)thiourea | 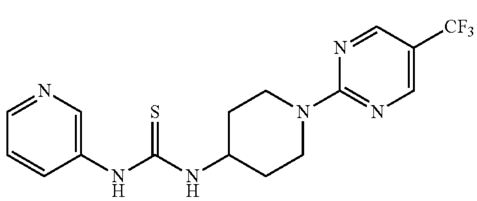 [SMILES: FC(F)(F)c1cnc(N2CCC(NC(=S)Nc3cccnc3)CC2)nc1] | δ 8.55 (d, 1H), 8.52 (d, 1H), 8.46-8.45 (m, 2H), 7.62-7.57 (m, 2H), 7.38 (d, 1H), 5.71 (d, 1H), 4.82-4.77 (m, 2H), 4.69-4.61 (m, 1H), 3.16-3.08 (m, 2H), 2.25-2.03 (m, 2H), 1.39-1.31 (m, 2H) | 382.1270 |
| 79 | 1-(Pyridin-3-yl)-3-(1-(6-(trifluoromethyl)pyridazin-3-yl)piperidin-4-yl)thiourea | 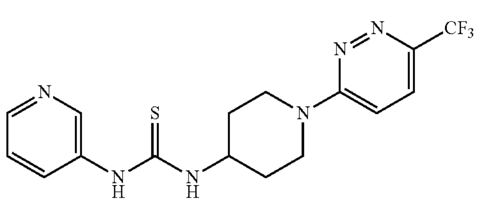 [SMILES: FC(F)(F)c1ccc(N2CCC(NC(=S)Nc3cccnc3)CC2)nn1] | δ 8.52-8.40 (m, 2H), 8.05 (s, 1H), 7.76 (d, 1H), 7.46 (d, 1H), 7.33 (d, 1H), 6.95 (d, 1H), 6.26 (s, 1H), 4.70 (S, 1H), 4.46 (d, 2H), 3.21 (t, 2H), 2.26 (d, 2H), 1.49-1.40 (m, 2H) | 382.1271 |

| Ex | Name | Structure | ¹H NMR (CDCl₃, 600 MHz) | HRMS [M + H]⁺ |
|---|---|---|---|---|
| 80 | 1-(1-(3-Chloro-5-(trifluoromethyl)pyridin-2-yl)azepan-4-yl)-3-(pyridin-3-yl)thiourea | 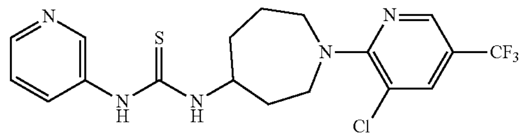 [SMILES: FC(F)(F)c1cnc(N2CCCC(NC(=S)Nc3cccnc3)CC2)c(Cl)c1] | δ 8.44 (d, 1H), 8.40 (s, 1H), 8.34 (d, 1H), 8.26-8.24 (m, 1H), 7.65 (d, J = 2.1 Hz, 1H), 7.58 (d, 1H), 7.16 (d, 1H), 6.34-6.25 (m, 1H), 4.68 (s, 1H), 3.85-3.80 (m, 1H), 3.77-3.73 (m, 1H), 3.52-3.43 (m, 2H), 2.23-2.18 (m, 1H), 2.05-1.84 (m, 4H), 1.79-1.71 (m, 1H) | 430.1081 |
| 81 | 1-(5-((3-Chloro-5-(trifluoromethyl)pyridin-2-yl)amino)pentyl)-3-(pyridin-3-yl)thiourea | 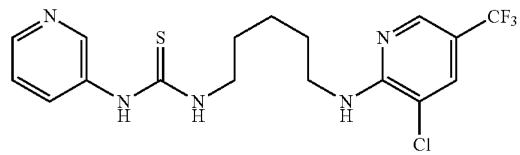 [SMILES: FC(F)(F)c1cnc(NCCCCCNC(=S)Nc2cccnc2)c(Cl)c1] | δ 8.51 (d, 1H), 8.48 (d, 1H), 8.25-8.23 (m, 1H), 8.20 (s, 1H), 7.72-7.66 (m, 1H), 7.60 (d, 1H), 7.35 (d, 1H), 6.19 (s, 1H), 5.36 (t, 1H), 3.69-3.58 (m, 2H), 3.52-3.48 (m, 2H), 1.70-1.62 (m, 2H), 1.45-1.39 (m, 2H) | 418.1089 |
| 82 | 1-(1-(3-Chloro-5-(trifluoromethyl)pyridin-2-yl)piperidin-4-yl)-1-methyl-3-(pyridin-3-yl)thiourea | 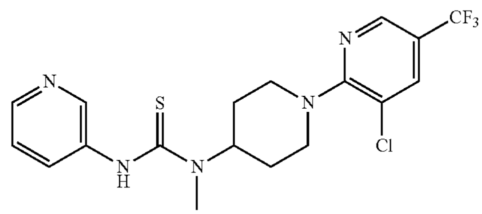 [SMILES: CN(C(=S)Nc1cccnc1)C1CCN(c2ncc(C(F)(F)F)cc2Cl)CC1] | δ 8.45 (d, 1H), 8.40-8.38 (m, 2H), 7.84 (d, 1H), 7.76 (d, 1H), 7.41 (s, 1H), 7.29 (d, 1H), 5.57-5.47 (m, 1H), 4.21-4.15 (m, 2H), 3.14 (S, 3H), 3.08-3.00 (m, 2H), 1.98-1.84 (m, 4H) | 430.1087 |
| 83 | 1-(4-((3-Chloro-5-(trifluoromethyl)pyridin-2-yl)amino)butyl)-3-(pyridin-3-yl)thiourea | 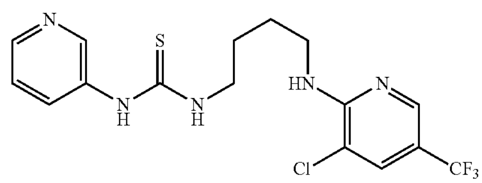 [SMILES: FC(F)(F)c1cnc(NCCCCNC(=S)Nc2cccnc2)c(Cl)c1] | δ 8.49 (d, 1H), 8.43 (d, 1H), 8.18 (s, 1H), 7.72 (d, 1H), 7.59 (d, 1H), 7.32 (d, 1H), 3.71-3.63 (m, 2H), 3.56-3.51 (m, 2H), 1.73-1.64 (m, 4H) | 404.0933 |
| 84 | 1-(6-((3-Chloro-5-(trifluoromethyl)pyridin-2-yl)amino)hexyl)-3-(pyridin-3-yl)thiourea | 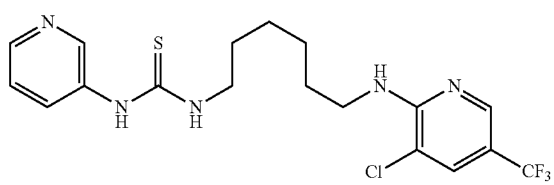 [SMILES: FC(F)(F)c1cnc(NCCCCCCNC(=S)Nc2cccnc2)c(Cl)c1] | δ 8.51-8.49 (m, 1H), 8.47 (d, 1H), 8.25-8.23 (m, 2H), 7.71 (s, 1H), 7.60 (d, 1H), 7.34 (d, 1H), 6.21 (s, 1H), 5.36 (t, 1H), 3.61 (s, 2H), 3.52-3.46 (m, 2H), 1.69-1.57 (m, 4H), 1.45-1.34 (m, 4H) | 432.1244 |
| 85 | 1-((1R,5S)-8-(3-Chloro-5-(trifluoromethyl)pyridin-2-yl)-8-azabicyclo[3.2.1]octan-3-yl)-3-(pyridin-3-yl)thiourea | 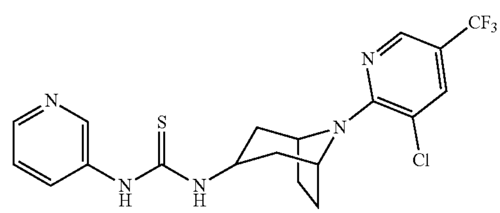 [SMILES: FC(F)(F)c1cnc(N2C3CCC2CC(NC(=S)Nc2cccnc2)C3)c(Cl)c1] | δ 8.47-8.44 (m, 2H), 8.27 (s, 1H), 8.12 (s, 1H), 7.66 (s, 1H), 7.59 (d, 1H), 7.34 (d, 1H), 5.83-5.74 (m, 1H), 4.99-4.89 (m, 1H), 4.87 (s, 2H), 2.19-2.11 (m, 2H), 2.08-1.99 (m, 2H), 1.95-1.88 (m, 2H), 1.66-1.57 (m, 2H) | 442.1089 |

II. Biological Evaluation

Compounds were tested to assess their ABHD12 activity using the following assays.

Gel-Based Competitive ABPP for In Vitro Inhibitor Treatment of Proteomes:

Gel-based ABPP assays were performed as previously reported (Bachovchin, D. A. et al. Superfamily-wide portrait of serine hydrolase inhibition achieved by library-versus-library screening. *Proc. Natl. Acad. Sci. U. S. A.* 2010, 107, 20941-20946). Cell or tissue proteomes (50 μL, 1 mg/mL) were treated with either FP-Rh (1 μM final concentration) or JJH350 (2 μM final concentration) for 45 min at 37° C. For FP-Rh labeled samples, the reactions were quenched by adding 20 μL of 4× SDS-PAGE loading buffer. The 30 μL of the quenched samples were loaded on gel for analysis. For (S)-1,3-dioxo-7-(4-phenoxybenzoyl)hexahydroimidazo[1,5-a]pyrazin-2(3H)-yl 4-(4-(prop-2-yn-1-yloxy)phenyl)piperazine-1-carboxylate (JJH350)-labeled samples, copper-catalyzed azide-alkyne cycloaddition (CuAAC) was used for visualizing the labeled proteins following the reported protocol. Briefly, rhodamine-PEG3-N₃ (1 μL/reaction, 1.25 mM in DMSO), CuSO₄ (1 μL/reaction, 50 mM in H₂O), TBTA (3 μL/reaction, 1.7 mM in DMSO/t-BuOH [1:4, v/v]) and tris(2-carboxyethyi)phosphine (TCEP) (1 μL/reaction, 50 mM in H₂O, freshly prepared) were premixed. 6 μL of this click reagent mixture was immediately added to each JJH350-labeled samples (50 μL, 1 mg/mL) and incubated for 1 h at room temperature. The reactions were quenched by adding 20 μL of 4× SDS-PAGE loading buffer. The 40 μL of the quenched samples were loaded on a gel for analysis.

After separation by SDS-PAGE (10% acrylamide), samples were visualized by in-gel fluorescence scanning using the ChemiDoc MP system (Bio-Rad). Band intensities were quantified using the Image Lab (5.2.1) software (Bio-Rad).

Gel-Based Competitive ABPP for In Vivo Inhibitor Treatment:

Tissues from mice treated with inhibitors were dounce-homogenized in DPBS (1 mL for a half brain, spleen and liver, and 1.5 mL for lung) followed by low-speed spin (1,400× g, 3 min, 4° C.) to remove debris. For FP-Rh labeling, 2 μL of 50 μM FP-Rh was added to 50 μL of the whole tissue lysate obtained above (2 μM final) and incubated for 20 min at room temperature. For JJH350 labeling, 1 μL of 500 μM JJH350 was added to 50 μL of the whole tissue lysate obtained above (10 μM final) and incubated for 30 min at room temperature. 1.5 mL of cold DPBS was added to each probe-labeled samples and spun at 16,000× g for 45 min at 4° C. The resulting membrane pellet was resuspended in cold DPBS, and protein concentrations were adjusted to 1 mg/mL using the Bio-Rad DC protein assay kit. For FP-Rh labeled samples, the reactions were quenched by adding 20 μL of 4× SDS-PAGE loading buffer, and the 30 μL of the quenched samples were loaded on a gel for analysis. For (S)-1,3-dioxo-7-(4-phenoxybenzoyl)hexahydroimidazo[1,5-a]pyrazin-2(3H)-yl 4-(4-(prop-2-yn-1-yloxy)phenyl)piperazine-1-carboxylate (JJH350)-labeled samples, CuAAC reactions were performed as described above and the reactions were quenched by adding 20 μL of 4× SDS-PAGE loading buffer. The 40 μL of the quenched samples were loaded on gel for analysis.

Lyso-PS Hydrolysis Assay:

The lyso-PS lipase activity of ABHD12 was determined as previously described (Blankman, J. L., Long, J. Z., Trauger, S. A., Siuzdak, G. & Cravatt, B. F. ABHD12 controls brain lysophosphatidylserine pathways that are deregulated in a murine model of the neurodegenerative disease PHARC. Proc. Natl. Acad. Sci. U. S. A. 110, 1500-1505, doi:10.1073/pnas.1217121110 (2013)) with some minor modifications. The proteome concentrations were adjusted to 0.25 mg/mL (ABHD12-overexpressing HEK293T membrane) or 0.5 mg/mL (mouse brain membrane) in Dulbecco's phosphate-buffered saline (DPBS) (80 μL/reaction). 20 μL of 500 μM 17:1 lyso-PS in DPBS was added to each reaction (100 μM final concentration) and incubated at 37° C. After 30 min, the reaction was quenched with 400 μL of 2:1 CHCl$_3$/MeOH (v/v) with 1 nmol 15:0 FFA as an internal standard. The mixture was vortexed and centrifuged at 1,400× g to separate the aqueous and organic phase. The organic phase was analyzed by LC-MS (1200 LC/MSD, Agilent Technologies). The separation of the analyte was achieved using a 50 mm×4.6 mm 5 μm Gemini C18 column (Phenomenex) coupled to a guard column (Gemini: C18: 4×3 mm). The LC solvents were as follows: buffer A, H$_2$:MeOH (95:5, v/v) with 0.1% NH$_4$OH (v/v); and buffer B, iPrOH:MeOH:H$_2$O (60:3 5:5, v/v/v) with 0.1% NH$_4$OH (v/v). The LC method consisted of 0.1 mL/min 20% buffer B for 1.0 min, 0.4 ml/min isocratic mode of 100% buffer B over 7 min and equilibration with 0.5 mL/min 100% buffer A for 3 min. The MS analyses were performed using an electrospray ionization source (ESI) in negative ion mode to measure product formation. MS data were acquired in selected ion monitoring mode at m/z 267.20 for 17:1 FFA and m/z 241.20 for 15:0 FFA.

Percent enzyme inhibition at 10 μM and IC$_{50}$ data from these assays are shown in Table 1.

TABLE 1

| Ex | % Inhibition @ 10 μM (ABPP gel_JJH350 probe vs brain mem) | IC$_{50}$ (ABPP gel_JJH350 probe vs brain mem) | IC$_{50}$ (Substrate-based assay_ABHD12-overexpressed HEK lysate) |
|---|---|---|---|
| 1 | A | * | * |
| 2 | A | ** | ** |
| 3 | A | *** | *** |
| 4 |   | *** | *** |
| 5 |   |   | *** |
| 6 |   | ** |   |
| 7 |   |   |   |
| 8 | A |   |   |
| 9 | A |   |   |
| 10 | C (at 2 uM) |   |   |
| 11 | A |   |   |
| 12 | A |   |   |
| 13 | A |   |   |
| 14 | A | * | * |
| 15 | A | ** | * |
| 16 | C | * | * |
| 17 | B |   |   |
| 18 | A |   |   |
| 19 | D |   |   |
| 20 | B (at 2 uM) |   |   |
| 21 | A |   |   |
| 22 | A |   |   |
| 23 | A |   |   |
| 24 | B |   |   |
| 25 | A | * | * |
| 26 | A | ** | ** |
| 27 | A | ** | ** |
| 28 | A | * | * |
| 29 | A | ** | ** |
| 30 | A | * |   |
| 31 | A | * |   |
| 32 | B |   |   |
| 33 | A |   |   |
| 34 | A |   |   |
| 35 | A |   |   |
| 36 | B |   |   |
| 37 | A | * |   |
| 38 | A |   |   |
| 39 | A |   |   |
| 40 | A | * | * |
| 41 | A | * | * |
| 42 | A |   |   |
| 43 | A |   |   |
| 44 | B | * |   |
| 45 | C | * |   |
| 46 | D |   |   |
| 47 | A |   |   |
| 48 | A |   |   |
| 49 | A |   |   |
| 50 | A |   |   |
| 51 | A | ** | ** |
| 52 | A |   |   |
| 53 | A |   |   |
| 54 | A |   | ** |
| 55 | A |   |   |
| 56 | A |   |   |
| 57 | A | ** | ** |
| 58 | A |   |   |
| 59 | A | * | * |
| 60 | D |   |   |
| 61 | A |   |   |
| 62 | A |   |   |
| 63 |   | *** |   |
| 64 |   | *** |   |
| 65 |   | *** | *** |
| 66 |   | *** | ** |
| 67 |   | *** | ** |
| 68 |   | *** |   |
| 69 |   | ** |   |
| 70 |   | ** |   |

TABLE 1-continued

| Ex | % Inhibition @ 10 μM (ABPP gel_JJH350 probe vs brain mem) | IC$_{50}$ (ABPP gel_JJH350 probe vs brain mem) | IC$_{50}$ (Substrate-based assay_ABHD12-overexpressed HEK lysate) |
|---|---|---|---|
| 71 |   | ** | ** |
| 72 |   | *** | *** |
| 73 |   | *** |   |
| 74 |   | * | * |
| 75 |   | * |   |
| 76 | C |   | * |
| 77 | C |   |   |
| 78 | B |   |   |
| 79 | D |   |   |
| 80 | B |   |   |
| 81 | A |   |   |
| 82 | B |   |   |
| 83 | C |   |   |
| 84 | B |   |   |
| 85 | B |   |   |

*** IC$_{50}$ is less than or equal to 100 nM;
** IC$_{50}$ is greater than 100 nM and less than 1 μM;
* IC$_{50}$ is greater than or equal to 1 μM and less or equal to 25 μM.
A = % inhibition is greater than or equal to 75%;
B = % inhibition is greater than or equal to 50% and less than 75%;
C = % inhibition is greater than or equal to 25% and less than 50%;
D = % inhibition is greater than or equal to 0% and less than 25%.

What is claimed is:

1. A compound of Formula (I):

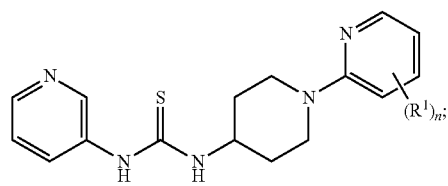

Formula (I)

wherein:

each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;

each $R^2$ is independently $C_{1-6}$alkyl;

each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;

each $R^4$ is independently $C_{1-6}$alkyl; and n is 0, 1, 2, or 3;

or a solvate, N-oxide, stereoisomer, or pharmaceutically acceptable salt thereof.

2. A compound of Formula (II):

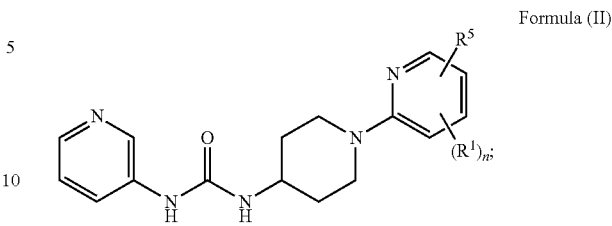

Formula (II)

wherein:

each $R^1$ is independently selected from halogen, —CN, $C_{1-6}$alkyl, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy;

each $R^2$ is independently $C_{1-6}$alkyl;

each $R^3$ is independently selected from H, $C_{1-6}$alkyl, $C_{1-6}$haloalkyl, $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl, wherein $C_{3-6}$cycloalkyl, -$C_{1-6}$alkyl-$C_{3-6}$cycloalkyl, $C_{2-9}$heterocycloalkyl, phenyl, and -$C_{1-6}$alkyl-phenyl are optionally substituted with 1, 2, or 3 substituents independently selected from halogen, $C_{1-6}$alkyl, $C_{1-6}$alkynyl, $C_{1-6}$haloalkyl, $C_{1-6}$alkoxy, $C_{1-6}$haloalkoxy, and —C(O)O$R^4$;

each $R^4$ is independently $C_{1-6}$alkyl;

$R^5$ is selected from halogen, —CN, $C_{1-6}$alkenyl, $C_{1-6}$alkynyl, $C_{1-6}$haloalkyl, —C(O)$R^2$, —O$R^3$, and phenyl optionally substituted with 1, 2, or 3 substituents independently selected from halogen, $C_{1-6}$alkyl, $C_{1-6}$haloalkyl, $C_{1-6}$alkoxy, and $C_{1-6}$haloalkoxy; and n is 0, 1, 2, or 3;

or a solvate, N-oxide, stereoisomer, or pharmaceutically acceptable salt thereof.

3. The compound of claim 2, or a solvate, N-oxide, stereoisomer, or pharmaceutically acceptable salt thereof, wherein $R^5$ is selected from halogen, —CN, $C_{1-6}$alkynyl, $C_{1-6}$haloalkyl, —C(O)$R^2$, —O$R^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy.

4. The compound of claim 3, or a solvate, N-oxide, stereoisomer, or pharmaceutically acceptable salt thereof, wherein $R^5$ is selected from halogen, $C_{1-6}$haloalkyl, —O$R^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy.

5. The compound of claim 1, or a solvate, N-oxide, stereoisomer, or pharmaceutically acceptable salt thereof, wherein each $R^1$ is independently selected from halogen, —CN, $C_{1-6}$alkyl, $C_{1-6}$alkynyl, $C_{1-6}$haloalkyl, —C(O)$R^2$, —O$R^3$, and phenyl optionally substituted with 1 or 2 substituents independently selected from halogen, $C_{1-6}$alkyl, $C_{1-6}$haloalkyl, $C_{1-6}$alkoxy, and $C_{1-6}$haloalkoxy.

6. The compound of claim 5, or a solvate, N-oxide, stereoisomer, or pharmaceutically acceptable salt thereof, wherein each $R^1$ is independently selected from halogen, $C_{1-6}$alkyl, $C_{1-6}$haloalkyl, —O$R^3$, and phenyl substituted with 1 or 2 substituents independently selected from halogen, $C_{1-6}$alkyl, $C_{1-6}$haloalkyl, $C_{1-6}$alkoxy, and $C_{1-6}$haloalkoxy.

7. The compound of claim 1, or a solvate, N-oxide, stereoisomer, or pharmaceutically acceptable salt thereof, wherein each $R^3$ is independently selected from $C_{1-6}$alkyl, C$_{1-6}$haloalkyl, C$_{3-6}$cycloalkyl, -C$_{1-6}$alkyl-C$_{3-6}$cycloalkyl, C$_{2-9}$heterocycloalkyl, phenyl, and -C$_{1-6}$alkyl-phenyl, wherein C$_{3-6}$cycloalkyl, -C$_{1-6}$alkyl-C$_{3-6}$cycloalkyl, C$_{2-9}$heterocycloalkyl, phenyl, and -C$_{1-6}$alkyl-phenyl are optionally substituted with 1 or 2 substituents independently selected from halogen, C$_{1-6}$alkyl, C$_{1-6}$alkynyl, C$_{1-6}$haloalkyl, C$_{1-6}$alkoxy, C$_{1-6}$haloalkoxy, and C(O)OR$^4$.

8. The compound of claim 7, or a solvate, N-oxide, stereoisomer, or pharmaceutically acceptable salt thereof, wherein each R$^3$ is independently selected from C$_{1-6}$alkyl, C$_{1-6}$haloalkyl, phenyl, and -C$_{1-6}$alkyl-phenyl, wherein phenyl and -C$_{1-6}$alkyl-phenyl are optionally substituted with 1 or 2 substituents independently selected from halogen, C$_{1-6}$alkyl, C$_{1-6}$alkynyl, C$_{1-6}$haloalkyl, C$_{1-6}$alkoxy, and C$_{1-6}$haloalkoxy.

9. The compound of claim 8, or a solvate, N-oxide, stereoisomer, or pharmaceutically acceptable salt thereof, wherein R$^3$ is C$_{1-6}$haloalkyl, phenyl, or -C$_{1-6}$alkyl-phenyl, wherein phenyl or -C$_{1-6}$alkyl-phenyl are optionally substituted with 1 or 2 substituents independently selected from halogen, C$_{1-6}$haloalkyl, and C$_{1-6}$haloalkoxy.

10. The compound of claim 1, or a solvate, N-oxide, stereoisomer, or pharmaceutically acceptable salt thereof, wherein n is 1, 2, or 3.

11. The compound of claim 10, or a solvate, N-oxide, stereoisomer, or pharmaceutically acceptable salt thereof, wherein n is 1 or 2.

12. The compound of claim 11, or a solvate, N-oxide, stereoisomer, or pharmaceutically acceptable salt thereof, wherein n is 1.

13. The compound of claim 11, or a solvate, N-oxide, stereoisomer, or pharmaceutically acceptable salt thereof, wherein n is 2.

14. The compound of claim 2, selected from:

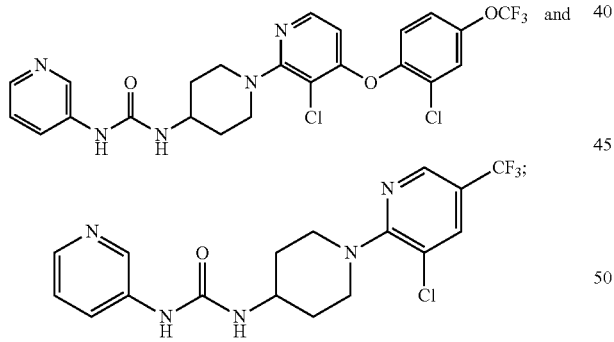

or a solvate, N-oxide, stereoisomer, or pharmaceutically acceptable salt thereof.

15. The compound of claim 1, selected from:

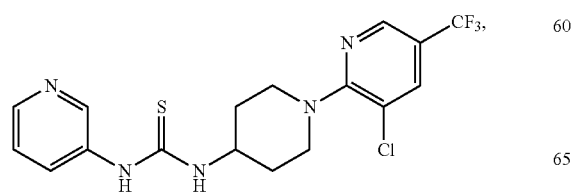

-continued

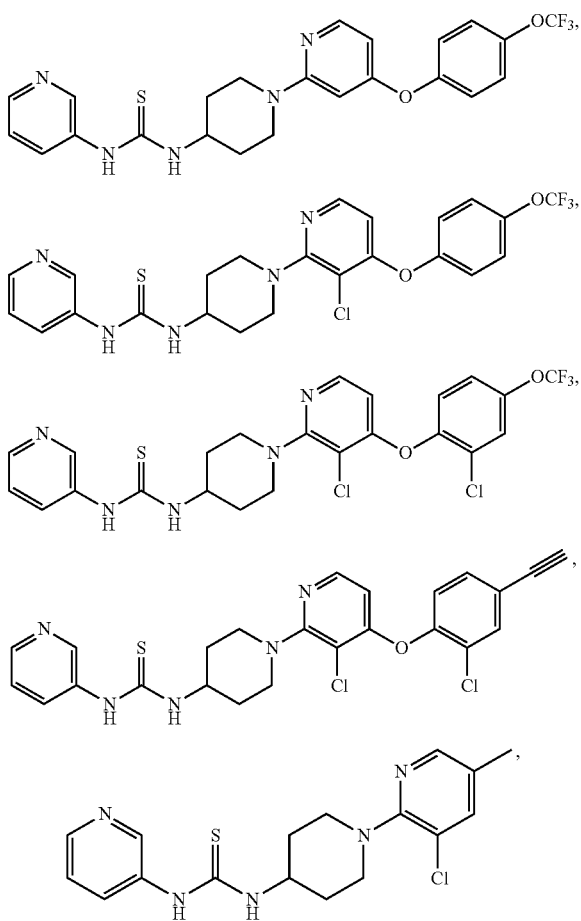

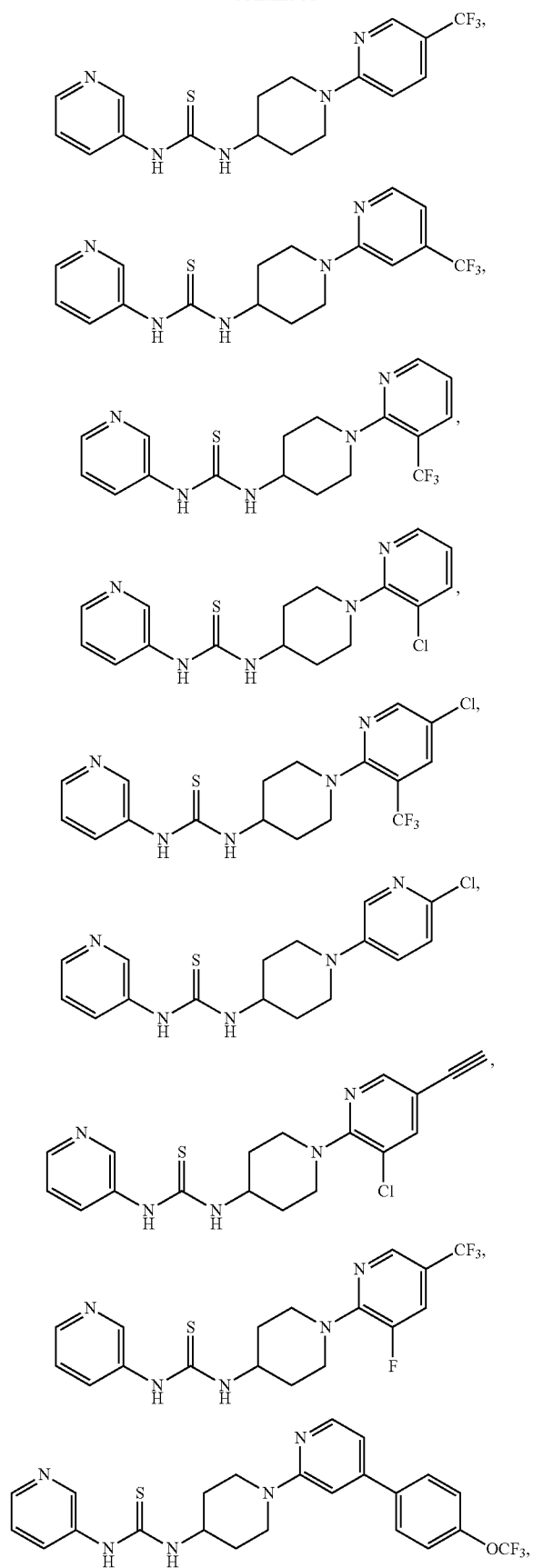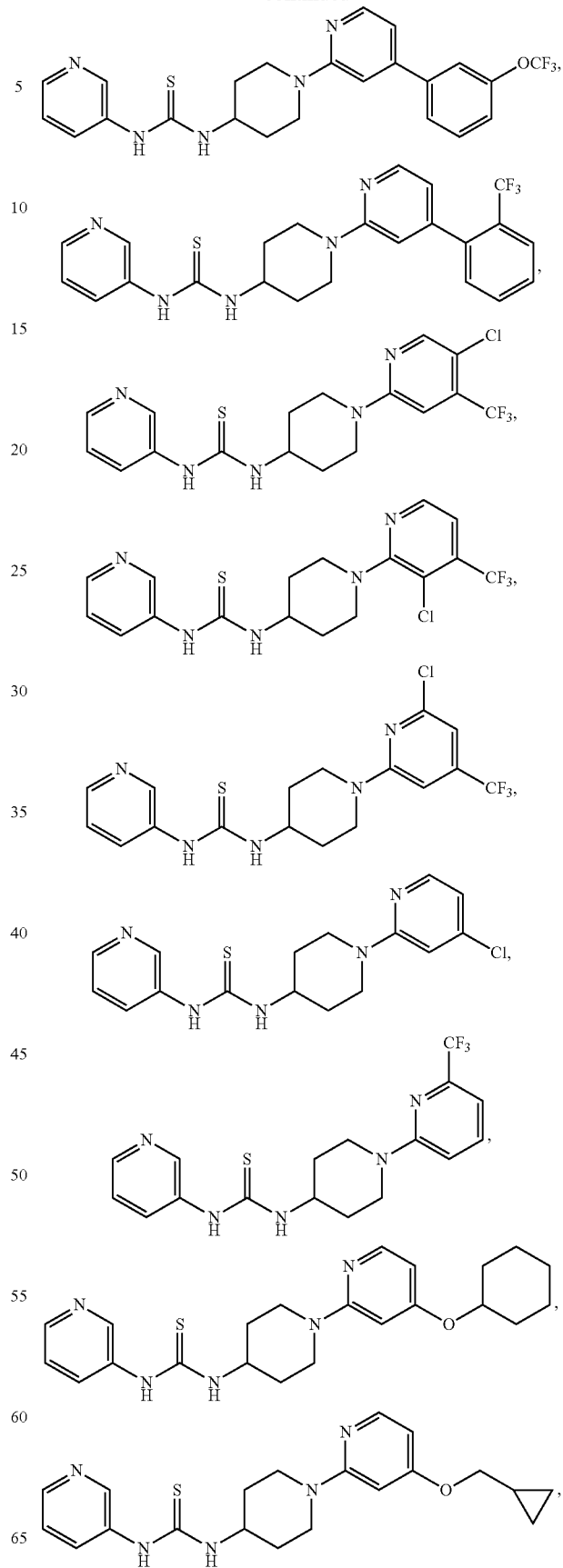

-continued
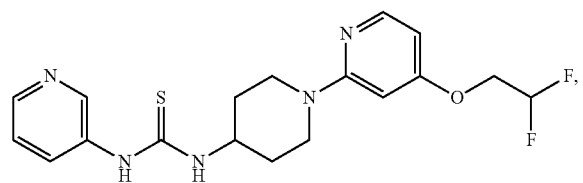
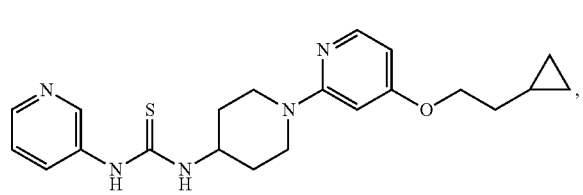
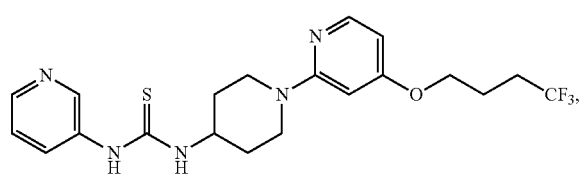
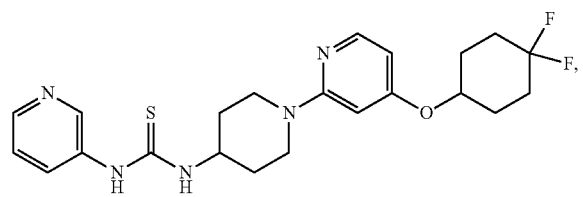
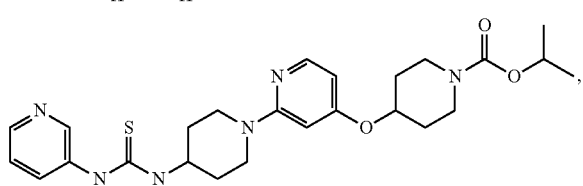
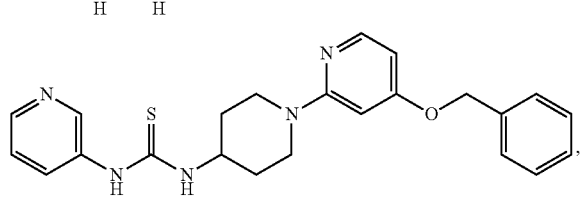
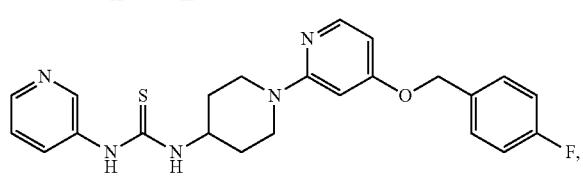
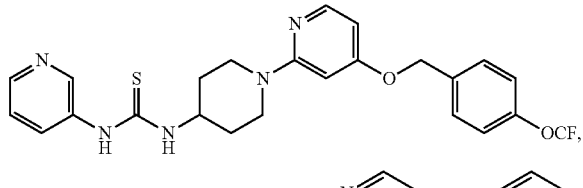
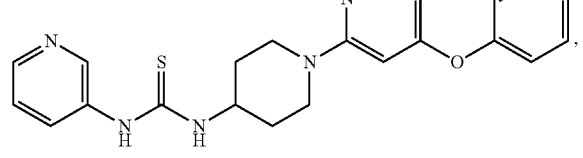
-continued
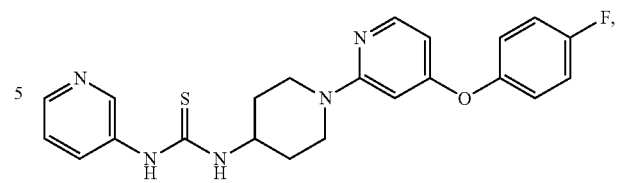
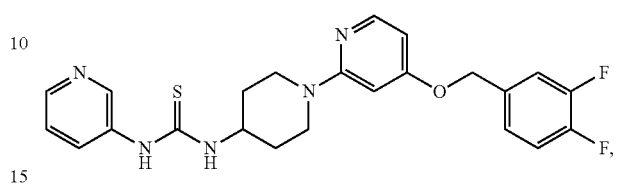
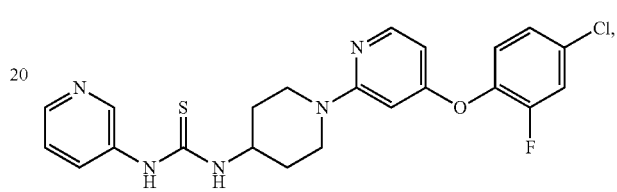
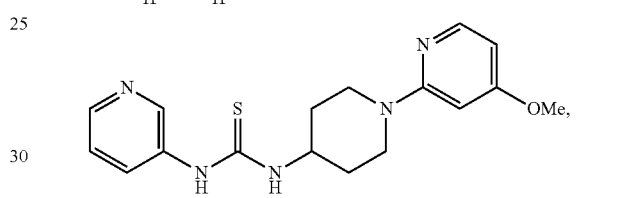
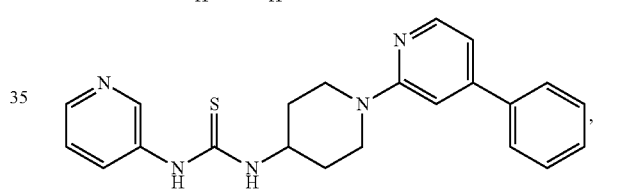
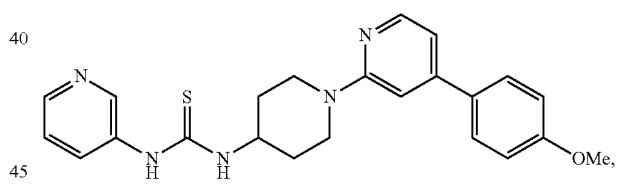
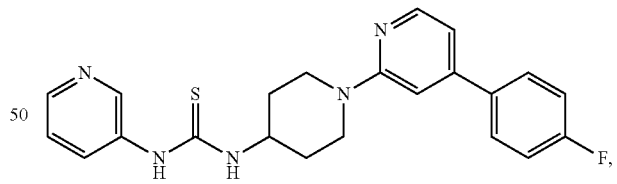
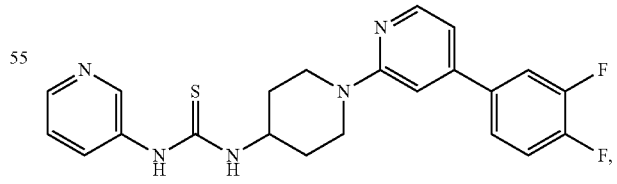
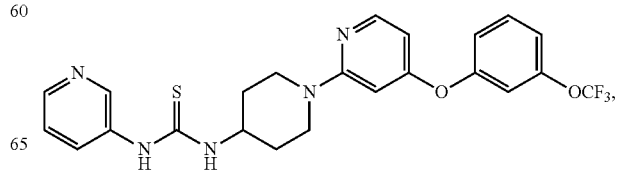

-continued
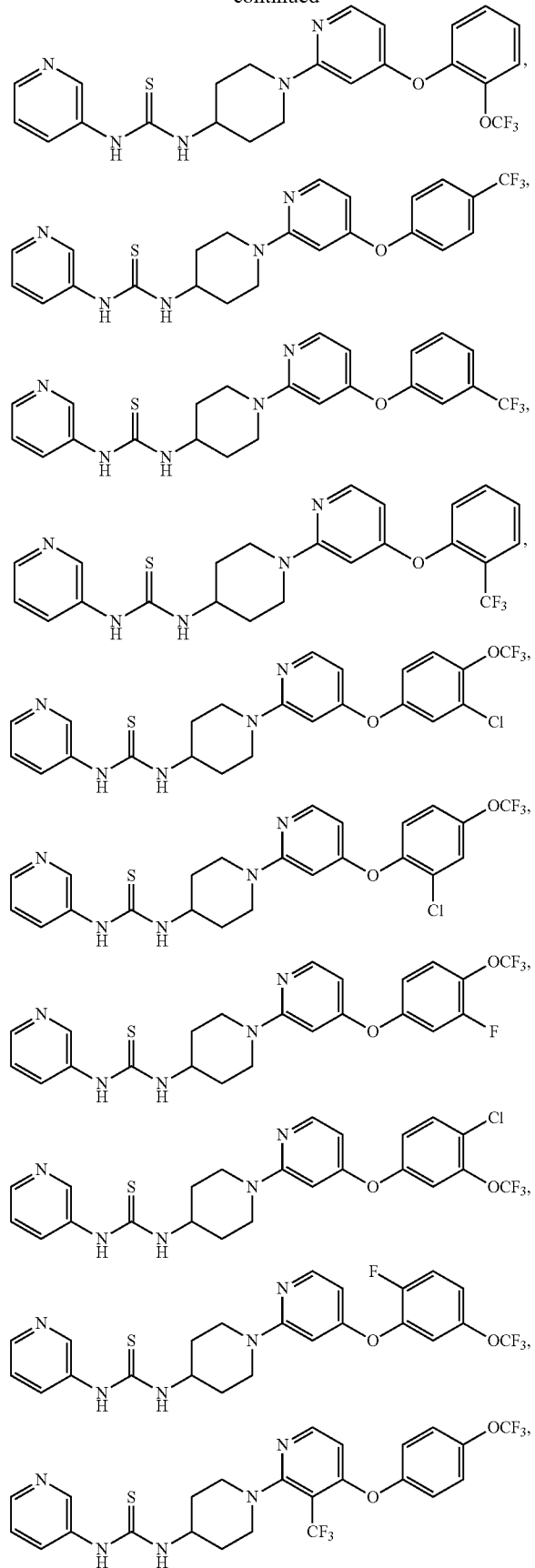
-continued
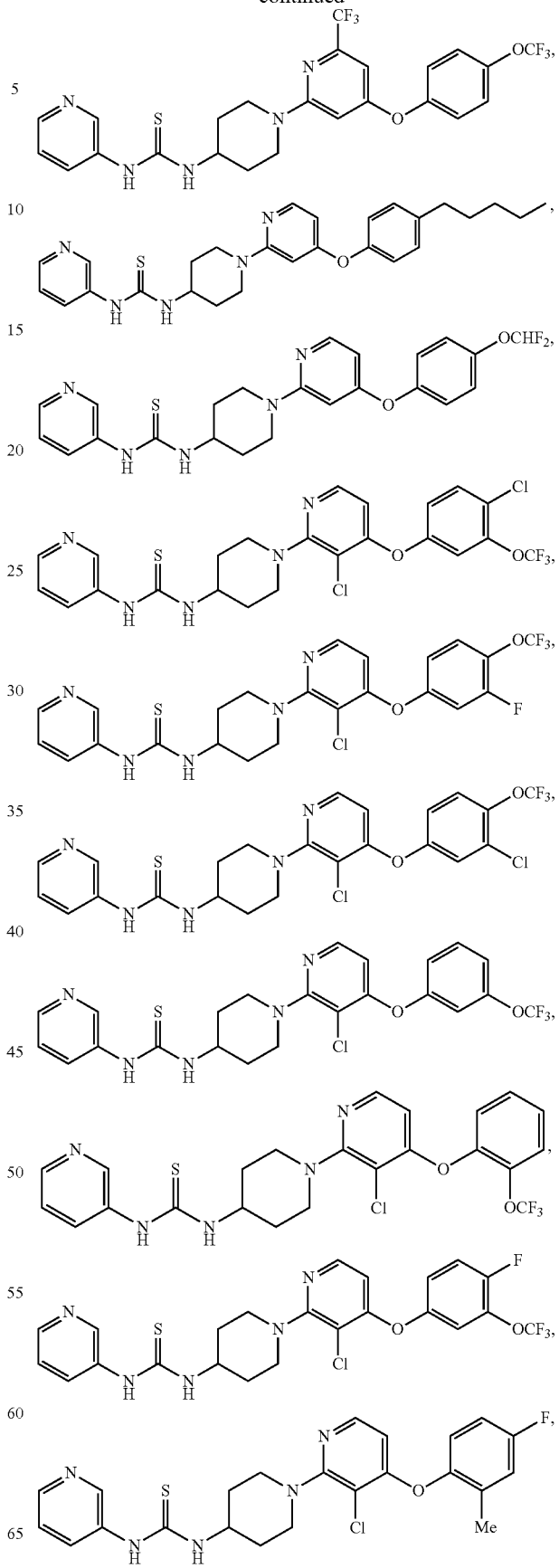

91
-continued
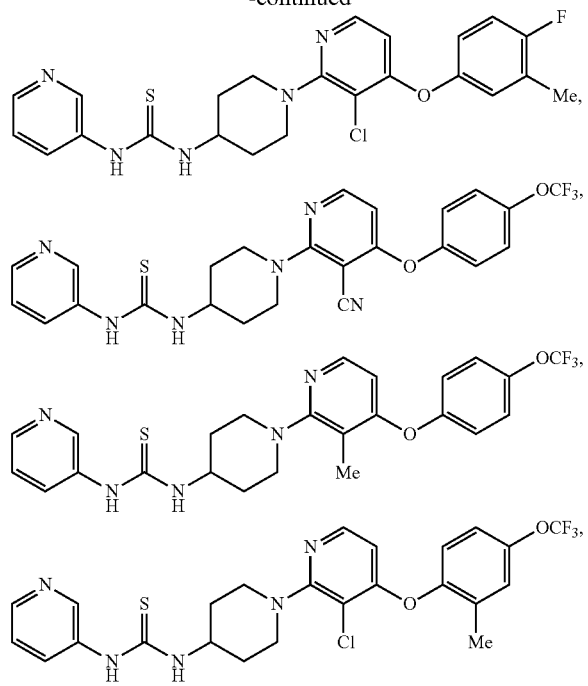
92
-continued
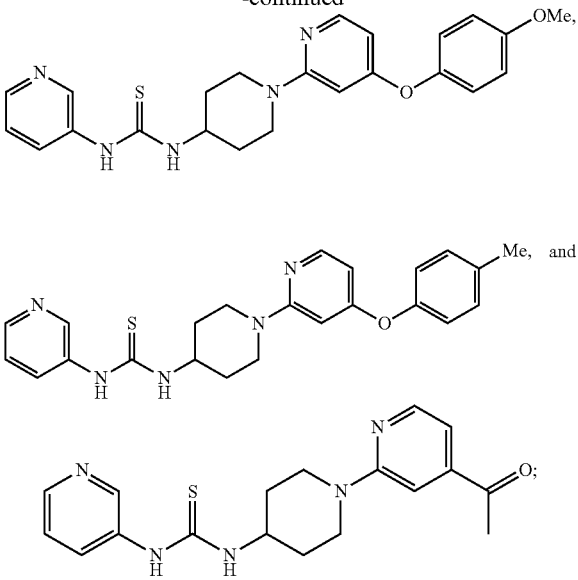
or a solvate, N-oxide, stereoisomer, or pharmaceutically acceptable salt thereof.
16. A compound selected from:
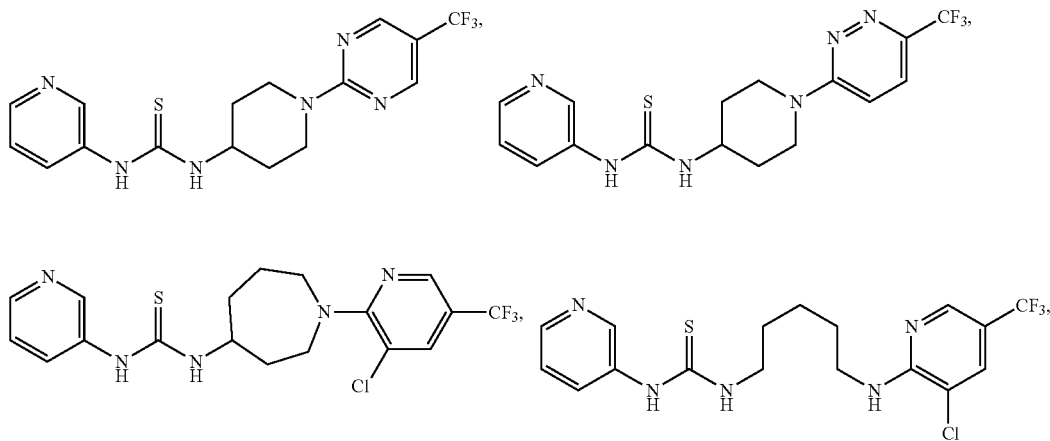
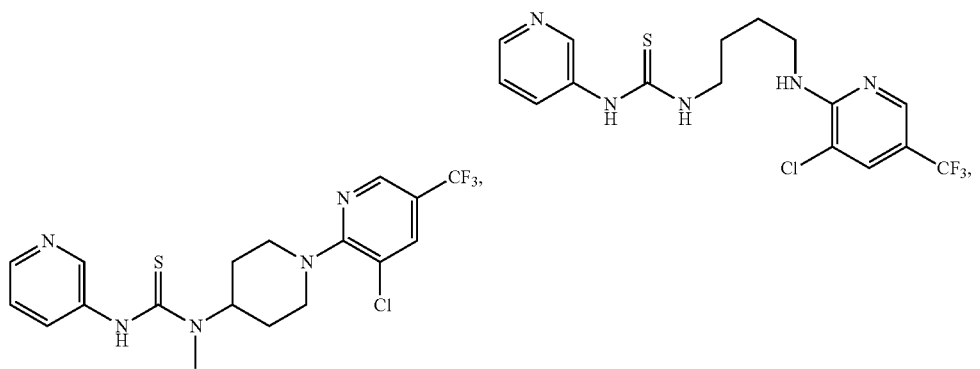

-continued

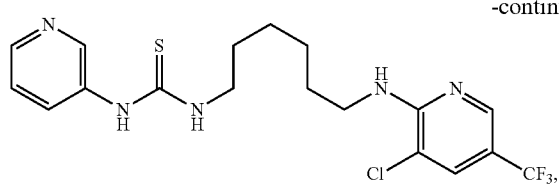

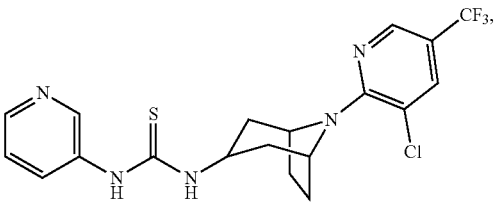

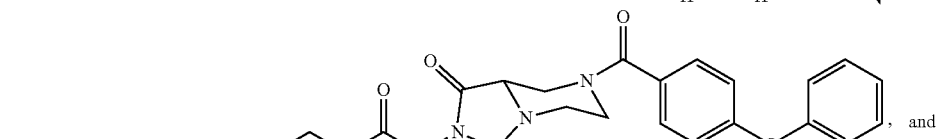

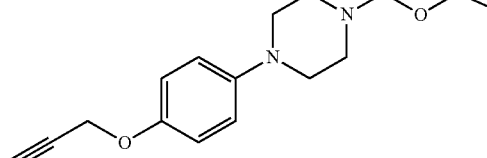

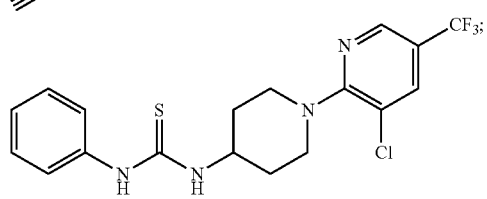

or a solvate, N-oxide, stereoisomer, or pharmaceutically acceptable salt thereof.

17. A pharmaceutical composition comprising a compound of claim 1, or a solvate, N-oxide, stereoisomer, or pharmaceutically acceptable salt thereof, and at least one pharmaceutically acceptable excipient.

18. A method of inhibiting ABHD12 activity in a patient in need thereof, comprising administering to the patient a therapeutically effective amount of a compound of claim 1, or a solvate, N-oxide, stereoisomer, or pharmaceutically acceptable salt thereof.

19. A method of inhibiting ABHD12 activity in a patient in need thereof, comprising administering to the patient a therapeutically effective amount of a compound of claim 1, or a solvate, N-oxide, stereoisomer, or pharmaceutically acceptable salt thereof, wherein administration of the compound stimulates the patient's immune system.

20. A method of inhibiting ABHD12 activity in a patient in need thereof, comprising administering to the patient a therapeutically effective amount of a compound of claim 1, or a solvate, N-oxide, stereoisomer, or pharmaceutically acceptable salt thereof, wherein administration of the compound initiates an immune response.

* * * * *